United States Patent
Keller et al.

(10) Patent No.: US 12,129,490 B2
(45) Date of Patent: Oct. 29, 2024

(54) METHODS FOR GENERATING HEPATOCYTES AND CHOLANGIOCYTES FROM PLURIPOTENT STEM CELLS

(71) Applicants: UNIVERSITY HEALTH NETWORK, Toronto (CA); THE HOSPITAL FOR SICK CHILDREN, Toronto (CA)

(72) Inventors: Gordon Keller, Toronto (CA); Shinichiro Ogawa, Toronto (CA); Anand Ghanekar, Toronto (CA); Christine Bear, Toronto (CA); Binita M. Kamath, Toronto (CA); Mina Ogawa, Toronto (CA); James Surapisitchat, Toronto (CA)

(73) Assignees: UNIVERSITY HEALTH NETWORK, Toronto (CA); THE HOSPITAL FOR SICK CHILDREN, Toronto (CA)

(*) Notice: Subject to any disclaimer, the term of this patent is extended or adjusted under 35 U.S.C. 154(b) by 0 days.

(21) Appl. No.: 16/109,202

(22) Filed: Aug. 22, 2018

(65) Prior Publication Data
US 2020/0157494 A1 May 21, 2020

(51) Int. Cl.
*C12N 5/071* (2010.01)
*A61K 35/407* (2015.01)

(52) U.S. Cl.
CPC ............ *C12N 5/067* (2013.01); *C12N 5/0679* (2013.01); *A61K 35/407* (2013.01); *C12N 2501/01* (2013.01); *C12N 2501/115* (2013.01); *C12N 2501/119* (2013.01); *C12N 2501/12* (2013.01); *C12N 2501/155* (2013.01); *C12N 2501/16* (2013.01); *C12N 2501/237* (2013.01); *C12N 2501/415* (2013.01); *C12N 2501/42* (2013.01); *C12N 2501/724* (2013.01); *C12N 2501/727* (2013.01); *C12N 2501/999* (2013.01); *C12N 2502/00* (2013.01); *C12N 2502/14* (2013.01); *C12N 2503/02* (2013.01); *C12N 2506/02* (2013.01); *C12N 2506/45* (2013.01)

(58) Field of Classification Search
CPC ................ C12N 5/067; C12N 2506/02; C12N 2501/119; C12N 2501/237; C12N 2502/14; C12N 2501/115; C12N 5/06; C12N 2501/12; C12N 2501/415; C12N 2501/42; C12N 5/0679; C12N 2501/01; C12N 2501/155; C12N 2501/16; C12N 2501/724; C12N 2501/727; C12N 2501/999; C12N 2502/00; A61K 35/407
See application file for complete search history.

(56) References Cited

U.S. PATENT DOCUMENTS

| | | | |
|---|---|---|---|
| 8,951,792 B2 | 2/2015 | Heins et al. | |
| 10,844,356 B2 * | 11/2020 | Valamehr | C12N 5/0607 |
| 2011/0280844 A1 | 11/2011 | Junying et al. | |
| 2012/0115226 A1 * | 5/2012 | Stachelsheid | C12N 5/067 |
| | | | 435/366 |
| 2012/0196312 A1 | 8/2012 | Sato et al. | |

FOREIGN PATENT DOCUMENTS

| | | | | |
|---|---|---|---|---|
| EP | 2457998 A1 | 5/2012 | | |
| JP | 2009542215 A | 12/2009 | | |
| JP | 2010534065 A | 11/2010 | | |
| WO | 2008/002662 A2 | 1/2008 | | |
| WO | 2010/049752 A1 | 5/2010 | | |
| WO | WO-2012021845 A2 * | 2/2012 | | A61P 13/02 |
| WO | 2014/124527 A1 | 8/2014 | | |

OTHER PUBLICATIONS

Miki et al. Hepatic Differentiation of Human Embryonic Stem Cells Is Promoted by Three-Dimensional Dynamic Perfusion Culture Conditions Tissue Engineering: Part C vol. 17, No. 5, 2011 (Year: 2011).*
Cai et al. "Directed Differentiation of Human Embryonic Stem Cells into Functional Hepatic Cells" 2007. Hepatology 45(5): 1229-1239 (Year: 2007).*
Tanimizu et al. Notch signaling controls hepatoblast differentiation by altering the expression of liver-enriched transcription factors 2004. Journal of Cell Science 117(15): 3165-3174 (Year: 2004).*
Ito et al. In vitro expansion and functional recovery of mature hepatocytes from mouse adult liver 2012. Liver International 32 (4): 592-601 (Year: 2012).*
Banas et al. Stem Cell Plasticity: Learning From Hepatogenic Differentiation Strategies 2007. Developmental Dynamics 236:3228-3241 (Year: 2007).*

(Continued)

*Primary Examiner* — James D Schultz
*Assistant Examiner* — Masudur Rahman
(74) *Attorney, Agent, or Firm* — RAPHAEL BELLUM PLLC

(57) ABSTRACT

Methods for producing hepatocyte and/or cholangiocyte lineage cells from pluripotent stem cells, the method comprising (a) specifying the extended nodal agonist treated induced endodermal cell population to obtain a cell population comprising hepatocyte and/or cholangiocyte progenitors by contacting the extended nodal agonist treated induced endodermal cell population with specification media comprising a FGF agonist and a BMP4 agonist and/or active conjugates and/or fragments thereof; (b) inducing maturation, and optionally further lineage specification and/or expansion of the hepatocyte and/or cholangiocyte progenitors of the cell population to obtain a population comprising hepatocyte lineage cells such as hepatoblasts, hepatocytes and/or cholangiocytes, the inducing maturation step comprising generating aggregates of the cell population. Optionally, the method also comprises activating the cAMP pathway within the aggregates and forming co-aggregates.

22 Claims, 41 Drawing Sheets

(56) References Cited

OTHER PUBLICATIONS

Lock et al. Expansion and Differentiation of Human Embryonic Stem Cells to Endoderm Progeny in a Microcarrier Stirred-Suspension Culture Tissue Eng Part A. Aug. 2009; 15(8):2051-63 (Year: 2009).*

Soto-Gutierrez et al. Differentiation of mouse embryonic stem cells to hepatocyte-like cells by co-culture with human liver nonparenchymal cell lines, 2007 Nature Protocols 2(2): 347-356 (Year: 2007).*

Mazaris et al. Hepatocyte Transplantation: A Review of Worldwide Clinical Developments and Experiences 2005. Experimental and Clinical Transplantation 3: 306-315 (Year: 2005).*

Lehar et al. Notch ligands Delta1 and Jagged1 transmit distinct signals to T-cell precursors Blood. 2005;105:1440-1447 (Year: 2005).*

Hay et al. Highly efficient differentiation of hESCs to functional hepatic endoderm requires ActivinA and Wnt3a signaling 2008 PNAS 105 (34): 12301-12306 (Year: 2008).*

Basma et al. Basic—Liver, Pancreas, and Biliary Tract 2009 Gastroenterology 136: 990-999 (Year: 2009).*

Nostro et al, Stage-specific signaling through TGFb family members and WNT regulates patterning and pancreatic specification of human pluripotent stem cells; Development 138, 1445 (2011) doi:10.1242/dev.065904 (Year: 2011).*

Touboul et al. Generation of functional hepatocytes from human embryonic stem cells under chemically defined conditions that recapitulate liver development (Hepatology, vol. 51, No. 5, 2010) (Year: 2010).*

Hannan, N.R., Segeritz, C.P., Touboul, T. and Vallier, L., 2013. Production of hepatocyte-like cells from human pluripotent stem cells. Nature protocols, 8(2), pp. 430-437. (Year: 2013).*

Takayama, K., Kawabata, K., Nagamoto, Y., Kishimoto, K., Tashiro, K., Sakurai, F., Tachibana, M., Kanda, K., Hayakawa, T., Furue , M. K. and Mizuguchi, H., 2013. 3D spheroid culture of hESC/hiPSC-derived hepatocyte-like cells for drug toxicity testing. Biomaterials, 34(7), pp. 1781-1789. (Year: 2013).*

International Search Report in International Application No. PCT/CA2014/000122, dated Apr. 29, 2014.

Arpiainen, M. et al., "Coactivator PGC-1 alpha regulates the fasting inducible xenobiotic-metabolizing enzyme CYP2A5 in mouse primary hepatocytes," Toxicology and Applied Pharmacology, 2008, vol. 232, pp. 135-141.

Benet, M. et al., "CCAAT/Enhancer-binding Protein a (C/EBP a) and Hepatocyte Nuclear Factor 4 a(HNF4a) Synergistically Cooperate with Constitutive Androstane Receptor to Transactivate the Human Cytochrome P450 2B6 (CYP2B6) Gene, Application to the Development of a Metabolically Competent Human Hepatic Cell Model," The J. of Bio. Chem. 2010, vol. 285, No. 37. pp. 28457-28471.

Miki, T. et al., "Hepatic Differentiation of Human Embryonic Stem Cells is Promoted by Three-Dimensional Dynamic Perfusion Culture Conditions," Tissue Engineering, Part C, 2011, vol. 17, No. 5, pp. 557-568.

Sivertsson, L. et al., "Hepatic Differentiation and Maturation of Human Embryonic Stem Cells Cultured in a Perfused Three-Dimensional Bioreactor," Stem Cells and Development, Feb. 15, 2013, vol. 22, No. 4, pp. 581-594.

Extended Search Report in corresponding International Application No. EP 14751044, dated Jul. 6, 2016.

Brolen et al., "Hepatocyte-like cells derived from human embryonic stem cells specifically via definitive endoderm and a progenitor stage," J. Biotech. 145, 2010, pp. 284-294.

Hay et al., "Highly efficient differentiation of hESCs to functional hepatic endoderm requires ActivinA and Wnt3a signaling," PNAS, Aug. 26, 2008, vol. 105, No. 34, pp. 12301-12306.

M. Ogawa et al., "Directed differentiation of cholangiocytes from human pluripotent stem cells," Nature Biotech., vol. 33, No. 8, Aug. 2015, pp. 853-861.

S. Ogawa et al., "Three-dimensional culture and cAMP signaling promote the maturation of human pluripotent stem cell-derived hepatocytes," Development, 140, 2013, pp. 3285-3296.

Si-Tayeb et al., "Highly Efficient Generation of Human Hepatocyte-Like Cells from Induced Pluripotent Stem Cells," Hepatology, vol. 51, No. 1, Jan. 1, 2010, pp. 297-305.

Tanimizu et al., "Notch signaling controls hepatoblast differentiation by altering the expression of liver-enriched transcription factors," J. Cell Sci., vol. 117, No. 15, Jul. 1, 2004, pp. 3165-3174.

Zhao et al., "Derivation and Characterization of Hepatic Progenitor Cells from Human Embryonic Stem Cells," Plos One, vol. 4, No. 7, Jul. 1, 2009, pp. 1-10.

Office Action in Chinese Application No. 201480021570.7, dated Jul. 13, 2017.

Zhi-Gang Tian The forefront of liver disease research:, Beijing, Peking Union Medical College Press, 1st Edition, Aug. 2012, pp. 98-106.

Lye T. Lock and Emmanuel S. Tzanakakis "Expansion and Differentiation of Human Embryonic Stem Cells to Endoderm Progeny in a Microcarrier Stirred-Suspension Culture", Tissue Engineering: Part A, vol. 15, Nov. 8, 2009; pp. 2051-2063.

Yu et al., "Hepatitic Differentiation from Human Embryonic Stem Cells Using Stromal Cells", Journal of Surgical Research, 170, (2011). e253-e261.

* cited by examiner

ALB

METHODS FOR GENERATING HEPATOCYTES AND CHOLANGIOCYTES FROM PLURIPOTENT STEM CELLS

FIELD

The disclosure relates to methods for producing functional hepatocytes from human pluripotent stem cells.

BACKGROUND

The ability to produce functional hepatocytes from human pluripotent stem cells (hPSCs; including embryonic stem cells; hESCs and induced pluripotent stem cells; hiPSCs) will provide a source of hepatocytes for drug metabolism studies and cell-based therapy for the treatment of liver diseases. Hepatocytes are of particular importance as they are the cells responsible for drug metabolism and thus for the control of xenobiotic elimination from the body[1][3]. Given this role and the fact that individuals can differ in their ability to metabolize a particular drug[4], access to functional hepatocytes from a representative population sample would have a dramatic impact on drug discovery and testing within the pharmaceutical industry. In addition to providing new platforms for drug testing, hPSC-derived hepatocytes can offer potential new therapies for patients with liver disease. Although liver transplantation provides an effective treatment for end-stage liver disease, a shortage of viable donor organs limits the patient population that can be treated with this approach[5][7]. Hepatocyte transplantation and bio-artificial liver devices developed with hPSC-derived hepatocytes represent alternative life-saving therapies for patients with specific types of liver disease. These applications are, however, dependent on the ability to generate mature metabolically functional cells from the hPSCs. Reproducible and efficient generation of such cells has been challenging to date, due to the fact that the regulatory pathways that control hepatocyte maturation are poorly understood.

Given the potential therapeutic and commercial importance of functional human hepatocytes, significant effort has been directed towards optimizing protocols for the generation of these cells from hPSCs[8][16]. Almost all approaches have attempted to recapitulate the key stages of liver development in differentiation cultures, including the induction of definitive endoderm, the specification of the endoderm to a hepatic fate, the generation of hepatic progenitors known as hepatoblasts and the differentiation of hepatoblasts to mature hepatocytes[17]. In most studies, differentiation is induced in a monolayer format with the sequential addition of pathway agonists and antagonists that are known to regulate the early stages of development including endoderm induction and hepatic specification. With this strategy, it has been possible to optimize these early differentiation steps and generate populations that are highly enriched in definitive endoderm, hepatoblasts and immature hepatocytes as defined by expression of markers such as Hex, alpha-fetoprotein and albumin[17]. While these early differentiation steps are reasonably well established, conditions that promote the maturation of the hepatocytes for example, to functional cells as defined by Phase I and Phase II drug-metabolizing enzyme activities, have not been described. The populations produced with the different protocols vary considerably in their maturation status and in most cases represent immature hepatocytes.

SUMMARY

An aspect of the disclosure includes a method of producing hepatocyte lineage cells from an extended nodal agonist treated induced endodermal cell population, the method comprising:

(a) specifying the extended nodal agonist treated induced endodermal cell population to obtain a cell population comprising hepatocyte progenitors by contacting the extended nodal agonist treated induced endodermal cell population with specification media comprising an FGF agonist and a BMP4 agonist and/or active conjugates and/or fragments thereof;

(b) inducing maturation, optionally further lineage specification and/or expansion of the hepatocyte progenitors of the cell population to obtain a population comprising hepatocyte lineage cells such as hepatoblasts, hepatocytes and/or cholangiocytes, the inducing maturation step comprising generating aggregates of the cell population.

In an embodiment, the hepatocyte and/or cholangiocyte lineage cells are hepatoblasts. In an embodiment, the method produces an expanded population of hepatoblasts. In another embodiment the hepatocyte lineage cells are mature hepatocytes or the cholangiocyte lineage cells are mature cholangiocytes.

In some embodiments, the extended nodal agonist treated induced endodermal cell population is induced from pluripotent stem cells (PSCs) such as embryonic stem cells (ESCs) or induced pluripotent stem cells (iPSCs). The pluripotent stem cells are optionally human ESCs (hESCs) or human iPSCs (hiPSCs).

The extended nodal agonist treated induced endoderm population is, in an embodiment, obtained by inducing endoderm cells in embryoid bodies (EBs). In another embodiment, the extended nodal agonist treated induced endodermal population is obtaining by inducing endoderm cells that are in a monolayer. In each case, the induced endodermal population is cultured in the presence of a nodal agonist, for example activin, for an extended period to produce an extended nodal agonist treated induced endodermal population.

In an embodiment, the extended nodal agonist-treated, induced endodermal population comprises at least, 80%, 85%, 90%, 95% CXCR4 and cKIT positive cells and/or at least 70%, 75%, 80% SOX17$^+$ cells.

In an embodiment, the specifying step comprises contacting an extended nodal agonist treated (e.g. activin-treated) induced endodermal population with specification media comprising an FGF and an BMP4. The FGF can for example be FGF10, FGF2 or FGF4 or combinations thereof. The combinations can for example be added sequentially.

In an embodiment, the specifying step comprises first contacting an extended nodal agonist-treated, induced endodermal population with specification media comprising FGF10 and BMP4 for approximately 40 to 60 hours, optionally approximately 40, 42, 44, 46, 48, 50, 52, 54, 56, 58 or 60 hours and then contacting the extended nodal agonist treated induced endodermal population with specification media comprising bFGF and BMP4 for about 4 to 7 days, optionally about 4, 5, 6, or 7 days.

In another embodiment, the aggregates are generated from a cell population comprising at least 70%, 80%, 85%, or 90% albumin positive cells. In another embodiment, the aggregates are generated after 24, 25, 26, 27, or 28 days in culture.

In some embodiments, aggregates are generated from a monolayer of the cell population comprising hepatocyte and/or cholangiocyte progenitors by enzymatic treatment and/or manual dissociation.

Inducing maturation, and optionally further lineage specification and/or expansion can comprise one or more additional steps. In a further embodiment, the cell population comprising hepatocyte and/or cholangiocyte progenitors and/or the aggregates are cultured in the presence of hepatocyte growth factor (HGF), dexamethasone (DEX) and/or Oncostatin M (OSM) and/or active conjugates and/or fragments thereof.

In one embodiment, inducing maturation, and optionally further lineage specification and/or expansion further comprises activating the cAMP pathway within the cells of the aggregates to induce the maturation of the hepatocyte and cholangiocyte progenitors into hepatocytes and/or cholangiocytes. In another embodiment, activating the cAMP pathway comprises contacting the aggregates with cAMP and/or a cAMP analog (e.g. such as 8-bromoadenosine-3',5'-cyclic monophosphate, dibutyryl-cAMP, Adenosine-3',5'-cyclic monophosphorothioate, Sp-isomer (Sp-cAMPS) and/or 8-Bromoadenosine-3', 5'-cyclic monophosphorothioate, Sp-isomer (Sp-8-Br-cAMPS)) and/or any other cAMP agonist.

For example, in an embodiment, a maturation media comprising a cAMP agonist and DEX and optionally HGF is added to the aggregates subsequent to culturing the pre-aggregate population in a maturation media comprising HGF, DEX and OSM, for example for about 10, 11, 12, 13 or 14 days.

In an embodiment, the population of hepatocytes produced is a population comprising functional hepatocytes.

In embodiments, the hepatocytes, optionally functional hepatocytes, comprise increased expression of at least 1, 2, 3, 4, 5, 6, 7, 8, 9, 10 or more genes or protein selected from the group consisting of ALB, CPS1, G6P, TDO, CYP2C9, CYP2D6, CYP7A1, CYP3A7, CYP1A2, CYP3A4, CYP2B6, NAT2 and UGT1A1 compared to a cell population comprising hepatocyte and/or cholangiocyte progenitors, and/or hepatocytes produced from a non-extended nodal agonist treated induced endodermal cell population (e.g. from an induced endodermal population that was not treated with a nodal agonist such as activin for an extended period of time), produced without aggregation and/or cAMP signaling induction. In other embodiments, at least 40%, 50%, 60%, 70%, 80% or 90% of the hepatocytes, optionally functional hepatocytes, are ASGPR-1$^+$ cells.

In an embodiment, cholangiocyte fate is specified by treating aggregates of the cell population with a notch agonist.

In an embodiment, the population of cholangiocytes produced is a population of functional cholangiocytes. The functional cholangiocytes comprise for example increased expression of at least 1, at least 2 or 3 genes or proteins selected from Sox9, CK9 and CFTR (Cystic fibrosis transmembrane conductance regulator) compared to the cells of the cell population comprising hepatocyte and cholangiocyte progenitors and/or compared to a population cells produced from aggregates not treated with a notch agonist. In other embodiments, at least 40%, 50%, 60%, 70%, 80% or 90% of the population of cholangiocytes are CK19$^+$ cholangiocytes. In other embodiments, at least 40%, 50%, 60%, 70%, 80% or 90% of the functional cholangiocytes are CFTR$^+$ cholangiocytes.

As mentioned, the method can be applied to an endodermal cell population grown in a monolayer.

Accordingly a further aspect includes a method of producing hepatocytes and/or cholangiocytes from a pluripotent stem cell population, the method comprising:

a) contacting the pluripotent stem cells cultured as a monolayer, with an induction media comprising nodal agonist such as ActA and optionally a wnt/beta-catenin agonist such as i) Wnt3a and/or ii) a GSK-3 selective inhibitor such as CHIR-99021, to provide an induced endodermal cell population;

b) contacting the induced endodermal cell population with a nodal agonist to provide an extended nodal agonist treated induced endodermal cell population;

c) specifying the extended nodal agonist treated induced endodermal cell population by contacting the extended nodal agonist treated induced endodermal cell population with a specification media comprising an FGF agonist and an BMP4 agonist and/or active conjugates and/or fragments thereof to obtain a cell population comprising hepatocyte and/or cholangiocyte progenitors;

d) optionally contacting the cell population comprising hepatocyte and/or cholangiocyte progenitors with a maturation media comprising HGF, dexamethasone and/or Oncostatin M and/or active conjugates and/or fragments thereof; and e) inducing maturation, optionally further lineage specification and/or expansion of hepatocyte and cholangiocyte progenitors of the cell population into expanded hepatoblasts, hepatocytes and/or cholangiocytes, the inducing maturation comprising generating aggregates of the cell population.

Further, the endodermal population can also be comprised in embryoid bodies.

Accordingly, a further aspect of the disclosure provides a method of producing hepatocytes and/or cholangiocytes from a pluripotent stem cell population, the method comprising:

a) forming embryoid bodies (EBs) of the pluripotent stem cells, optionally by contacting the pluripotent stem cells with a BMP4 agonist;

b) contacting the EBs with an induction media comprising a nodal agonist such as ActA and optionally a wnt/beta-catenin agonist such as i) Wnt3a and/or ii) a GSK-3 selective inhibitor such as CHIR-99021, to provide an induced endodermal cell population;

c) dissociating the induced endodermal cell population to provide a dissociated induced endodermal cell population;

d) contacting the dissociated induced endodermal cell population with a nodal agonist to provide an extended nodal agonist treated induced endodermal cell population;

e) specifying the extended nodal agonist treated induced endodermal cell population by contacting the extended nodal agonist treated induced endodermal cell population with a specification media comprising an FGF agonist and an BMP4 agonist and/or active conjugates and/or fragments thereof to obtain a cell population comprising hepatocyte and/or cholangiocyte progenitors;

f) optionally contacting the cell population comprising hepatocyte and/or cholangiocyte progenitors with a maturation media comprising HGF, dexamethasone and/or Oncostatin M and/or active conjugates and/or fragments thereof; and g) inducing maturation, further lineage specification and/or expansion of hepatocyte and cholangiocyte progenitors of the cell population into hepatocytes and/or cholangiocytes, the inducing maturation, further lineage specification and/or expansion comprising generating aggregates of the cell population.

In some embodiments, the inducing maturation, further lineage specification and/or expansion step further comprises activating the cAMP pathway within the aggregates to induce the maturation of hepatocyte and/or cholangiocyte progenitors of the cell population into a population comprising hepatocytes and/or cholangiocytes. In an embodiment, the method comprises contacting the aggregates with a cAMP analog and/or cAMP agonist.

In an embodiment, the monolayer or EBs are contacted with a nodal agonist in induction media for at least about 1 day, 2 days, 3 days or about 4 days.

In an embodiment, in a step prior to dissociation of the endodermal population (e.g. embryoid bodies (EB) stage), the EBs are cultured with a nodal agonist for at least 36, 38, 42, 44, 46, 48, 50, 52, 56, 58 or 60 hours or for at least about 1 day, 2 days, 3 days or about 4 days.

Accordingly in another aspect of the disclosure relates to a method of producing hepatocytes and/or cholangiocytes from pluripotent stem cells (PSCs) such as embryonic stem cells (ESCs) or induced pluripotent stem cells (iPSCs), the method comprising:
  a) contacting the pluripotent stem cells cultured as a monolayer or formed into embryoid bodies, with an induction media comprising nodal agonist such as ActA and optionally a wnt/beta-catenin agonist such as i) Wnt3a and/or ii) a GSK-3 selective inhibitor such as CHIR-99021 to provide an induced endodermal cell population;
  b) contacting the induced endodermal cell population with a nodal agonist to provide an extended nodal agonist treated induced endodermal cell population; and
  c) specifying the extended nodal agonist treated induced endodermal cell population by contacting the extended nodal agonist treated induced endodermal cell population with a specification media comprising at least one FGF agonist and one BMP4 agonist and/or active conjugates and/or fragments thereof to obtain a cell population comprising hepatocyte and/or cholangiocyte progenitors; and
  d) inducing maturation, further lineage specification and/or expansion of hepatocyte and/or cholangiocyte progenitors into hepatocytes and/or cholangiocytes, the inducing maturation, further lineage specification and/or expansion comprising:
    (i) culturing the cell population comprising hepatocyte and/or cholangiocyte progenitors with a maturation media comprising HGF, OSM and DEX;
    (ii) generating aggregates of the cell population, optionally when the cell population comprises at least 70%, 80%, 85%, or 90% albumin positive cells or after about 20 to about 40 days of culture for example after about 24 to about 28 days of culture;
    (iii) culturing the aggregated cells in an aggregated cell maturation media; and
    (iv) activating the cAMP pathway in the aggregated cells, optionally within about 1 to about 10 days of aggregation, for example within 6 days of aggregation, optionally after about 27 to about 36 days of culture.

In an embodiment, the aggregated cell maturation media can comprise factors which promote hepatocyte maturation or factors which promote cholangiocyte development or both.

In another embodiment, aggregated cells are upon aggregation treated with a wnt agonist such as CHIR 99021, optionally in the presence of a TGFbeta antagonist such as SB431542. As demonstrated herein, activation of the Wnt pathway and SMAD pathway at for example day 26 (or optionally one or two days later e.g. day 27, in embodiments using EBs), promotes expansion of an albumin+/HNF4+ progenitor population. It is demonstrated for example that up to a 10-fold expansion of said population can be obtained when a wnt agonist is added.

In an embodiment, the aggregated cells are treated with a wnt agonist and optionally a TGFbeta antagonist (such as SB 431542) for about 6 to about 12 days, preferably about 8 to about 10 days, optionally for about 9 days.

In yet a further embodiment, a Wnt antagonist such as XAV939 (also referred to as XAV for short) and/or a Mek/Erk antagonist, for example PD0325901 (also referred to as PD for short) is added during the cAMP activation step. Addition of a Wnt antagonist and/or a MEK/Erk antagonist during activation of cAMP signaling enhances expression of CYP enzymes, for example up to levels or greater than levels seen in adult liver cells. For example, an inhibitor of MEK/Erk added in the presence of cAMP, for example, added to about day 28 to about day 32 cultures, results in hepatocytes with increased levels of CYP3A4 a. Addition of a MEK/Erk antagonist in combination with a Wnt antagonist is shown to also increase levels of CYP1A2. In an embodiment, the Wnt antagonist is XAV939. In another embodiment, the MEK/Erk antagonist is PD0325901.

In an embodiment, approximately 1 to about 4 days after aggregation, the cells are treated with a notch agonist. Addition of a notch agonist at such stages promotes cholangiocyte maturation. In some embodiments, for example where cholangiocyte maturation is preferred, inducing cAMP signaling is omitted.

Further inhibiting Notch signaling for example with a Notch antagonist such as gamma-secretase inhibitor (GSI) L695.458 is demonstrated herein to inhibit cholangiocyte development and cells produced retain the characteristics of hepatocytes. In an embodiment, the method comprises approximately 1 to about 4 days after aggregation, treating the cells with a notch antagonist, for example in embodiments where hepatocyte differentiation is desired.

In another embodiment, the method of producing hepatocytes and/or cholangiocytes from pluripotent stem cells (PSCs), such as embryonic stem cells (ESCs) or induced pluripotent stem cells (iPSCs), comprises:
  a) contacting the pluripotent stem cells cultured as a monolayer or formed into embryoid bodies, with an induction media comprising a nodal agonist such as ActA and optionally a wnt/beta-catenin agonist such as i) Wnt3a and/or ii) a GSK-3 selective inhibitor such as CHIR-99021, optionally for about 4 to about 8 days, to provide an induced endodermal cell population;
  b) contacting the induced endodermal cell population with a nodal agonist, optionally for about 1, 2, 3, or about 4 days, to provide an extended nodal agonist treated induced endodermal cell population;
  c) specifying the extended nodal agonist treated induced endodermal cell population by contacting the extended nodal agonist treated induced endodermal cell population with a specification media comprising at least one FGF agonist and at least one BMP4 agonist and/or active conjugates and/or fragments thereof, optionally for about 4 to about 10 days, to obtain a cell population comprising hepatocyte and/or cholangiocyte progenitors; and d) inducing maturation, further lineage specification and/or expansion of the hepatocyte or cholangiocyte progenitors into hepatocytes and/or cholangiocytes, the inducing maturation, further lineage specification and/or expansion comprising:
  (i) culturing the cell population comprising hepatocyte and/or cholangiocyte progenitors with a maturation media comprising HGF, Dex and/or OSM, optionally for about 10 to 14 days;
  (ii) generating aggregates of the cell population, optionally when the cell population comprises at least 70%, 80% 85%, or 90% albumin positive cells or after about 20 to about 40 days for example after about 24 to about 28 days of culture;
  (iii) culturing the aggregates in maturation medium comprising Dex for about 1 to 10 days;
  iv) a) culturing aggregates in a maturation medium comprising Dex and a cAMP analog and/or cAMP agonist for about 6 days to about 10 days, optionally adding the cAMP analog and/or cAMP agonist within about 1 to about 10 days of the generating aggregates step, for example within 6 days of the generating aggregates step, optionally after about 27 to about 36 days of culture; or
    b) culturing the aggregates in a maturation medium comprising a notch agonist and optionally a cAMP agonist, HGF, and/or EGF for about 6 days to about 20 days, optionally adding the notch agonist within about 1 to about 10 days of the generating aggregates step, for example within 6 days of the generating aggregates step, optionally after about 20 to 40 days of culture.

In an embodiment, the method comprises aggregating for example after about 20 days of culture and/or before 40 days of culture The disclosure also provides a method of inducing maturation, further lineage specification and/or expansion of cholangiocyte progenitors into cholangiocytes, the inducing maturation, further lineage specification and/or expansion comprising:
  (i) culturing a cell population comprising cholangiocyte progenitors with a Notch agonist to induce the maturation of at least one cholangiocyte progenitor into a cholangiocyte, optionally a functional cholangiocyte.

The notch agonist can for example be any notch ligand bound to a surface such as a cell, plastic, ECM or bead. In one embodiment, the notch ligand is notch ligand delta. In one embodiment, inducing maturation, further lineage specification and/or expansion comprises contacting a cell population comprising cholangiocyte progenitors with a notch signaling donor (e.g. notch agonist) such as OP9, OP9delta, and/or OP9 Jagged1 cells and optionally in the presence of EGF, TGFbeta1, HGF and EGF, and/or HGF, TGFbeta1 and EGF for at least or about 5 to about 90 days, to induce the maturation of cholangiocyte progenitors into functional cholangiocytes.

Optionally, contacting a cell population comprising cholangiocyte progenitors with a notch agonist (e.g. a notch signaling donor) comprises co-culturing the cell population comprising cholangiocyte progenitors with a notch signaling donor such as OP9, OP9delta, and/or OP9 Jagged1 cells and optionally in maturation media comprising EGF, TGFbeta1, HGF and EGF, and/or HGF, TGFbeta1 and EGF, for at least or about 5 to at least or about 90 days, optionally for at least or about 5 to at least or about 90 days, optionally for at least or about 5 to at least or about 60 days, at least or about 30 days, at least or about 25 days, 2 at least or about 1 days and/or at least or about 14 days to induce the maturation of cholangiocyte progenitors into cholangiocytes, optionally functional cholangiocytes, optionally wherein the functional cholangiocytes form branched, cyst, tubular or sphere type structures.

In another embodiment, the application provides a method comprising:
  a) producing a population of cells comprising hepatocytes and/or cholangiocytes according to any of the methods described herein; and
  b) introducing the population of cells, or optionally a hepatocyte and/or a cholangiocyte enriched or isolated population, into a subject.

In some embodiments, the method further comprises enriching or isolating a hepatocyte and/or cholangiocyte population of cells. Optionally, the hepatocyte and/or cholangiocyte population of cells comprises at least 10%, at least 15%, at least 20%, at least 25%, at least 30%, at least 35%, at least 40%, at least 50%, at least 60%, at least 70%, at least 80% or up to about 95% hepatocytes and/or cholangiocytes (e.g. optionally functional hepatocytes and/or cholangiocytes).

The disclosure also provides the use of the population of hepatocytes and/or cholangiocytes for drug discovery, drug metabolism analysis, development of bioartificial liver devices and/or as cell replacement therapy for the treatment of liver conditions and disease.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 1A is a schematic representation of the differentiation protocol. EBs are trypsinized at day six and plated as a monolayer in the presence of activin for two days to generate appropriate-staged definitive endoderm. The hepatic lineage is specified from this endoderm population by culture in the presence of BMP4 and FGF. Hepatic maturation is induced through a step wise process, first by the addition of HGF, Dexamethasone (Dex) and Oncostatin M (OSM) for 12 days followed by the generation of 3D aggregates that are cultured for eight days in hepatocyte medium supplemented with Dex and subsequently in this medium with the addition of the cAMP analog, 8-br-cAMP for another 12 days (day 32-44).

FIG. 1B shows flow cytometric analyses showing the proportion of CXCR4$^+$, CKIT$^+$ (CD117) and EPCAM$^+$ cells in day six activin- and activin/Wnt3a-induced populations.

FIG. 1C shows intracellular flow cytometric analyses showing the proportion of SOX17$^+$ and FOXA2$^+$ cells in day six activin- and activin/Wnt3a-induced populations. The size of the SOX17$^+$ and FOXA2$^+$ populations was significantly larger in the activin/Wnt3a induced EBs (Sox17: 96.2+/−1.1%, FoxA2: 88.5+/−2.9%) compared to EBs induced with activin alone (Sox17: 91+/−1.8%, FoxA2: 80.3+/−2.5%) * P<0.05 (P=0.002), ** P<0.01 (P=0.005); Student's t-test, n=4.

FIG. 1D shows RT-qPCR based analyses of T, SOX17, GSC and FOXA2 expression in activin and activin/Wnt3a-induced EBs. EBs were analyzed at the indicated time points. Bars represent SD of the mean of three independent experiments.

FIG. 1E is a flow cytometric analysis showing the kinetics of development of the $CXCR4^+$, $CKIT^+$, $SOX17^+$ and $FOXA2^+$ populations in the activin/Wnt3a induced EBs.

FIG. 1F is a flow cytometric analysis showing the proportion of $CXCR4^+$, $CKIT^+$, $EPCAM^+$, $Sox17^+$ and $FOXA2^+$ cells in day six EBs induced with activin in with neural based media.

FIG. 3A is an intracellular flow cytometric analysis showing the proportion of $SOX17^+$ and $FOXA2^+$ cells in day six activin/Wnt3A-induced EBs as well as in monolayer populations derived from them. The monolayer populations were cultured either directly in the specification media (−activin) or for two days in activin (50 ng/ml) and then in the specification media (+activin). Populations were analyzed following two or four days culture in the specification media (total days eight and 10 for the −activin group and days 10 and 12 for the +activin group). Bars represent standard deviation (SD) of the mean of three independent experiments. The proportion of $SOX17^+$ at day 10/12 was significantly higher in the activin-treated compared to the non-treated population (73.3+/−7.5% vs 45.9+/−3.7%). Similarly, the proportion of $FOXA2^+$ cells at days 8/10 and day 10/12 was significantly higher in the activin treated compared to the non-treated population (day 8: 96.1+/−0.9% vs 76.5+/−10.1%, day 12: 92.7+/−2.5% vs 50.2+/−6.3%).

FIG. 3B depicts total cell number in activin treated and non-treated monolayer cultures. Day six EB-derived cells were cultured directly in hepatic differentiation media or in the presence of activin for two days and then in hepatic differentiation media.

FIG. 3C is a flow cytometric analysis showing the proportion of CXCR4 and CKIT positive cells in populations at days 8, 10 and 12 culture generated from non-treated cell and activin-treated endoderm.

FIG. 3D shows RT-qPCR based expression analyses of hepatic monolayer populations generated from activin-treated (Black bars) and non-treated (Grey bars) endoderm. The populations were analyzed for expression of the indicated endoderm (HEX, AFP, ALB, and HNF4a) and mesoderm (MEOX1, MESP1, CD31 and CD90) genes. Activin treated populations (grey bars) were analyzed at days 12, 18 and 26 of total culture, whereas the non-treated population (black bar) was analyzed at days 0, 16 and 24 of culture. Indicated expression levels are relative to TBP. Bar represents the standard deviation (SD) of the mean of three independent experiments.

FIG. 3E is a flow cytometric analysis showing the proportion of $CD31^+$ $CD90^+$ and $EPCAM^+$ cells in monolayer populations derived from activin treated (day 26) and non-treated (day 24) endoderm. The $CD31^+$ and $CD90^+$ populations were significantly larger in non-treated compared to the treated cultures (CD31: 13.6+/−2.3% vs 0.49+/−0.11%, P<0.001; CD90: 41.2+/−4.7% vs 8.5+/−1.19%, P<0.001, Student's t-test, n=3). In contrast, a higher portion of $EPCAM^+$ cells was detected in the population derived from the activin-treated endoderm compared to the population generated from the non-treated cells (EPCAM: 90.7+/−2.7% vs 56.8+/−7.3%; P<0.01, n=3).

FIG. 3F shows immunostaining analyses showing the proportion of albumin positive cells in cultures generated from activin treated (day 26) and non-treated (day 24) endoderm. Albumin is visualized with Alexa 488. Scale bars: 200 µM.

FIG. 3G shows an Intracellular flow cytometric analyses indicating the proportion of albumin (ALB) and alpha-fetoprotein (AFP) cells in monolayer cultures generated from activin-treated (grey bars; day 26) and non-treated (black bars; day 24) endoderm. Bars in figures represent the standard deviation (SD) of the mean of three independent experiments. *P<0.05, P<0.01, *P<0.001 (Student's t-test; n=3). AL: adult liver, FL: fetal liver.

FIG. 4A is a phase-contrast image of hepatic aggregates at day 28 of culture. Scale bar, 200 nm.

FIG. 4B shows RT-qPCR based analyses of ALB, CPS1, TAT, G6P and TDO expression in monolayer (black bar) and 3D aggregate cultures (grey bar) at day 32 of differentiation. Values are determined relative to TBP and presented relative to expression in adult liver, which is set a one.

FIG. 4C is a RT-qPCR based analysis for CYP7A1, CYP3A7 and CYP3A4 expression at day 32 of differentiation in monolayer (black bar) and 3D aggregate culture (grey bar). Expression levels are relative to TBP.

FIG. 4D is a flow cytometric analysis showing the proportion of asialo-glycoprotein receptor-$1^+$ (ASGPR-1) cells in the monolayer (2D) and aggregate (3D) cultures at day 36. The frequency of ASGPR-$1^+$ cells was significantly higher in 3D aggregate cultures (2D: 28.8+/−3.1%, 3D: 64.7+/−4.26%, P<0.001, n=3). Bars in all graphs represent the standard deviation (SD) of the mean of samples from three independent experiments, *P<0.05, P<0.01, *P<0.001, Student's t-test, AL: adult liver, FL: fetal liver, PH; primary hepatocytes cultured for two days.

FIG. 5A is a RT-qPCR analysis of PGC1-a, HNF4a, AFP, ALB, G6P, and TAT expression in hepatic aggregates cultured in the presence and absence of 8-Br-cAMP. Expression levels are relative to TBP.

FIG. 5B is an intracellular flow cytometric analysis showing the proportion of alpha-fetoprotein (AFP)+ and albumin (ALB)+ cells (day 44) in hepatic aggregates cultured in the presence and absence of 8-Br-cAMP. The frequency of AFP+ cells was significantly lower in the population induced with cAMP compared to the non-induced population (34.5+/−12.4% vs 56.9+/−3.6%, P<0.05, mean+/−SD, n=3). The proportion of ALB positive cells, on the other hand, was higher in the cAMP-treated population (89.5+/−5.6% vs 82.3+/−3.0%, P<0.05 (mean+/−SD, n=3).

FIG. 5C is a RT-qPCR analysis of PGC1-a expression in cAMP treated pancreatic aggregates and hepatic aggregates generated from HES2, H9 and 38-2 cells. Values are determined relative to TBP and presented as fold change relative to expression in non-treated cells, which is set at one.

FIG. 5D shows ICG uptake at day 44 in non-treated and cAMP-treated aggregates. Bar in all graphs represent the standard deviation (SD) of the mean of the values from three independent experiments. *P<0.05, P<0.01, *P<0.001, Student's t-test, AL: adult liver, FL: fetal liver.

FIG. 6A shows expression of CYP3A7, CYP3A4, CYP1A2, CYP2B6 and UGT1A1 in hepatic aggregates (day 44) cultured in the presence and absence of 8-Br-cAMP. The levels in primary hepatocytes (PH) are shown as a control. Values are determined relative to TBP and presented as fold change relative to expression in non-treated cells, which is set at one.

FIG. 6B shows RT-qPCR analyses showing expression of PGC1a, TAT, HNF4a, CYP1A2 and CYP3A4 in untreated (−) and cAMP-treated (+) monolayer populations (day 44). Values are determined relative to TBP and presented as fold change relative to expression in non-treated cells, which is set at one.

FIG. 6C shows RT-qPCR analyses of CYP1A2 and ALB expression in cAMP treated aggregates (day 44) generated from non-treated (−Act) or extended activin treated (+Act) endoderm.

FIG. 6D shows RT-qPCR analyses of CYP1A2 expression in aggregates cultured for six (cAMP+/−) or 12 days in 8-Br-cAMP (cAMP+).

FIG. 6E shows that hESC-derived hepatic cells display CYP1A2 activity in vitro. Non-treated and cAMP-treated aggregates and primary hepatocytes were incubated with phenacetin (200 μM) for 24 hours. Generation of the O-de-ethylated metabolite acetaminophen from phenacetin was monitored by HPLC. Activity is presented per 10,000 cells. (*p<0.05, n=5).

FIG. 6F shows that hESC-derived hepatic cells display CYP2B6 activity in vitro. cAMP-treated aggregates and primary hepatocytes were incubated with bupropion (1 μM) for 48 hours. Formation of the metabolite O-hydroxy-bu-propion from bupropion was measured by HPLC. Activity is presented per 50,000 cells, (n=3).

FIG. 6G shows that metabolism of sulfamethazine (SMZ) to N-acetylated SMZ indicates the presence of the Phase II enzyme(s) NAT1 and/or NAT2. cAMP-treated aggregates and primary hepatocytes were cultured with SMZ (500 μM) for 48 hr, and N-acetylated SMZ was measured by HPLC. Activity is presented per 10,000 cells (n=3).

FIG. 6H is an HPLC analysis showing generation of 4-MU glucuronide (4-MUG) from 4-methylumbelliferone (4-MU) by the cAMP-treated aggregates indicative of Total UGT activity. cAMP-treated aggregates and primary hepatocytes were cultured with 4-MU for 48 hours. The formation of 4MUG was measured by HPLC. Activity is presented per 10,000 cells, (n=3). Bars in all graphs represent the standard deviation (SD) of the mean of samples from three independent experiments, *P<0.05, P<0.01, *P<0.001, Student's t-test, PH; primary hepatocytes.

FIG. 7A is a flow cytometric analysis showing the proportion of CXCR4+, CKIT+, EPCAM+, SOX17+ and FOXa2+ cells in activin/Wnt3a induced day six EBs generated from H9 hESCs, H1 hESCs and 38-2 iPSCs.

FIG. 7B shows RT-qPCR analyses of albumin expression in monolayer cultures generated from H9, H1 and 38-2-derived endoderm treated with activin for varying periods of time. The different populations were analyzed at the following times: no activin: day 24, 2 day activin: day 26, 4 day activin: day 28 of differentiation.

FIG. 7C shows intracellular flow cytometric analyses showing the frequency of ALB and AFP positive cells generated from the different hPSC lines (No activin (−): day 24, 2 day activin: day 26, 4 day activin: day 28 of differentiation).

FIG. 7D is a phase contrast image showing morphology of H9-derived hepatic cells at day 26 of culture. Scale bar: 200 m.

FIG. 7E shows RT-qPCR analyses showing CYP3A7, CYP3A4, CYP1A2, CYP2B6 and UGT1A1 in H9- and iPSC (38-2)-derived hepatic aggregates (day 44) cultured in the presence and absence of 8-Br-cAMP. Values are determined relative to TBP and presented as fold change relative to expression in non-treated cells, which is set at one. Bar in all graphs represents the standard deviation (SD) of the mean of the values from three independent experiments, *P<0.05, P<0.01, *P<0.001, Student's t-test, AL: adult liver, FL: fetal liver, PH: primary hepatocytes.

FIG. 8A depicts a flow cytometric analysis showing the proportion of CXCR4+, CKIT+ and EPCAM+ cells at day six of embryoid body induction with activin/wnt3a.

FIG. 8B depicts a flow cytometric analysis showing the proportion of CXCR4+, CKIT+ and EPCAM+ cells at day six of embryoid body induction with activin/CHIR 99021.

FIG. 8C depicts a flow cytometric analysis showing the proportion of CXCR4+, CKIT+ and EPCAM+ cells at day seven of monolayer induction with activin/wnt3a.

FIG. 8D depicts a flow cytometric analysis showing the proportion of CXCR4+, CKIT+ and EPCAM+ cells at day seven of monolayer induction with activin/CHIR 99021.

FIG. 8E is a photomicrograph of a H&E stained section of the intestinal mesentery showing a cluster of hESC-derived hepatocytes (arrowhead) two months following transplantation. Magnification was 5×. Intestine (arrow), engrafted cells (arrow heads)

FIG. 8F is a high magnification (10×) photomicrograph of an H&E stained section from FIG. 8E.

FIG. 8G is an immunohistochemical staining showing the presence of hESC-derived cells in the intestinal mesentery area two months following transplantation. Double staining for human Albumin (Alexa 488: green showing as an arrow and CK19 (Cy3: red) showing as an arrowhead shows that the transplanted cells have the potential to differentiate into the hepatocyte and cholangiocyte lineages. HESC-derived Hepatocyte-like cells were observed as Albumin positive cells (Arrow), whereas cholangiocyte like cells expressed CK19 and were found in duct like structures (Arrowhead).

FIG. 8H Immunohistochemical staining showing the presence of hESC-derived cells in the intestinal mesentery area two months following transplantation. Double staining for human Albumin (Alexa 488: green showing as an arrow and CK19 (Cy3: red) showing as an arrowhead shows that the transplanted cells have the potential to differentiate into the hepatocyte and cholangiocyte lineages. HESC-derived Hepatocyte-like cells were observed as Albumin positive cells (Arrow), whereas cholangiocyte like cells expressed CK19 and were found in duct like structures (Arrowhead).

FIG. 9A shows expansion of the hepatic progenitor population by Wnt signaling and Smad signaling. The fold increase in the number of ALB$^+$AFP$^+$ cells following 9 days of culture of H9-derived day 27 hepatic progenitors in different concentrations of CHIR99021 (0.3 μM, 1 μM and 3 μM) and TGFbeta inhibitor SB431542 (6 μM) is shown.

FIG. 9B depicts immunofluorescent staining showing the presence of ALB positive cells following 9 days (day 36) of culture of H9-derived day 27 hepatic progenitor cells.

FIG. 9C depicts immunofluorescent staining showing the presence of double positive ALB and HNF4a cells following 9 days (day 36) of culture of H9-derived day 27 hepatic progenitor cells.

FIGS. 9D and 9E show that inhibition of Wnt/p-catenin and MEK/Erk signaling increases expression of CYP3A4 (erkinhib+cAMP enough) and CYP1A2 in day 44 aggregates (all three). The Wnt inhibitor XAV939 (1 μM) and the MEK/Erk inhibitor PD0325901 (1 μM) were added alone or together to the aggregate cultures at day 30 of differentiation together with 8-Br-cAMP.

FIG. 9D shows the expression of CYP3A4 relative to the levels found in adult liver. Addition of the MEK/ErK inhibitor together with cAMP induced levels of CYP3A4 expression comparable to those found in the adult liver.

FIG. 9E shows the expression of CYP1A2 relative to the levels found in adult liver. Addition of both the Wnt and MEK/ErK inhibitors with cAMP induced the highest levels of CYP1A2 expression.

FIG. 9F shows expression of ALB in day 26 hepatocyte-like cells culture on different extra cellular matrix (ECM). Values shown are relative to cells cultured on gelatin, which is set to 1.

FIG. 10A shows high magnification (20×) photomicrographs of H&E stained sections from three-dimensional (3D) tissue generated in a collagen/Matrigel matrix. H9-derived day 25 hepatic progenitor cells were mixed (aggregated) with OP9-delta 1 stromal cells at a ratio of 5:1, in low cluster culture dishes for 48 hours. The chimeric aggregates were embedded in a mixture of type 1 collagen (80%) and Matrigel (20%) to establish a 3D co-culture. The culture was maintained in media containing the HGF 20 ng/ml and EGF 50 ng/ml and in the presence or absence of GSI for 9 days. The aggregate morphology was maintained in cultures treated with GSI. These aggregates contained hepatocyte-like cells that express albumin. In the absence of GSI, the aggregates developed extensive branched structures. The cell within the branches displayed an epithelial morphology and were organized around an inner lumen. These cells expressed CK19, suggesting that they were cholangiocytes and that the branched structures may represent developing bile ducts.

FIG. 10B shows that activation of Notch signaling upregulates expression of CK19 and the cystic fibrosis transmembrane conductance regulator (CFTR) in the ductal structures. Values shown are relative to cells cultured in the presence of GSI. The cells in the Notch (−) co-culture (i.e., treated with GSI) retained the characteristics of hepatocytes as demonstrated by the expression of Albumin.

FIG. 10OC shows that the expression of CFTR in 3D co-culture were higher induced than those found in monolayer culture. Values shows are relative to cells cultured in the monolayer condition.

FIG. 11A is a schematic of monolayer cultures to generate definitive endoderm were also generated in the presence of Activin together with wnt3a or CHIR 99021. Endoderm cells at day 5 in monolayer induction are equivalent to the cells at day 6 in the EBs. Additional activin treatment beyond day 5 is also necessary in the monolayer the cultures for the generation of hepatic progenitor cells and mature hepatocytes.

FIG. 11B is a schematic representation of EB cultures used to generate definitive endoderm.

FIG. 11C is a schematic representation of the protocol used to generate cholangiocytes. Definitive endoderm generated in monolayer cultures was specified to a hepatic fate resulting in the generation of hepatic progenitors (hepatoblasts) by day 25 of culture. The hepatic progenitor cells were dissociated and aggregated with OP9/OP9 delta cells in low cluster dishes for two days. The chimeric aggregates were embedded in a Collagen/Matrigel gel and cultured in the medium supplemented with HGF (20 ng/ml) and EGF (50 ng/ml) in the presence or absence of the inhibitor of pan Notch signaling (e.g. notch antagonist), gamma-secretase inhibitor (GSI) L-685,458.

FIG. 12A is a schematic representation of the protocol used for the generation of chimeric aggregates consisting of hESCs-derived endothelial cells (RFP-positive) and hepatoblasts. RFP(+)/CD34(+) endothelial cells were generated by induction of EBs with BMP4 for 4 days and then with VEGF and bFGF for an additional 2 days. FACS isolated RFP(+)/CD34(+) endothelial cells were plated on collagen type I coated wells and cultured with EGM-2 medium in the presence of VEGF and bFGF for 6 days. To generate the chimeric aggregates, the cultured RFP(+)/CD34(+) cells were trypsinized, dissociated and placed into Aggrewell plates at a cell density of 100 cells per well. Following 2 days of culture, the day 25 hepatoblasts cells were placed onto the RFP(+)/CD34(+) endothelial aggregates at a cell density of 1000 cells per well. Scale bar 100 μm.

FIG. 12B shows phase contrast and fluorescent images showing RFP positive cells within endothelial/hepatic aggregates at day 33. RFP is not detected in hepatic aggregates generated without the endothelial cells. Scale bar 100 μm.

FIG. 12C is a flow cytometric analysis showing the proportion of RFP positive cells in endothelial/hepatocyte aggregates at day 33.

FIG. 12D is an RT-qPCR analyses showing CYP3A4 expression in the aggregates with and without endothelial cells at day 44. Values are determined relative to TBP and presented as fold change relative to expression of the adult liver sample, which is set at one.

FIG. 14A is a schematic representation of the differentiation protocol.

FIG. 14B depicts flow cytometric analyses showing the development of the CXCR4+, CKIT+, and EPCAM+ populations at day 7 in the monolayer induction format.

FIG. 14C is an RT-qPCR showing expression of indicated genes in H9-derived hepatoblast cells maintained in the culture conditions indicated FIG. 14A. The expression of the indicated genes was analyzed on days 7, 13, 19 and 25 of culture. Values are determined relative to TBP and presented as fold change relative to expression in fetal liver, which is set at one. AL: Adult liver, FL: fetal liver.

FIG. 17A shows a duct structure in a mammary fat pad in a low magnification image from a histological analyses of a cholangiocyte graft in a Matrigel plug 8 weeks following transplantation of day 25 hepatoblast-derived cells cocultured with OP9 stromal cells for 9 days in media containing of HGF, EGF and TGFβ1. Following co-culture, the cells were dissociated and transplanted (10e per recipient) into the mammary fat pad of immunodeficient NOD/SCID/IL2rg −/− (NSG) mice.

FIG. 17B is a high magnification image showing multiple duct structures in a in mammary fat pad as described in FIG. 17A (H&E staining).

FIG. 17C is a low magnification image showing immunostaining to detect RFP-positive cells in hESC-derived ductal structures that developed in the mammary fat pad following transplantation. For these studies cholangiocytes were generated from HES2-RFP hESCs that express RFP from the ROSA locus. Cholangiocytes generated following 9 days of co-culture with OP9 stromal cells were transplanted into the mammary fat pad of NSG mice. Grafts that developed 8 weeks following transplantation were analyzed for the presence of RFP+ cell by immunohistochemistry. RFP-positive cells were detected within all the ductal structures, confirming that the cells were of human origin and derived from the HES2-RFP cells. RFP+ structures were visible in the image.

FIG. 17D is a high magnification image showing immunostaining to detect RFP-positive cells in hESC-derived ductal structures that developed in the mammary fat pad following transplantation. For these studies cholangiocytes were generated from HES2-RFP hESCs that express RFP from the ROSA locus. Cholangiocytes generated following 9 days of co-culture with OP9 stromal cells were transplanted into the mammary fat pad of NSG mice. Grafts that developed 8 weeks following transplantation were analyzed for the presence of RFP+ cell by immunohistochemistry. RFP-positive cells were detected within all the ductal structures, confirming that the cells were of human origin and derived from the HES2-RFP cells. RFP+ structures were visible in the image.

FIG. 18A shows representative confocal microscopy images of calcein-green-labeled and forskolin/IBMX (F/I) stimulated cyst structures generated from H9 (hESC)- and Y2-1 (iPSC)-derived cholangiocytes. Image was taken 24 hours after F/I stimulation. Scale bar 500 μm.

FIG. 18B shows quantification of the degree of cyst swelling 24 hours after F/I stimulation in the presence or absence of CFTR inhibitor. F/I stimulated cyst swelling was quantified using velocity imaging software. The total size of the cysts is normalized to that prior to F/I stimulation. Values are from three individual experiments.

*P<0.05, P<0.01, *P<0.001 (Student's t-test; n=3).

Figure 19A:
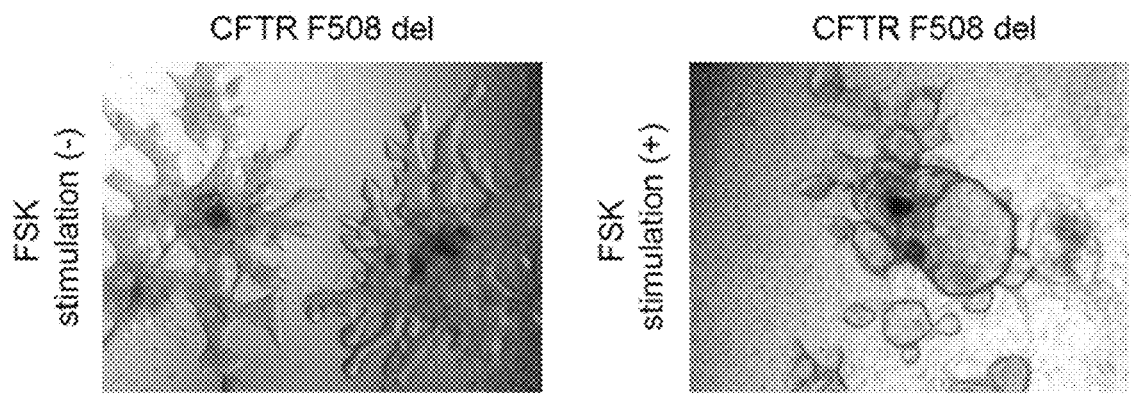
Figure 19B:
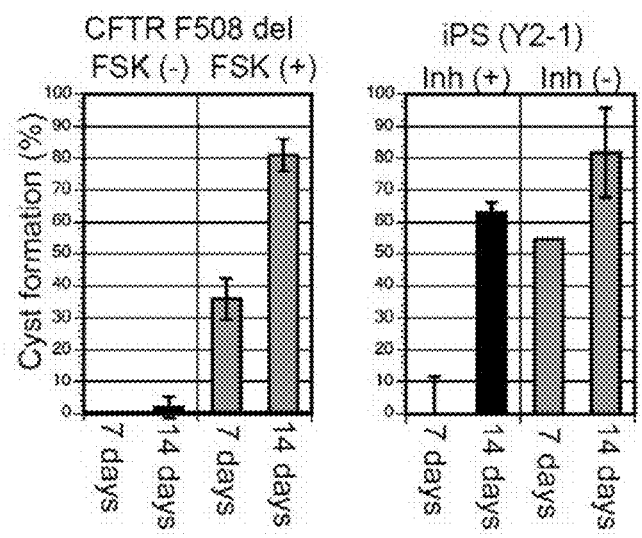

FIGS. 19A-19B demonstrate the generation of cholangiocytes from cystic fibrosis patient iPSCs.

FIG. 19A shows phase contrast images of cholangiocyte like cells derived from CFTR deleted F508 iPS cells (CF-iPSCs) at day 44 of 3D gel culture in the presence or absence of forskolin. CF-iPSCs-derived hepatoblasts and chimeric hepatoblast/OP9 aggregates were generated using the protocol shown in FIG. 14A. After embedding in collagen/Matrigel culture, cyst formation was induced from the aggregates by the addition of forskolin for the first week of the two-week culture period (left). Without forskolin stimulation, the CF-iPSCs derived cholangiocytes formed branched ductal structure rather than hollow cysts (right).

FIG. 19B shows the quantification of numbers of cyst structures that developed from CF-iPSCs and normal iPSC (Y2-1)-derived cholangiocytes at 7 and 14 days of culture. CF-iPSCs derived cholangiocytes were maintained in the 3D gel conditions in the presence or absence of forskolin for the first week of the two weeks culture period (left graph). Normal iPS cells-derived cholangiocytes were maintained in the presence or absence of CFTR inhibitor for the first week of the two-week culture periods (right graph). Addition of forskolin increased the number of cyst structures that developed from the CF-iPSCs derived cholangiocytes at both 7 and 14 days of culture (left graph). Addition of the CFTR inhibitor to normal iPSC-derived cholangiocytes delayed cyst formation (right graph).

Figure 19C:
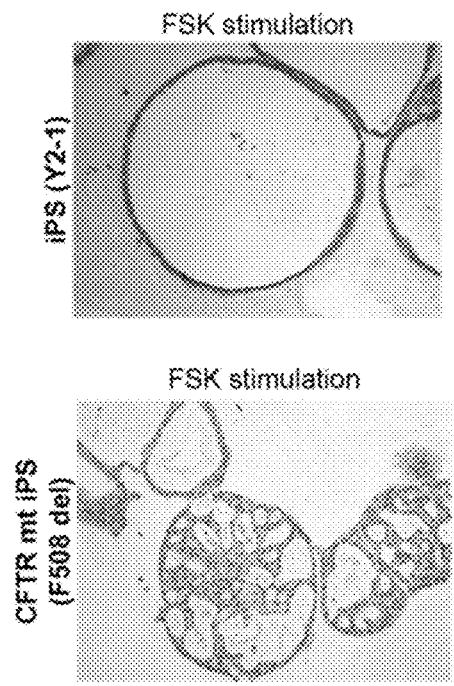

FIG. 19C shows histological analyses of cysts derived from normal iPSC-(upper panel) and CF-iPSC-(lower panel) cholangiocytes at day 44. Both cholangiocyte populations were cultured in the presence of forskolin for the first week of the two weeks culture. Addition of forskolin to the normal iPSC-derived cholangiocytes induced the formation of large hollow cysts (upper panel). The CF-iPSC-derived cysts were smaller, often containing internal septum (lower panel).

Figure 20A:
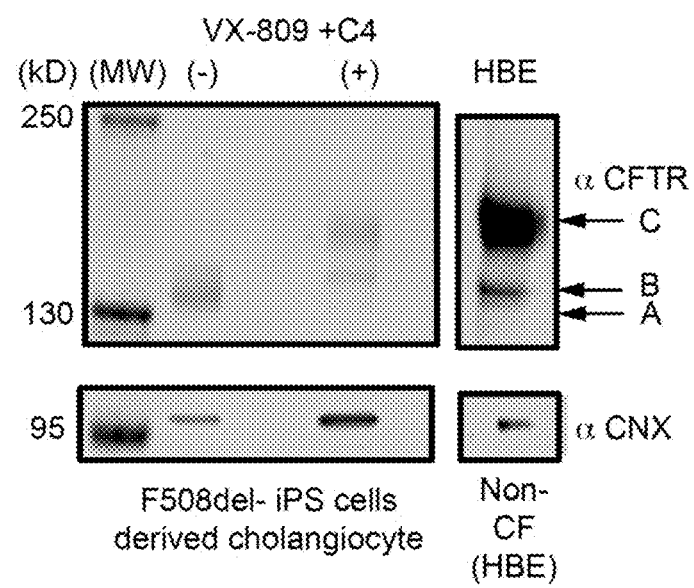

FIG. 20A shows restoration of CFTR function in the CF-iPSC-derived cholangiocytes by treatment with the small molecule correctors VX-809 and C4. Western blot analysis shows the accumulation of mature complex glycosylated form of CFTR (band C) in CF-iPSC-derived cholangiocytes treated with VX-809 and C4. The mutant form of the protein (band B) was predominant in the uncorrected cells. Human bronchial epithelial cells (HBE) were used as a positive control.

Figure 20B:
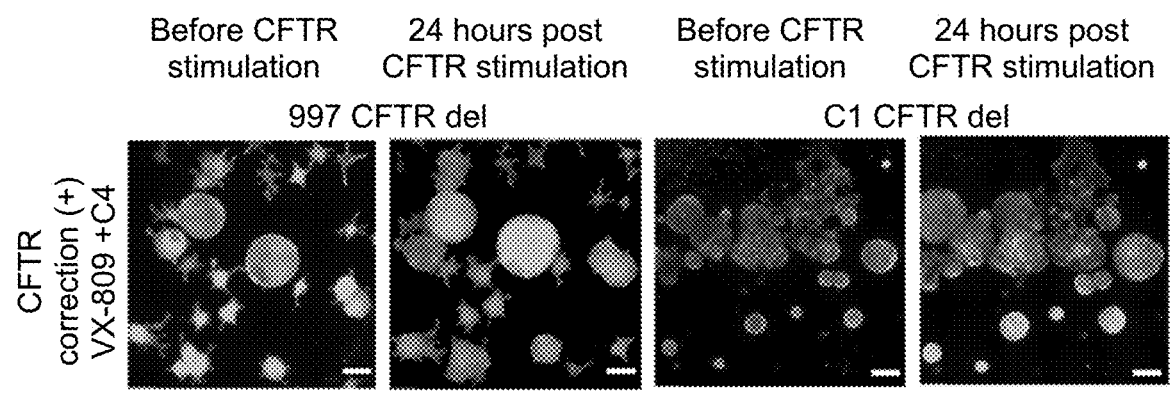

FIG. 20B shows representative confocal microscopy images of calcein-green-labeled and forskolin/IBMX (F/I) stimulated cyst structures generated from CF-iPSCs from two individual patients (997 CFTR del and C1 CFTR del—both of which carry the deltaF508 mutation). Images were taken 24 hours after F/I stimulation. Scale bar 500 μm.

Figure 20C:
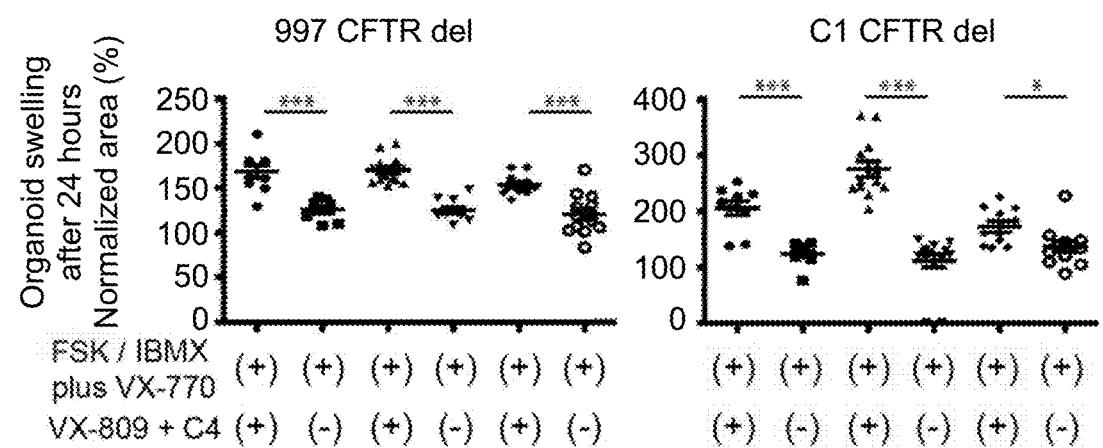

FIG. 20C shows quantification of the degree of swelling observed in hPSCs-cysts 24 hours following F/I stimulation in the presence or absence of CFTR inhibitor. F/I stimulated cyst swelling was quantified using velocity imaging software. The total size of cyst is normalized to that before F/I stimulation from each of three individual experiments. *P<0.05, , P<0.01, *P<0.001 (Student's t-test; n=3).

Figure 21:
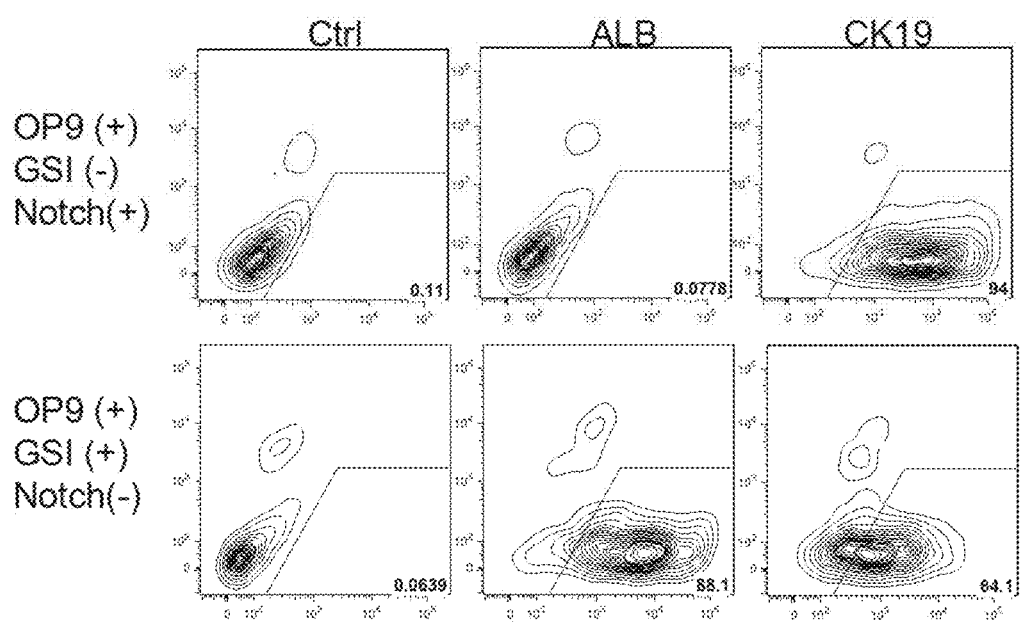

FIG. 21. Intracellular flow cytometric analysis showing the proportion of ALB$^+$ and CK19$^+$ cells in the hepatoblast-derived population following 9 days of coculture with OP9. Cells were cultured in media containing of HGF, EGF and TGFβ1 in the presence or absence of GSI. Ctrl shows isotype control.

Figure 14A:
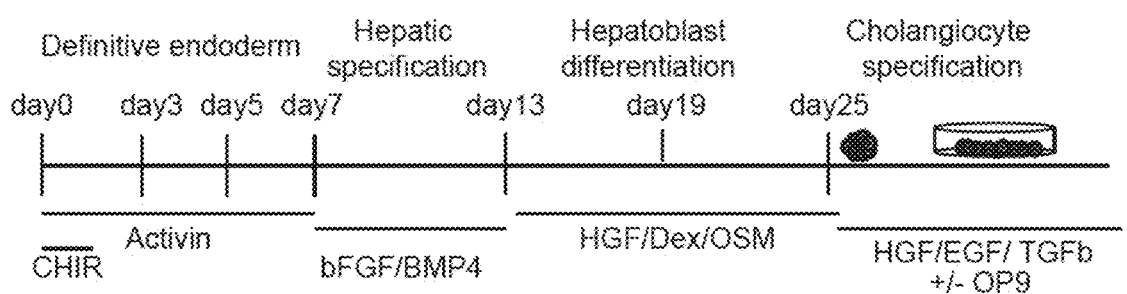
FIGS. 14A-14C characterize the hepatoblast stage of development in hPSC differentiation cultures.
Figure 22:
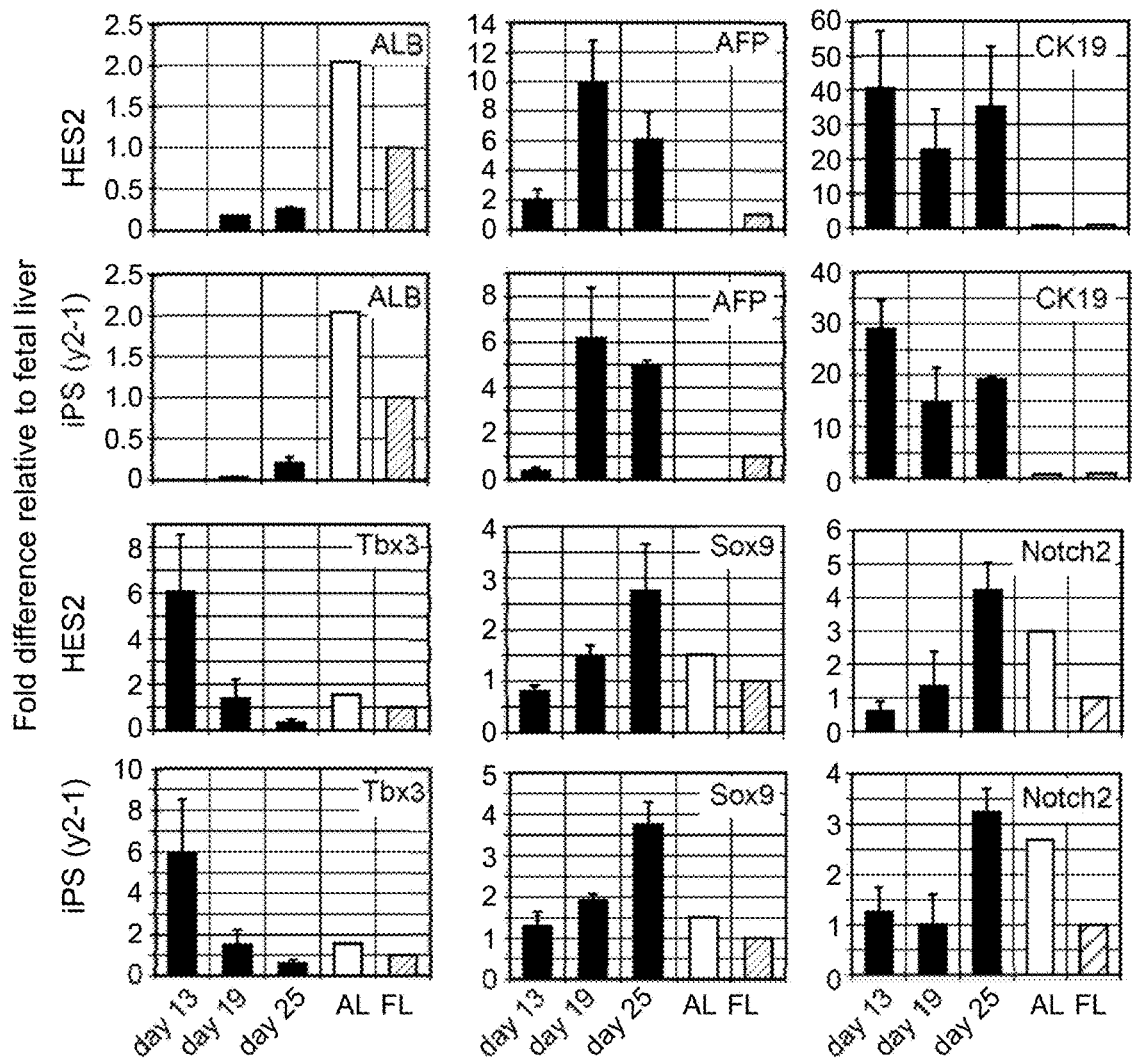

FIG. 22. Hepatic specification and differentiation of hepatoblast from other hPSCs. RT-qPCR analyses showing expression of indicated genes in HES2 and Y2-1 iPS cell-derived hepatoblast cells maintained as indicated in FIG. 14A. The expression of the indicated genes was analyzed on days 7, 13, 19 and 25 of culture. Values are determined relative to TBP and presented as fold change relative to expression in fetal liver, which is set at one. AL: Adult liver, FL: fetal liver.

FIGS. 23A-23E show 3D gels used for the generation of cystic structures from hPSC-derived cholangiocytes.

Figure 23A:
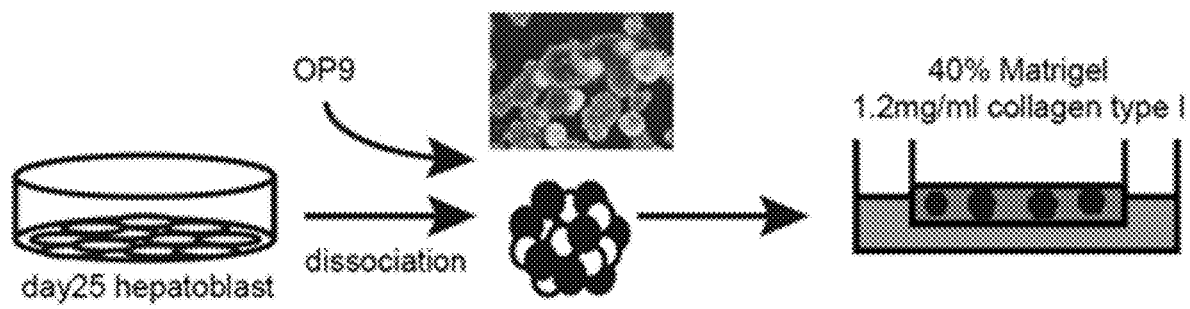

FIG. 23A. Schematic representation of the differentiation protocol used to generate chimeric aggregates consisting of day 25 hPSCs derived hepatoblasts and OP9 cells (GFP+). Day 25 hepatoblasts were dissociated and co-cultured with OP9 cells at the ratio of 4:1, in low cluster culture dishes. The chimeric aggregates were embedded in gel consisting of a mixture of type 1 collagen (1.2 mg/ml) and Matrigel (20%).

Figure 23B:
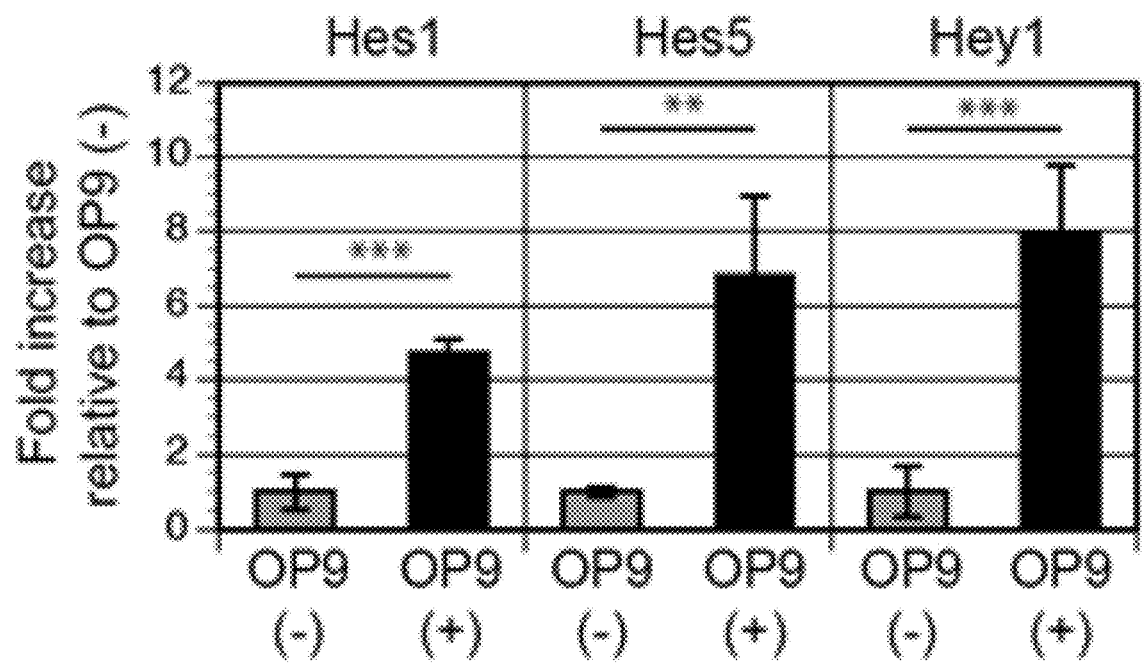

FIG. 23B. RT-qPCR based expression analyses of structures that developed in the gel in the presence or absence of OP9 at day 44 of culture in media containing HGF, EGF and TGFβ1. Expression of the Notch target genes was significantly upregulated in the presence of OP9. Values are determined relative to TBP and presented as fold change relative to expression in the cell cultured in the absence of OP9, which is set at one.

Figure 23C:
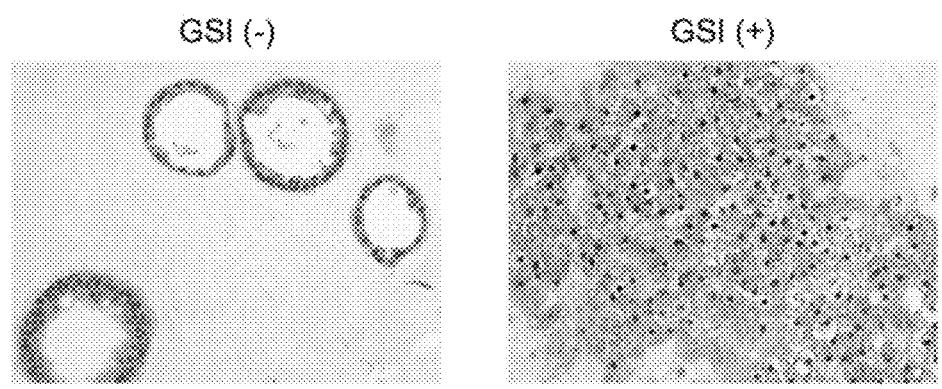

FIG. 23C. Histological analyses of cyst structures that developed from H9 derived cholangiocytes cultured with OP9 cells in the presence (right panel) or absence (left) of GSI at day 44 culture (H&E staining).

Figure 23D:
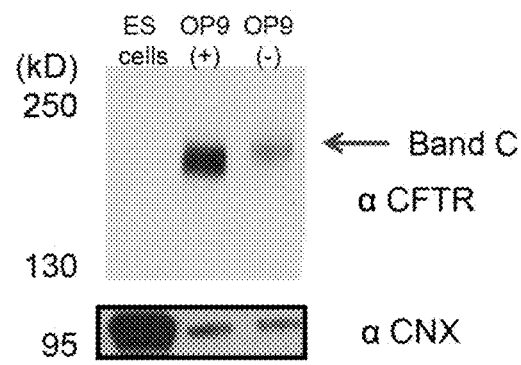

FIG. 23D. Western blot analysis showing the presence of the mature complex glycosylated form of CFTR protein (Band C) in structures generated from normal iPSC-derived cholangiocytes cultured in the presence or absence of OP9. Undifferentiated normal iPSCs were used as negative control.

Figure 23E:
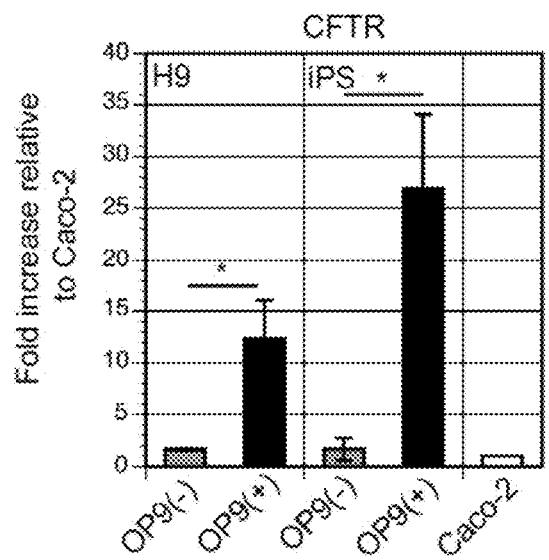

FIG. 23E. RT-qPCR based expression analyses of CFTR in structures generated from normal iPSC-derived cholangiocytes cultured in the presence or absence of OP9. Cells were analysed at day 44 of culture. Values are determined relative to TBP and presented as fold change relative to expression value detected in caco-2 cells (intestinal colon carcinoma cell line), which set as one. *P<0.05, P<0.01, *P<0.001 (Student's t-test; n=3).

Figure 24A:
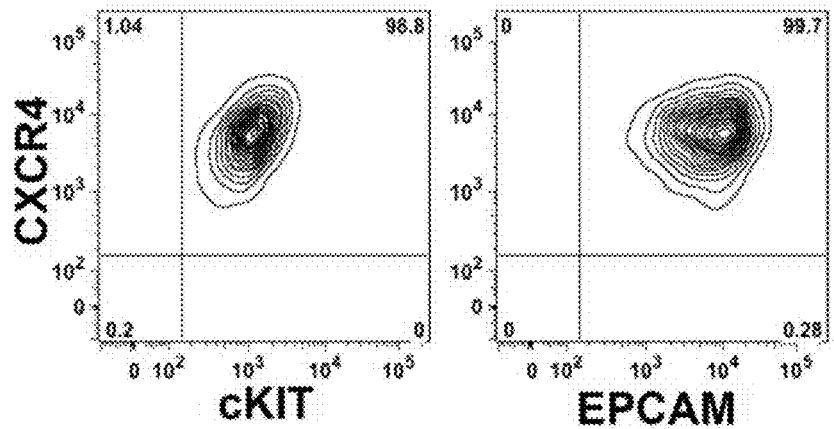

FIG. 24A. Generation of definitive endoderm and hepatoblasts from cystic fibrosis patient iPSCs. Flow cytometric analyses showing the development of the CXCR4$^+$, CKIT$^+$, and EPCAM populations from CF-iPS cells (C1 del CFTR) at day 7 of monolayer culture.

Figure 24B:
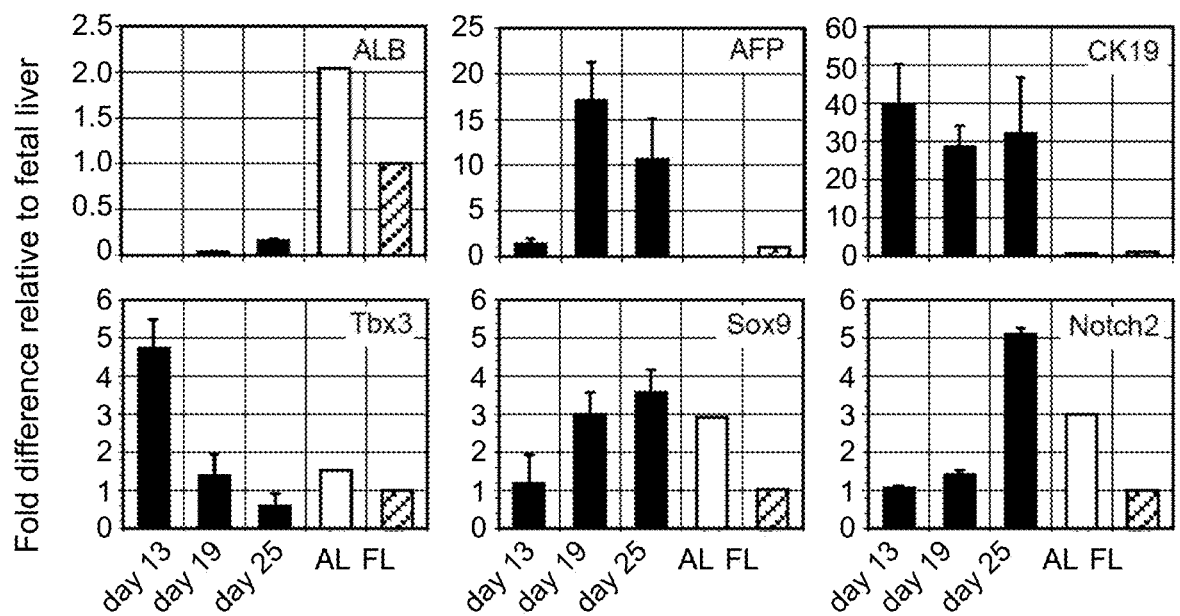

FIG. 24B is an RT-qPCR analyses showing expression of indicated genes in the CF-iPSC-derived hepatoblast population maintained in the culture conditions outlined FIG. 14A. The expression of indicated gene was analyzed on days 7, 13, 19 and day 25 of culture. Values are determined relative to TBP and presented as fold change relative to expression in fetal liver, which is set at one. AL: Adult liver, FL: fetal liver.

DETAILED DESCRIPTION OF THE DISCLOSURE

Described herein is a robust and reliable platform for the efficient generation of hepatocytes and cholangiocytes from pluripotent stem cells (PSCs) through a series of steps described herein and for the generation of metabolically functional hepatocytes and/or cholangiocytes. It is demonstrated for example that one or more of extended nodal (e.g. activin) signaling treatment, inducing aggregation and activating cAMP signaling for example in combination with FGF agonist induction and BMP4 agonist induction optionally in combination with one or more steps that increases expansion of a particular cell population and/or specific fate permits the reproducible generation of hepatocyte and cholangiocyte lineage cells including for example expanded hepatoblasts and/or with further manipulation, functional and mature hepatocytes and cholangiocytes from definitive endoderm induced in embryoid bodies or from monolayers.

An aspect of the present disclosure includes a method of producing hepatocyte or cholangiocyte lineage cells such as hepatoblasts, hepatocytes and/or cholangiocytes from an extended nodal agonist treated induced endodermal cell population, the method comprising: (a) specifying the extended nodal agonist treated induced endodermal cell population to obtain a cell population comprising hepatocyte and/or cholangiocyte progenitors by contacting the extended nodal agonist treated induced endodermal cell population with specification media comprising a combination of a FGF agonist and a BMP4 agonist and/or active conjugates and/or fragments thereof to obtain a cell population comprising hepatocyte and/or cholangiocyte progenitor, and (b) inducing maturation, further lineage specification and/or expansion of the hepatocyte and/or cholangiocyte progenitors of the cell population to obtain an expanded population of hepatocytes and/or a population comprising hepatocytes and/or cholangiocytes, the inducing maturation step comprising generating aggregates of the cell population.

Aggregation is demonstrated herein to be important for and to promote maturation.

In an embodiment, the hepatocyte and/or cholangiocyte progenitors comprise hepatoblasts and/or immature hepatocytes and/or immature cholangiocytes.

The term "contacting" (e.g. contacting an endodermal cell population with a component or components) is intended to include incubating the component(s) and the cell together in vitro (e.g., adding the compound to cells in culture) and the step of contacting can be conducted in any suitable manner. For example, the cells may be treated in adherent culture, or in suspension culture, the components can be added temporally substantially simultaneously (e.g. together in a cocktail) or sequentially (e.g. within 1 hour, 1 day or more from an addition of a first component). The cells can also be contacted with another agent such as a growth factor or other differentiation agent or environments to stabilize the cells, or to differentiate the cells further and include culturing the cells under conditions known in the art for example for culturing the pluripotent (and/or differentiated) population for example as further described in the Examples.

The terms "endoderm" and "definitive endoderm" as used herein refer to one of the three primary germ cell layers in the very early embryo (the other two germ cell layers are the mesoderm and ectoderm). The endoderm is the innermost of the three layers. An endoderm cell differentiates to give rise first to the embryonic gut and then to derivative tissues including esophagus, stomach, intestine, rectum, colon, pharyngeal pouch derivatives tonsils, thyroid, thymus, parathyroid glands, lung, liver, gall bladder and pancreas.

Figure 1A:
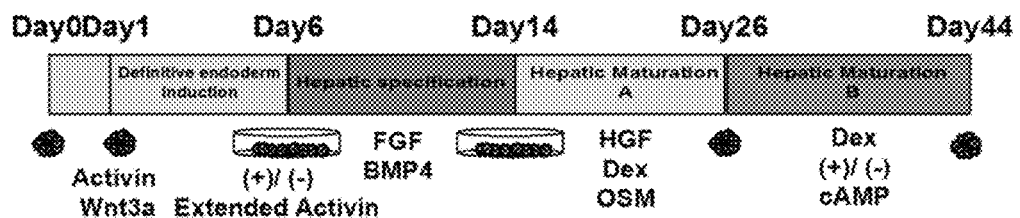
FIGS. 1A-1F show endoderm induction in hESC-derived embryoid bodies.

The "induced endodermal cell population" as used herein refers to a population of endoderm cells corresponding to "definitive endoderm induction" stage for example as shown in FIG. 1A. This population can be for example prepared from embryoid bodies (EB) that have been exposed to a nodal agonist, such as activin, or optionally from EB that have been exposed to a nodal agonist and a wnt/beta-catenin agonist such as Wnt3a or a GSK-3 selective inhibitor such as CHIR-99021 (Stemolecule™ CHIR99021 Stemgent), 6-bromo-Indirubin-3'-Oxime (BIO) (Cayman Chemical (cat: 13123)), or Stemolecule™ BIO from Stemgent (cat: 04003). Alternatively, the induced endodermal cell population can be prepared from cells grown in a monolayer. The induced endodermal cell population can for example be identified by flow cytometric and molecular analysis for one or more markers such as surface markers CXCR4, CKIT and EPCAM and the transcription factors SOX17 and FOXA2. The induced endodermal cell population can also for example be identified by at least or greater than 70, 80, 90 or 95% of the population co-expressing CXCR4 and CKIT or CXCR4 and EPCAM. The induced endodermal cell population can also for example be identified by greater than 70, 80, 90 or 95% of the population of the population expressing SOX17 and/or FOXA2. The induced endodermal cell population can for example be in a 2D (monolayer) or 3D (Embryoid Body or other form of aggregates) format. The induced endodermal population can be derived for example from hESCs as well as an induced pluripotent cell (iPSC) as demonstrated in Example 1.

The induced endoderm cell population is for example treated with a nodal agonist extended period of time to provide an extended nodal agonist treated induced endoderm cell population.

Figure 3A:
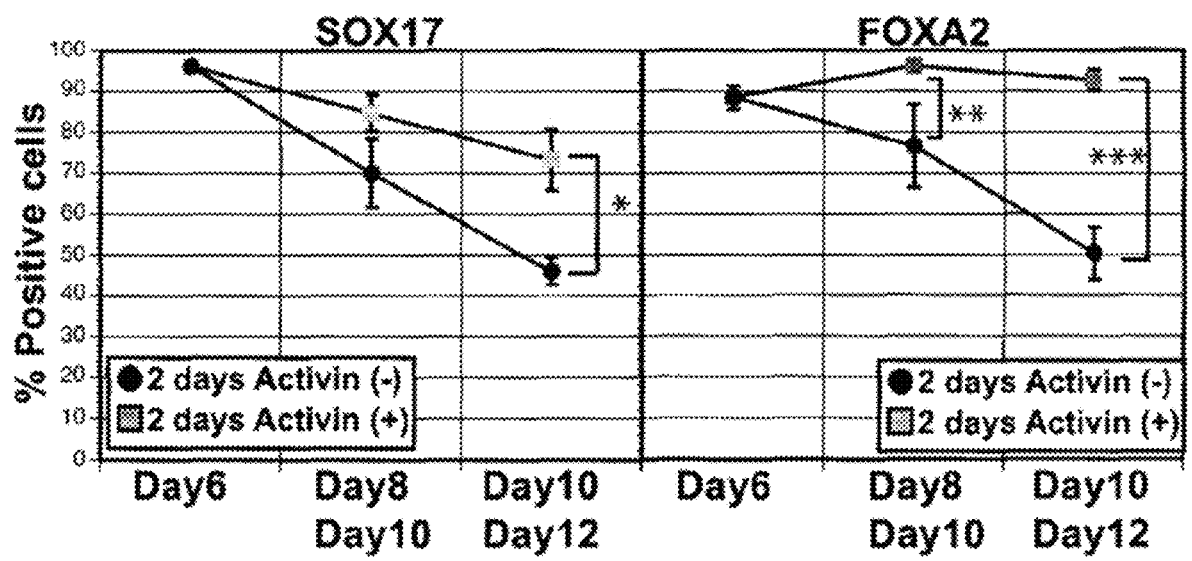
FIGS. 3A-3G show that the duration of activin signaling affects hepatic development.

As described in Example 1 and shown in FIG. 3A, culturing day 6 cells (day 5 when the method comprises monolayer induction) for two additional days in activin prior to specifying with FGF/BMP4 results in a higher proportion of SOX17' FOXA2$^+$ cells as measured at day 12 compared to cells not cultured for two additional days in activin (e.g. an example of a nodal agonist). This step is also referred to herein as an "extended activin" treatment and is an example of an "extended nodal agonist" treatment.

Figure 3B:
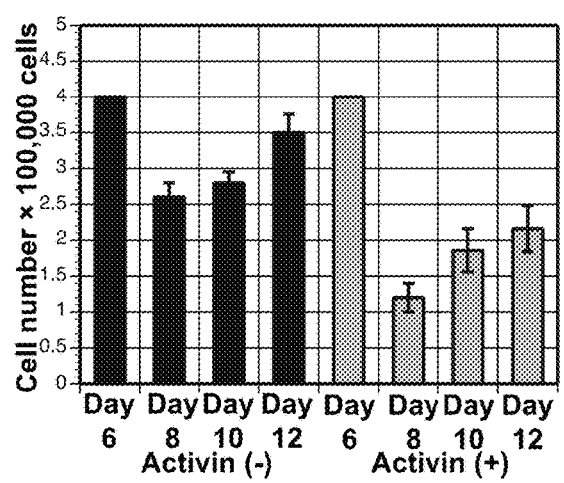
Figure 3C:
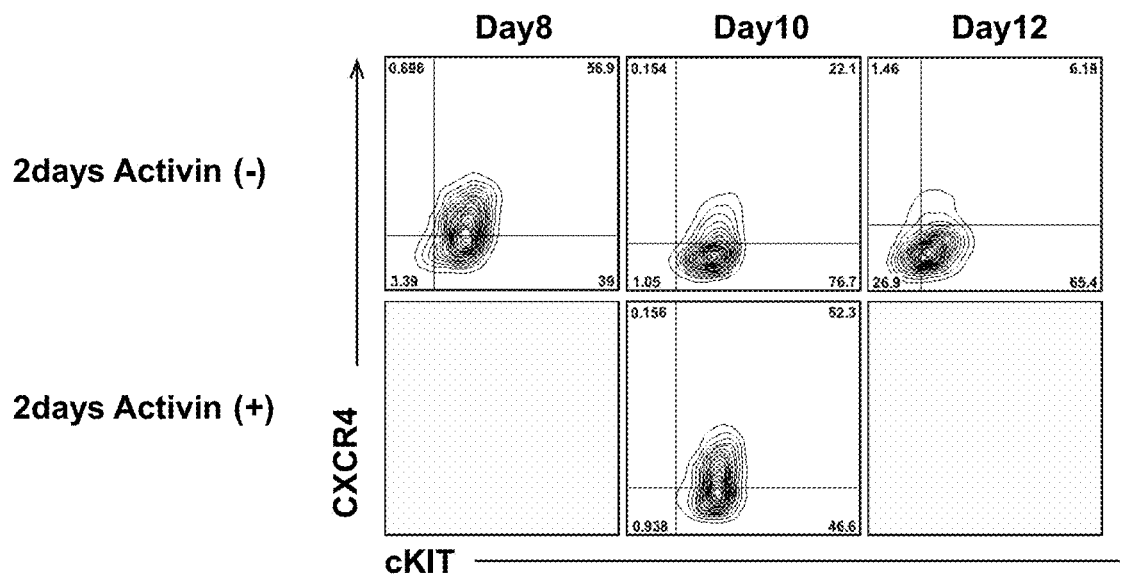
Figure 3D:
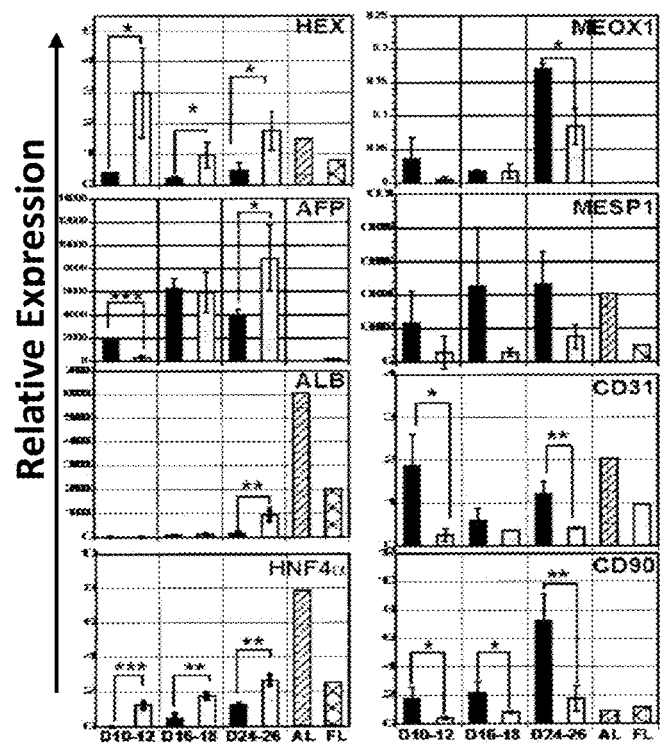
Figure 3:
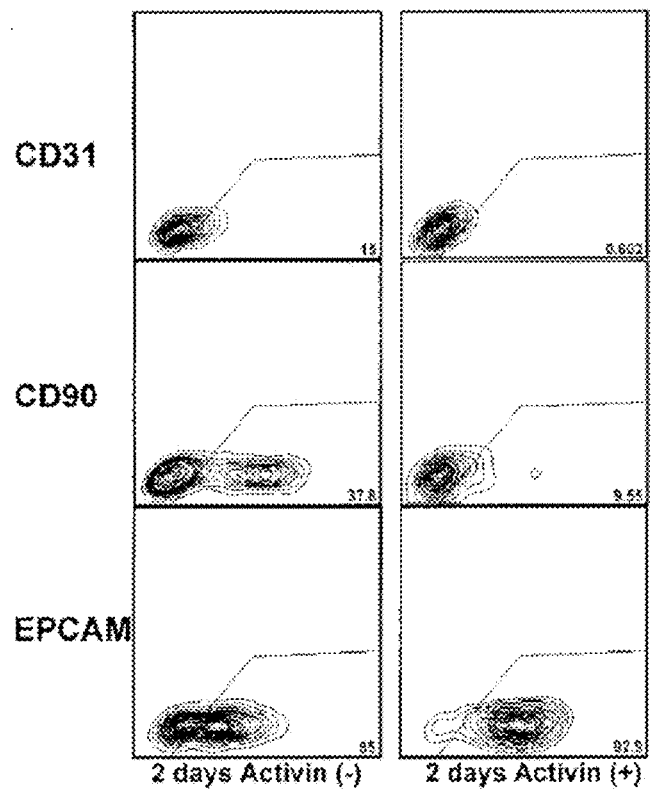

The "extended nodal agonist treated induced endoderm cell population" as used herein refers to an induced endodermal cell population that has been treated with a nodal agonist such as activin for an extended period, for example from about 1 to about 4 or about 1, 2, 3 or 4 additional days (e.g. "the extended period" which is in addition to the endoderm induction phase which can comprise treatment with a nodal agonist). The extended nodal agonist treatment as demonstrated herein resulted in higher levels of expression of genes indicative of hepatic progenitor (hepatoblast) development, including HEX, AFP, ALB and HNF4a at day 26 of culture (as shown in FIG. 3D). The extended nodal agonist treated induced endoderm population is obtained by inducing endoderm cells in embryoid bodies (EBs) or by inducing endoderm cells that are in a monolayer, and wherein the induced endodermal population is cultured in the presence of a nodal agonist, for example activin, for an extended period to produce an extended nodal agonist treated induced endodermal population.

The extended nodal agonist treated induced endodermal cell population is, in an embodiment, obtained by inducing endoderm cells in embryoid bodies (EBs). In another embodiment, the extended nodal agonist treated induced endodermal population is obtaining by inducing endoderm cells that are in a monolayer. In each case, the induced endodermal population is cultured in the presence of a nodal agonist, for example activin, for an extended period.

Optionally, the induced endodermal population is subsequently dissociated, for example in embodiments where the induced endodermal cell population is derived from EBs. As used herein, "dissociated cells" or "dissociated cell populations" refers to cells that are not in 3D aggregates, for example, physically separated from one another. Dissociated cells are distinguished from "cell aggregates" which refers to clusters or clumps of cells.

In an embodiment, the induced endodermal population comprises at least 80%, 85%, 90% CXCR4$^+$ and cKIT$^+$ positive cells and/or at least 70%, 75%, 80% SOX17$^+$ cells.

In some embodiments, the induced endodermal cell population (and/or the extended nodal agonist treated induced endodermal cell population) is produced from pluripotent stem cells (PSCs) such as embryonic stem cells (ESCs) or induced pluripotent stem cells (iPSCs). The pluripotent stem cells are optionally human ESCs (hESCs) or human iPSCs (hiPSCs).

The term "pluripotent" as used herein refers to a cell with the capacity, under different conditions, to differentiate to more than one differentiated cell type, and for example the capacity to differentiate to cell types characteristic of the three germ cell layers. Pluripotent cells are characterized by their ability to differentiate to more than one cell type using, for example, a nude mouse teratoma formation assay. Pluripotency is also evidenced by the expression of embryonic stem (ES) cell marker.

The term "progenitor cell" refers to cells that have a cellular phenotype that is at an earlier step along a developmental pathway or progression than a fully differentiated cell relative to a cell which it can give rise to by differentiation. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation, self-renewal and giving rise to more progenitor cells having the ability to generate a large number of mother cells that can in turn give rise to differentiated, or differentiable, daughter cells. The daughter cells can for example be induced to proliferate and produce progeny that subsequently differentiate into one or more mature cell types, while also retaining one or more cells with parental developmental potential.

The term "embryonic stem cell" is used to refer to the pluripotent stem cells of the inner cell mass of the embryonic blastocyst (see, for example, U.S. Pat. Nos. 5,843,780, 6,200,806). Such cells can also be obtained from the inner cell mass of blastocysts derived from somatic cell nuclear transfer (see, for example, U.S. Pat. Nos. 5,945,577, 5,994, 619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

In one embodiment, the method of producing hepatocytes and/or cholangiocytes from an extended nodal agonist treated induced endodermal cell population comprises: (a) specifying the extended nodal agonist treated endodermal cell population to a cell population comprising hepatocyte and/or cholangiocyte progenitors by contacting the induced endodermal cell population with specification media comprising a FGF agonist and a BMP4 agonist and/or active conjugates and/or fragments thereof.

In an embodiment, the specifying step comprises contacting an extended nodal agonist treated induced endodermal population with specification media comprising a FGF agonist and BMP4. The FGF agonist can for example be bFGF, FGF10, FGF2 or FGF4, active fragments and/or combinations thereof. The combinations can be added to the cells for example sequentially.

In an embodiment, the specifying step comprises first contacting an extended noda) agonist treated induced endodermal population with specification media comprising FGF10 and BMP4 for about 40 to about 60 hours for example about 40, 42, 44, 46, 48, 50, 52, 54, 56, 58 or about 60 hours and then contacting the extended nodal agonist treated induced endodermal population with specification media comprising bFGF and BMP4 for about 4 to about 7 days, for example about 4, 5, 6 or about 7 days.

In one embodiment, the specification media comprises Iscove's Modified Dulbecco's Medium (IMDM) supplement with 1% vol/vol B27 supplement (Invitrogen: A11576SA), ascorbic acid, TG, FGF10 (50 ng/ml) (for example from day 8 to day 10, bFGF (20 ng/ml) (for example from day 10 to day 14), and BMP4 (50 ng/ml).

Optionally, the endodermal cell population is contacted with FGF10 and BMP4 for 1 to 3 days, optionally 2 days and subsequently contacted with bFGF and BMP4 for 2 to 6 days, optionally 3 to 5 days, optionally 4 days. In some embodiments, the endodermal cell population is incubated in cell culture medium comprising BP4 and FGF10 or bFGF. Optionally, the endodermal cell population is incubated in cell culture medium comprising Iscove's Modified Dulbecco's Medium (IMDM) supplemented with 1% vol/vol B27, ascorbic acid, monothioglycerol, BMP4 and FGF10 or bFGF.

In some embodiments, the endodermal cell population is dissociated and the monolayer cells are then contacted with FGF and a BMP4 agonist.

In other embodiments, the monolayer cells are contacted with activin for 1 to 4 days, optionally 1, 2, 3 or 4 days prior to being contacted with FGF and a BMP4 agonist such as BMP4. Optionally, the monolayer cells are incubated in cell culture medium comprising activin A, optionally medium comprising StemPRO-34 supplemented with bFGF, activin A and BMP4.

In a further embodiment, the specifying step comprises contacting cells with a specification media that comprises one or more factors that promote maturation, further lineage specification and/or expansion.

The term "specification media" as used herein refers to culture medium that is used to promote or facilitate specification of a cell or a cell population. One example of a hepatic specification media includes Iscove's Modified Dulbecco's Medium (IMDM) supplemented with 1% vol/vol B27 (Invitrogen: A11576SA), and ascorbic acid, MTG, a BMP4 agonist and at least one FGF agonist selected from FGF10, bFGF, FGF4 and FGF2. For some stages and in some embodiments, the same specification media can be used for example for specifying both hepatocyte and cholangiocyte lineages. In other stages and in other embodiments, the specification media comprises one or more factors that promote specification of hepatocyte and/or cholangiocyte development, for example a notch antagonist or a notch agonist. The term "specifying" as used herein means a process of committing a cell toward a specific cell fate, prior to which the cell type is not yet determined and any bias the cell has toward a certain fate can be reversed or transformed to another fate. Specification induces a state where the cell's fate cannot be changed under typical conditions.

Specification of the induced endoderm along a hepatic fate can for example be confirmed by measuring hepatic and/or cholangiocyte expressed genes, including for example Tbx3 ALB, AFP, CK19, Sox9, NHF6beta and Notch2 as demonstrated for example in Example 9. For example, it is demonstrated that Notch 2 expression is upregulated in HGF/DEX/OSM treated hepatoblasts. Detection of Notch2 protein and/or expression can be used to confirm that the cell population can be specified to cholangiocytes, for example Notch2 can be detected as described in Example 9.

In the context of a cell, the term "differentiated", or "differentiating" is a relative term and a "differentiated cell" is a cell that has progressed further down the developmental pathway than the cell it is being compared with. Thus, stem cells can differentiate to lineage-restricted precursor cells (such as an induced endodermal progenitor cell), which in turn can differentiate into other types of precursor cells further down the pathway and then mature to an end-stage functional cell, which plays a characteristic role in a certain tissue type, and may or may not retain the capacity to proliferate further. The term "differentiation" as used herein includes steps for producing an induced endodermal population and specified cell populations, for example a hepatocyte or cholangiocyte specified cell population.

In another embodiment, the aggregates are generated from a cell population comprising at least 70%, 80%, 85%, or at least 90% albumin positive cells In another embodiment, the aggregates are generated after 24, 25, 26, 27, or 28 days in culture (for example where the day PSCs are obtained is considered day 0).

Optionally, aggregates are generated by enzymatic treatment and/or manual dissociation. In some embodiments, aggregates are generated by dissociating cells with collagenase and/or TrypleLE. In some embodiments, the cells are subsequently cultured in ultra-low cluster dishes. In other embodiments, monolayer cultures can be broken apart mechanically by pipetting, or can be dissociated enzymatically and aggregated with an incubation in low attachment plates or by shaking the population of cells. Aggrewells can optionally be used.

Figure 9A:
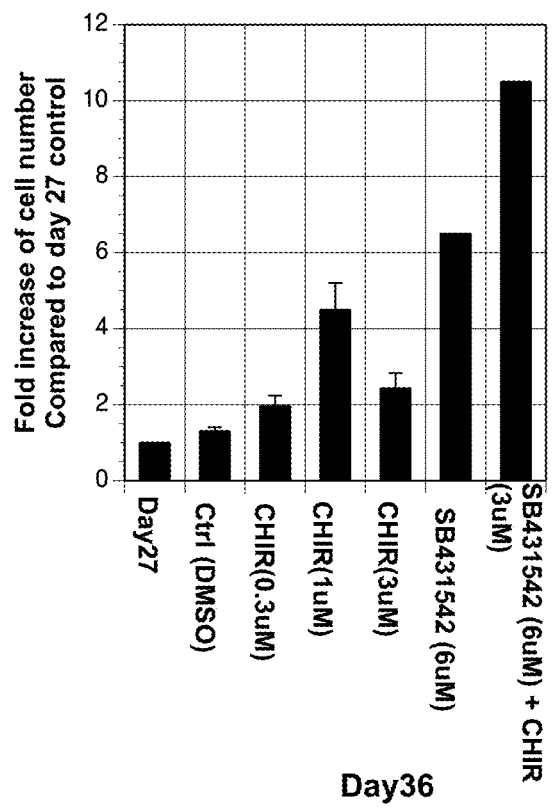
FIGS. 9A-9F depict factors that influence hepatic progenitor proliferation and maturation.
Figure 9B:
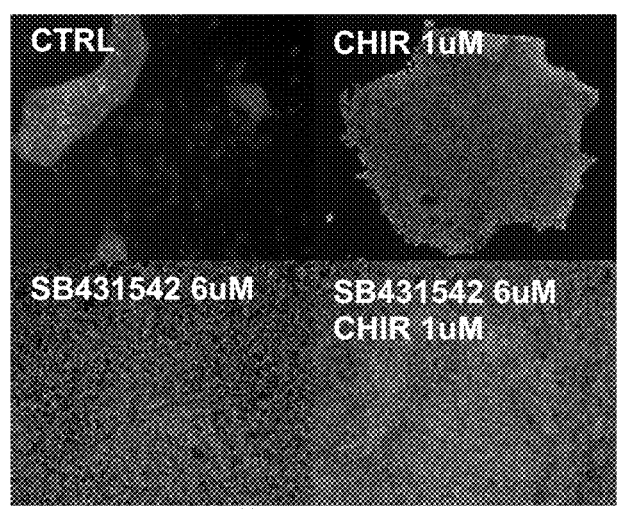
Figure 9C:
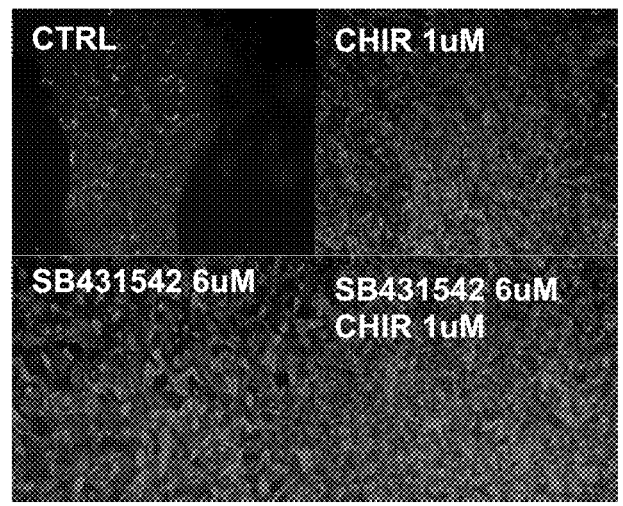

In an embodiment, the cells (e.g. monolayers and cells prior to aggregation) are gown on matrix coated plates, optionally on Matrigel coated plates. Other matrix coated plates that support the attachment of hepatoblasts, hepatocytes and/or cholangiocytes can also be used, for example laminin, fibronectin and collagen coated plates. FIG. 9F for example demonstrates ALB expression at day 26 of induction using several different matrix coating substrates.

Inducing maturation, further lineage specification and/or expansion can comprise one or more substeps.

In a further embodiment, the cell population comprising hepatocyte and/or cholangiocyte progenitors and/or the aggregates are cultured in the presence of hepatocyte growth factor (HGF), dexamethasone (DEX) and/or Oncostatin M (OSM) and/or active conjugates and/or fragments thereof. For example, the cell population comprising hepatocyte and/or cholangiocyte progenitors can be cultured in a maturation media comprising HGF, DEX and/or OSM for about 10, 11, 12, 13 or 14 days prior to aggregation and/or subsequent to aggregation the aggregates can be cultured in a maturation media comprising HGF, DEX and/or OSM for about 6, 7, 8, 9, or 10 days. For example, addition of about 10 ng/mL HGF promotes survival of aggregates.

In one embodiment, inducing maturation, and optionally inducing further lineage specification and/or expansion further comprises activating the cAMP pathway within the cells of the aggregates to induce the differentiation and/or maturation of the hepatocyte and cholangiocyte progenitors into hepatocytes and/or cholangiocytes.

The extended nodal agonist treatment and the aggregation of cells for example at day 25 for monolayer induced cells and day 26 for EB induced cells, produce a population which is for example capable of responding to cAMP signaling. As shown herein, activation of cAMP increases CYP expression and hepatocyte maturation.

In another embodiment, activating the cAMP pathway comprises contacting the aggregates with a cAMP agonist analog such as 8-bromoadensoine-3'5"-cyclic monophosphate (8-Br-cAMP), dibutyryl-cAMP, Adenosine-3', 5'-cyclic monophosphorothioate, Sp-isomer (Sp-cAMPS) and/or 8-Bromoadenosine-3', 5'-cyclic monophosphorothioate, Sp-isomer (Sp-8-Br-cAMPS) and/or any other cAMP agonist, such as cholera toxin, forskolin, caffeine, theophylline and pertussis toxin. Experiments have been conducted for example using Sp-8-Br-cAMP (Biolog: Cat. No.: B 002 CAS No.: [1 27634-20-2]), 8-Br-cAMP and forskolin (FSK) (Sigma: 66575-29-9). For example, the combination comprising Forskolin (FSK) (Sigma: 66575-29-9)+XAV939+ PD0325901 was effective to increases CYP expression and induce the maturation of the hepatocyte progenitors into hepatocytes. As used herein "cAMP agonists" include, cAMP, cAMP analogs that activate cAMP as well as molecules such as cholera toxin, forskolin, caffeine, theophylline and pertussis toxin which activate cAMP. IBMX which is a phosphodiesterase inhibitor, (phosphodiesterases are cAMP inhibitors) can also be used in some embodiments, for example in combination with forskolin.

It has been found also for example that the addition of 10 ng/ml HGF (reduced from 20 ng/ml) promotes survival of the aggregates whereas maintaining OSM has an inhibitory effect on the induction of expression of Phase 1 CYP enzymes, in particular CYP 3A4. Accordingly, in some embodiments, aggregates are cultured with cAMP analogs and/or agonists in the absence of OSM.

The term "maturation" as used herein means a process that is required for a cell (e.g. hepatoblast) to become more specialized and/or attain a fully functional state, for example its functional state in vivo. In one embodiment, the process by which immature hepatocytes or hepatic progenitors become mature, functional hepatocytes is referred to as maturation.

FIG. 1A refers to "hepatic maturation A" and FIG. 14A refers to hepatoblast differentiation. The cell population referred to in both cases is a hepatoblast cell population, that can produce hepatocytes if continued to be cultured for example in the presence of DEX optionally in combination with HGF and OSM and/or cAMP or produce cholangiocytes if cultured in combination with a Notch agonist (e.g. a notch signal donor), such as OP9, OP9 delta and/or OP9 Jagged1 cells in the presence of EGF, TGFβ1, HGF and EGF.

The term "maturation media" as used herein refers to culture medium that is used to promote or facilitate maturation of a cell or a cell population and which can comprise maturation factors, as well as cell expansion inducers and lineage inducers. One example of a maturation media for inducing hepatocyte maturation includes Iscove's Modified Dulbecco's Medium (IMDM) supplemented with 1% vol/vol B27 (Invitrogen: A11576SA) as well as ascorbic acid, Glutamine, MTG and optionally Hepatocyte growth factor (HGF), Dexamethasone (Dex) and/or Oncostatin M. Another example of a maturation media for inducing hepatocyte includes Hepatocyte culture medium (HCM) (Lonza: CC-41 82) without EGF. The maturation media optionally also comprises a cAMP analog and/or cAMP agonist which for example induces expansion of hepatocyte lineage cells and their maturation. Maturation media can comprise factors that promote hepatocyte and/or cholangiocyte development, further lineage specification and/or expansion and/or further lineage selection. For example, Wnt antagonist alone or in combination with TGFbeta antagonists and/or MEK/Erk antagonists promote hepatocyte maturation. Notch agonists for example, are demonstrated herein to induce cholangiocyte lineage development and are added when cholangiocytes are desired. Similarly Notch antagonists promote hepatocyte lineages and can be added when hepatocytes are desired, for example to inhibit cholangiocyte development.

Different maturation medias can be used sequentially (e.g. a monolayer maturation media (used for example pre-aggregation), an aggregates maturation media (used for example post aggregation); a hepatocyte maturation media that for example comprises factors that promote hepatocyte development and a cholangiocyte maturation media that for example promotes cholangiocyte development.

For example, in an embodiment, a maturation media comprising a cAMP analog and/or cAMP agonist and DEX and optionally HGF is added to the aggregates subsequent to culturing the pre-aggregate population in the maturation media comprising HGF, DEX and OSM, for example for about 10, 11, 12, 13 or 14 days.

The term "hepatocyte" as used herein refers to a parenchymal liver cell. Hepatocytes make up the majority of the liver's cytoplasmic mass and are involved in protein synthesis and storage, carbohydrate metabolism, cholesterol, bile salt and phospholipid synthesis and the detoxification, modification and excretion of exogenous and endogenous substances.

The term "primary hepatocyte" as used herein is a hepatocyte that has taken directly from living tissue (e.g. biopsy material) and established for growth in vitro.

The term "hepatoblast" as used herein refers to a progenitor cell which has the capacity to differentiate into cells of the hepatic and cholangiocyte lineages e.g. a hepatocyte or a cholangiocyte. Hepatoblasts are for example a subset of hepatocyte and cholangiocyte progenitors which can comprise immature hepatocytes and immature cholangiocytes (e.g. cells which have a specified cell fate and can mature to a hepatocyte only or a cholangiocyte only). In some embodiments, hepatoblast cells are defined by expression of markers such as Hex, HNF4, alpha-fetoprotein (AFP) and albumin (ALB). For example, hepatoblasts can give rise to cholangiocyte cells (e.g. CK19$^+$ cells) when notch signaling is activated in for example day 28 hepatoblast containing cultures. The term "hepatocyte progenitor" as used herein means cells that have the capacity to differentiate into functional hepatocytes which are for example, albumin positive and/or expresses CYP enzymes.

The term "cholangiocyte progenitor" as used herein means cells that have the capacity to differentiate into functional cholangiocytes which are for example CK19 positive and/or express CFTR.

The terms "immature hepatocyte" as used herein refers to a hepatocyte lineage cell that expresses albumin but that does not express appreciable levels of functional CYP3A4 and/or CYP1A2 enzyme. In some embodiments, immature hepatocytes must undergo maturation to acquire the functionality of mature hepatocytes. In some embodiments, immature hepatocyte cells are defined by expression of markers such as Hex, alpha-fetoprotein and albumin.

A "mature hepatocyte" as used herein means a hepatocyte lineage cell that express CYP enzymes for example CYP3A4 and CYP1A2 and albumin. Optionally, mature hepatocytes include functional, or measurable, levels of metabolic enzymes such as Phase I and Phase II drug-metabolizing enzymes for example comparable to adult cells. Examples of Phase I drug-metabolizing enzymes include but are not limited to cytochromes P450 CYP1A2, CYP3A4 and CYP2B6. Examples of Phase II drug-metabolizing enzymes include but are not limited to arylamine N-acetyltransferases NAT1 and NAT2 and UDP-glucuronosyltransferase UGT1A1. For example, the mature hepatocyte can be a metabolically active hepatocyte. Cellular uptake of Indocyanine green (ICG) is considered to be a characteristic of adult hepatocytes[29] and is used clinically as a test substrate to evaluate hepatic function[30]. A mature hepatocyte is for example an ICG positive staining hepatocyte. In a population of hepatocytes, the population of hepatocytes can be considered a mature 50%, 60%, 70%, 80%, 90% or more of the hepatocytes are ICG. A mature hepatocyte expresses increased albumin compared to an "immature hepatocyte" for example at least 5%, 10%, 25%, 50%, 75%, 100% or 200% more albumin, than an immature hepatocyte.

In an embodiment, the hepatocyte is a functional hepatocyte.

The term "functional hepatocyte" as used herein refers to a hepatocyte cell that displays one or more of characteristics of an adult hepatocyte (e.g. a mature hepatocyte) and/or an immature hepatocyte that is committed to a hepatic fate and is more differentiated than a starting cell (e.g. compared to an endodermal population cell, a hepatocyte precursor or an immature hepatocyte), which for example expresses albumin and/or increased albumin compared to a starting cell. Optionally, functional hepatocytes are mature hepatocytes and include functional, or measurable, levels of metabolic enzymes such as Phase I and Phase II drug-metabolizing enzymes for example comparable to adult cells. For example, the functional hepatocyte can be a metabolically active hepatocyte. Cellular uptake of Indocyanine green (ICG) is considered to be a characteristic of adult hepatocytes 29 and is used clinically as a test substrate to evaluate hepatic function[30]. A functional hepatocyte is for example an ICG positive staining hepatocyte. In a population of hepatocytes, the population of hepatocytes can be considered a functional population of hepatocytes for example at least 25%, 30%, 35%, 40%, 45% 50%, 60%, 70%, 80%, 90% or more of the hepatocytes are ICG positive. In another example, a functional hepatocyte is an albumin secreting hepatocyte and a population of hepatocytes can be considered a functional population of hepatocytes if for example at least 25%, 30%, 35%, 40%, 45% 50%, 60%, 70%, 80%, 90% or more of the hepatocytes are albumin secreting.

In embodiments, the hepatocytes, optionally functional hepatocytes comprise increased expression of at least 1, 2, 3, 4, 5, 6, 7, 8, 9, 10 or more genes or protein selected from the group consisting of ALB, CPS1, G6P, TDO, CYP2C9, CYP2D6, CYP7A1, CYP3A7, CYP1A2, CYP3A4, CYP2B6, NAT2 and UGT1A1 compared to a cell population comprising hepatocyte and/or cholangiocyte progenitors, and/or hepatocytes produced from a non-extended nodal agonist treated induced endodermal cell population, produced without aggregation and/or cAMP signaling induction. In other embodiments, at least 40, 50, 60, 70, 80 or 90% of the hepatocytes, optionally functional hepatocytes, are ASGPR-1$^+$ cells.

In some embodiments, functional hepatocytes display nucleic acid or protein levels of CYP1A2, CYP2B6, CYP3A4, CYP2C9 and/or CYP2D6 that are comparable or higher than those found in primary mature hepatocytes, optionally levels that are increased at least 1.1, 2, 3, 4, or 5 fold or any 0.1 increment between 1.1 fold and 5 fold, optionally increased at least 50% to 100%, 75% to 125%, 85% to 115%, 90% to 110% or 95% to 105%. For example, increased expression of 1.15 fold to 6.1 fold (e.g. CYP1A2 6.1 folds (610%), CYP3A4 13.2 folds (1320%), CYP 2B6 2 folds (200%), CYP2C9 1.52 folds 152%, UGT1A1 2 folds (200%), CYP2D6 1.15 folds (115%)) of those found in primary hepatocytes. In some embodiments, hepatocytes display nucleic acid or protein levels of ALB, HNF4, AFP, CPS1, G6P, TD01, NAT1, NAT2 and/or UGT1A1 that are comparable or higher to those found in primary hepatocytes of similar stage, optionally levels that are at least 50% to 100%, 75% to 125%, 85% to 115%, 90% to 110% or 95% to 105% of those found in primary hepatocytes.

In other embodiments, functional hepatocytes display nucleic acid or protein levels of CYP1A2, CYP2B6, CYP3A4, CYP2C9 and/or CYP2D6 that are higher than those in hepatoblasts and/or immature hepatocytes, optionally levels that are at least 110%, 125%, 150%, 175%, 200%, 300%, 400% or 500% of those found in primary hepatocytes. In some embodiments, functional hepatocytes display nucleic acid or protein levels of ALB, CPS1, G6P, TD01, NAT1, NAT2 and/or UGT1A1 that are higher than those in hepatoblasts and/or immature hepatocytes, optionally levels that are at least 110%, 125%, 150%, 175%, 200%, 300%, 400% or 500% of those found in primary hepatocytes.

In other embodiments, functional hepatocytes express the receptor asialo-glycoprotein receptor 1 (ASGPR1). In other embodiments, at least 40, 50, 60, 70, 80 or 90% of the hepatocytes, optionally functional hepatocytes, are ASGPR-$1^+$ cells.

In further embodiments, functional hepatocytes display CYP1A2 activity in vitro. Optionally, functional hepatocytes display CYP1A2 activity is comparable or higher than those found in primary hepatocytes, optionally levels that are at least 50% to 100%, 75% to 125%, 85% to 115%, 90% to 10% or 95% to 105% of those found in primary hepatocytes. In some embodiments, CYP1A2 activity is measured by incubating cells with phenacetin and monitoring the generation of O-deethylated metabolite accumulation in the cells.

In further embodiments, functional hepatocytes display CYP2B6 activity in vitro. Optionally, functional hepatocytes display CYP2B6 activity that is comparable or higher than those found in primary hepatocytes, optionally levels that are at least 50% to 100%, 75% to 125%, 85% to 115%, 90% to 110% or 95% to 105% of those found in primary hepatocytes. In some embodiments, CYP2B6 activity is measured by incubating cells with bupropin and monitoring the formation of the metabolite O-hydroxy-bupropion in the cells.

In further embodiments, hepatocytes display NAT1 and/or NAT2 activity in vitro. Optionally, hepatocytes display NAT1 and/or NAT2 activity that is comparable or higher than those found in primary hepatocytes, optionally levels that are at least 1.1 fold, 2 fold, 3 fold 4 fold, 5 fold, 6 fold or about 50% to 100%, 75% to 125%, 85% to 115%, 90% to 110% or 95% to 105% of those found in primary hepatocytes. In some embodiments, NAT1 and/or NAT2 activity is indicated by the metabolism of sulfamethazine (SMZ) to N-acetylated SMZ.

In further embodiments, hepatocytes display UGT activity in vitro. Optionally, hepatocytes display UGT activity that is comparable or higher than those found in primary hepatocytes, optionally levels that are at least 50% to 100%, 75% to 125%, 85% to 115%, 90% to 110% or 95% to 105% of those found in primary hepatocytes. In some embodiments, UGT activity is indicated by the generation of 4-MU glucuronide (4-MUG) from 4-methylumbelliferone (4-MU) in the cells.

In embodiments, the hepatocytes, optionally functional hepatocytes comprise increased expression of at least 1, 2, 3, 4, 5, 6, 7, 8, 9, 10 or more genes or protein selected from the group consisting of ALB, CPS1, G6P, TDO, CYP2C9, CYP2D6, CYP7A1, CYP3A7, CYP1 A2, CYP3A4, CYP2B6, NAT2 and UGT1A1 compared to a cell population comprising hepatocyte and/or cholangiocyte progenitors, and/or hepatocytes produced from a non-extended nodal agonist treated induced endodermal cell population, produced without aggregation and/or cAMP signaling induction. In other embodiments, at least 40, 50, 60, 70, 80 or 90% of the hepatocytes, optionally functional hepatocytes, are ASGPR-$1^+$ cells.

In yet another embodiment, functional hepatocytes display a global gene expression profile that is indicative of hepatocyte maturation. Optionally, functional hepatocytes display a global gene expression profile that is more similar to a primary hepatocyte than a global gene expression profile of a hepatoblast and/or a immature hepatocyte. Global gene expression profiles are obtained by any method known in the art, for example microarray analysis.

In an embodiment, cholangiocyte fate is specified by treating aggregates of the cell population with a notch agonist.

The term "cholangiocyte" as used herein refers to the cells that make bile ducts.

The term "cholangiocyte precursor" as used herein refers to cells which have the capacity to differentiate into a cholangiocyte cell (e.g. hepatoblasts), as well as immature cholangiocytes that can mature to functional cholangiocytes. In some embodiments, cells of the cholangiocyte lineages are defined by expression of markers such as CK19, secretin receptor (SR), cystic fibrosis transmembrane conductance regulator (CFTR), and chloride bicarbonate anion exchanger 2 (Cl(−)/HCO(3)(−) AEs).

The term "immature cholangiocyte" as used herein refers to a cholangiocyte lineage cell which must undergo maturation to acquire the functionality of mature cholangiocytes. In some embodiments, immature cholangiocyte cells express CK19 and/or Sox9, optionally including early Notch agonist treated cells, optionally treated for at least 1 day, at least 2 days, at least 3 days, or at least 4 days.

In an embodiment, the cholangiocyte is a functional cholangiocyte.

The terms "functional cholangiocyte" as used herein refers to cholangiocyte cells that display one or more of the characteristics of adult cholangiocytes (e.g. mature cholangiocyte) and/or are CK-19, MDR1 and/or CFTR expressing cholangiocyte lineage cells. For example, functional cholangiocytes express the MDR1 transporter and can when in cystic structures, transport a tracer dye such as rhodamine123, into the structure luminal space. As another example, CFTR functional activity can be assessed for example using a forskolin induced swelling assay on cystic structures, as shown for example in FIG. 18. In a population of cholangiocytes, the population can be considered a functional population if for example at least 25%, 30%, 35%, 40%, 45% 50%, 60%, 70%, 80%, 90% or more of the cells express secretin receptor (SR), cystic fibrosis transmembrane conductance regulator (CFTR), CK19 and/or chloride bicarbonate anion exchanger 2 (Cl(−)/HCO(3)(−) AEs).

The term "mature cholangiocytes" as used herein are cholangiocytes that express specified transporter or cell membrane receptor activity, such as secretin receptor (SR), cystic fibrosis transmembrane conductance regulator (CFTR), and optionally chloride bicarbonate anion exchanger 2 (Cl(−)/HCO(3)(−) AEs).

In an embodiment, the population of cholangiocytes produced is a population of functional cholangiocytes. The functional cholangiocyte comprises for example increased expression of at least 1, at least 2 or 3 genes or proteins selected from Sox9, CK19 and CFTR (Cystic fibrosis transmembrane conductance regulator) compared to the cells of the cell population comprising hepatocyte and cholangiocyte progenitors and/or compared to a population cells produced from aggregates not treated with a notch agonist. In other embodiments, at least 40, 50, 60, 70, 80 or 90% of the population of cholangiocytes are $CK19^+$ cholangiocytes. In other embodiments, at least 40, 50, 60, 70, 80 or 90% of the functional cholangiocytes are $CFTR^+$ cholangiocytes.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "cell culture medium" (also referred to herein as a "culture medium" or "medium") as referred to herein is a medium for culturing cells containing nutrients that maintain cell viability and support proliferation and optionally differentiation. The cell culture medium may contain any of the following in an appropriate combination: salt(s), buffer(s), amino acids, glucose or other sugar(s), antibiotics, serum or serum replacement, and other components such as peptide growth factors, vitamins etc. Cell culture media ordinarily used for particular cell types are known to those skilled in the art.

The suitable culture medium can include a suitable base culture medium including for example DMEM (Life Technologies), IMDM, RPMI, CMRL and/or any other or media that supports the growth of endodermal cells to provide for example a base culture medium composition to which components and optionally other agents can be added.

Various days of culture are referred to herein. A person skilled in the art would recognize that the culture periods can vary.

Figure 11A:
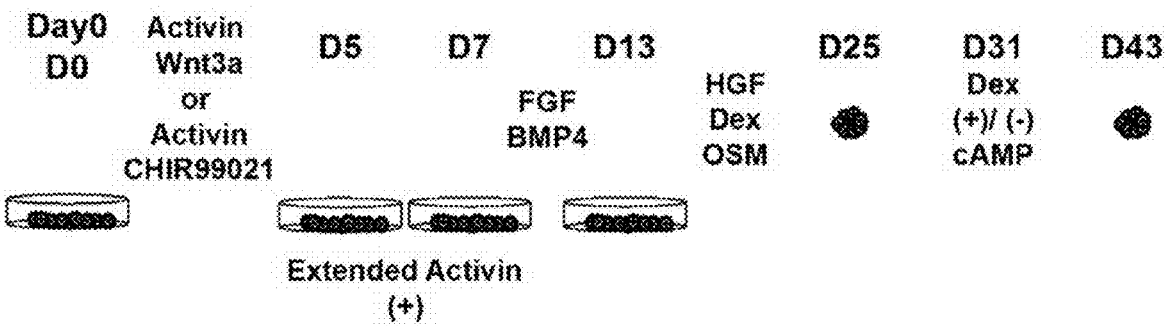
FIGS. 11A-11C are schematic representations of hepatocyte/cholangiocyte differentiation protocols.
Figure 11B:
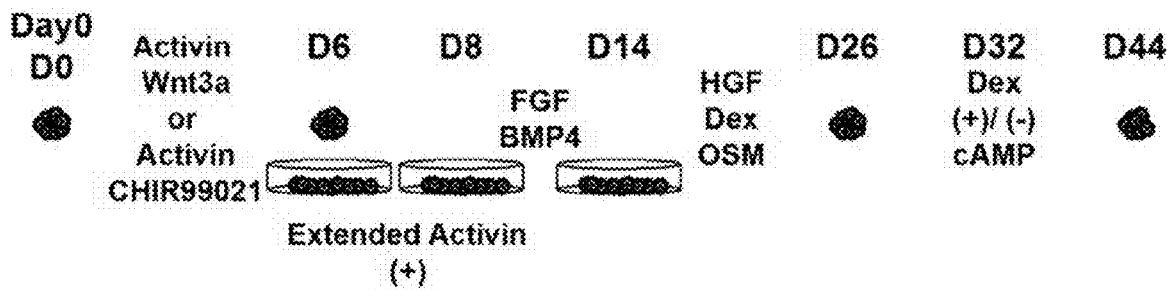
Figure 11C:
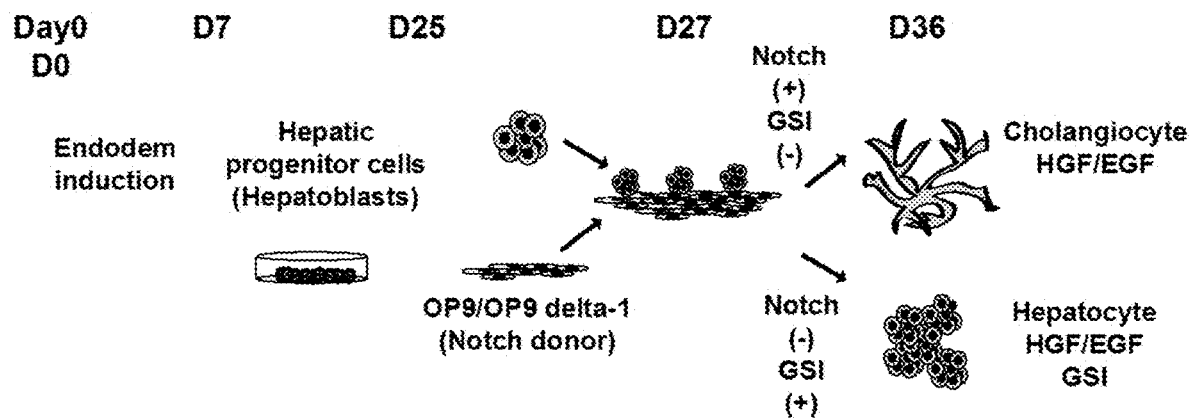

As used herein in some embodiments "day 5" refers generally to induced endoderm cell populations derived from for example PSC monolayers. Induced endoderm cell populations derived from EBs are cultured for about 6 days to arrive at a similar culture point as they require treatment for about 24 hours to induce EB formation. Hence, day 7 monolayer induction cultures are equivalent to day 8 embryoid body induction cultures etc. At this stage the induced endodermal population can comprise of cells that express for example Foxa2 and Sox17. Similarly, "day 7" generally refers to induced endodermal populations that have been extended nodal agonist treated for two days (e.g. which would be day 8 for EB methods). "Day 25" generally refers to the stage at which cells are aggregated (if derived from monolayers or Day 26 if derived from EBs). Where monolayer cells are used, equivalent methods can be used with EBs with the culture periods typically delayed 1 day. FIG. 11A provides an example of a schedule using monolayer cells (FIG. 11A) and an example using EBs (FIG. 1 B). An example schedule for the generation of cholangiocytes is provided in FIGS. 11C and 14A.

The term "FGF agonist" as used herein means a molecule such as a cytokine, including for example FGF, or a small molecule, that activates a FGF signaling pathway, e.g binds and activates a FGF receptor. For example, FGF receptor activation can be assessed by measuring MEK/ERK, AKT and/or PI3K activity by immunodetection.

The term "FGF" as used herein refers to any fibroblast growth factor, for example human FGF1 (Gene ID: 2246), FGF2 (also known as bFGF; Gene ID: 2247), FGF3 (Gene ID: 2248), FGF4 (Gene ID: 2249), FGF5 (Gene ID: 2250), FGF6 (Gene ID: 2251), FGF7 (Gene ID: 2252), FGF8 (Gene ID: 2253), FGF9 (Gene ID: 2254) and FGF10 (Gene ID: 2255) optionally including active conjugates and fragments thereof, including naturally occurring active conjugates and fragments. In certain embodiments, FGF is FGF10, FGF4 and/or FGF2.

As used herein, "active conjugates and fragments of FGF" include conjugates and fragments of a fibroblast growth factor that bind and activate a FGF receptor and optionally activate FGF signaling.

The concentration of FGF can for example range from about 1 ng to about 500 ng/ml for example from about 1 ng to about 250 ng/ml, from about 10 ng to about 250 ng/ml from about 10 ng to about 100 ng/ml. In another embodiment, the FGF concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

The concentration of FGF10 can for example range from about 1 ng to about 500 ng/ml for example from about 1 ng to about 250 ng/ml, from about 10 ng to about 250 ng/ml from about 10 ng to about 100 ng/ml. In another embodiment, the FGF10 concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

The concentration of bFGF can for example range from about 1 ng to about 500 ng/ml for example from about 1 ng to about 250 ng/ml, from about 10 ng to about 250 ng/ml from about 10 ng to about 100 ng/ml. In another embodiment, the bFGF concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

In an embodiment, the BMP4 agonist is selected from the group BMP4, BMP2, and BMP7, BMP4, BMP7 and BMP2 for example share the same receptors in embryo development.

The term "BMP4" (for example Gene ID: 652) as used herein refers to Bone Morphogenetic Protein 4, for example human BMP4, as well as active conjugates and fragments thereof, optionally including naturally occurring active conjugates and fragments, that can for example activate BMP4 receptor signaling. The concentration of BMP, for example, BMP4 can for example range from about 1 ng to about 500 ng/ml for example from about 1 ng to about 250 ng/ml, from about 10 ng to about 250 ng/ml from about 10 ng to about 100 ng/ml. In another embodiment, the BMP concentration, for example the BMP4 concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

As mentioned, the method can be applied to an endodermal cell population grown in a monolayer.

Accordingly, a further aspect includes a method of producing hepatocytes and/or cholangiocytes from a pluripotent stem cell population, the method comprising:
- a) contacting the pluripotent stem cells cultured as a monolayer, with an induction media comprising nodal agonist such as ActA and optionally a wnt/beta-catenin agonist such as i) Wnt3a and/or ii) a GSK-3 selective inhibitor such as CHIR-99021 to provide an induced endodermal cell population;
- b) contacting the induced endodermal cell population with a nodal agonist to provide an extended nodal agonist treated induced endodermal cell population; and
- c) specifying by contacting the extended nodal agonist treated induced endodermal cell population with a specification media comprising of an FGF agonist and a BMP4 agonist and/or active conjugates and/or fragments thereof to obtain a cell population comprising hepatocyte and/or cholangiocyte progenitors,
- d) optionally contacting the cell population comprising hepatocyte and/or cholangiocyte progenitors with a maturation media comprising HGF, dexamethasone and/or Oncostatin M and/or active conjugates and/or fragments thereof;
- e) inducing maturation, and optionally inducing further lineage specification and/or expansion of hepatocyte and cholangiocyte progenitors of the cell population into hepatocytes and/or cholangiocytes, the inducing maturation step comprising generating aggregates of the cell population.

Further, the endodermal population can also be comprised in embryoid bodies. Accordingly a further aspect comprises a method of producing hepatocytes and/or cholangiocytes from a pluripotent stem cell population, the method comprising:
- a) forming embryoid bodies (EBs) of the pluripotent stem cells, optionally by contacting the pluripotent stem cells with a BMP4 agonist;
- b) contacting the EBs with an induction media comprising a nodal agonist such as ActA and optionally a wnt/beta-catenin agonist such as i) Wnt3a and/or ii) a GSK-3 selective inhibitor such as CHIR-99021 to provide an induced endodermal cell population;
- c) dissociating the induced endodermal cell population to provide a dissociated induced endodermal cell population;
- d) contacting the dissociated induced endodermal cell population with a nodal agonist to provide an extended nodal agonist treated induced endodermal cell population;
- e) specifying by contacting the extended nodal agonist treated induced endodermal cell population with a specification media comprising of an FGF agonist and a BMP4 agonist and/or active conjugates and/or fragments thereof to obtain a cell population comprising hepatocyte and/or cholangiocyte progenitors,
- f) optionally contacting the cell population comprising hepatocyte and/or cholangiocyte progenitors with a maturation media comprising HGF, dexamethasone and/or Oncostatin M and/or active conjugates and/or fragments thereof; and
- g) inducing maturation, further lineage specification and/or expansion of hepatocyte and cholangiocyte progenitors of the cell population into hepatocytes and/or cholangiocytes, the inducing maturation, further lineage specification and/or expansion comprising generating aggregates of the cell population. In some embodiments, the inducing maturation, and optionally inducing further lineage specification and/or expansion step further comprises activating the cAMP pathway within the aggregates to induce the maturation of hepatocyte and/or cholangiocyte progenitors of the cell population into a population comprising hepatocytes and/or cholangiocytes. In an embodiment, the method comprises contacting the aggregates with a cAMP analog and/or cAMP agonist.

Another aspect includes a method of producing functional hepatocytes and/or cholangiocytes from pluripotent stem cells (PSCs) such as embryonic stem cells (ESCs) or induced pluripotent stem cells (iPSCs), the method comprising:
- a) contacting the pluripotent stem cells cultured as a monolayer for formed into embryoid bodies, with an induction media comprising nodal agonist such as ActA and optionally a wnt/beta-catenin agonist such as i) Wnt3a and/or ii) a GSK-3 selective inhibitor such as CHIR-99021 to provide an induced endodermal cell population;
- b) contacting the induced endodermal cell population with a nodal agonist to provide an extended nodal agonist treated induced endodermal cell population;
- c) specifying by contacting the extended nodal agonist treated induced endodermal cell population with a specification media comprising at least one FGF agonist and one BMP4 agonist and/or active conjugates and/or fragments thereof to obtain a cell population comprising hepatocyte and/or cholangiocyte progenitors, and
- d) inducing maturation, further lineage specification and/or expansion of hepatocyte and/or cholangiocyte progenitors into hepatocytes and/or cholangiocytes, the inducing maturation, further lineage specification and/or expansion comprising:
  - (i) culturing the cell population comprising hepatocyte and/or cholangiocyte progenitors with a maturation/specification media comprising HGF, OSM and DEX;
  - (ii) generating aggregates of the cell population, optionally when the cell population comprises at least 70%, 80%, 85%, or 90% albumin positive cells or after about 20 to about 40 days of culture for example after about 24 to about 28 days of culture;
  - (iii) culturing the aggregated cells in an aggregated cell maturation media: and
  - (iv) optionally activating the cAMP pathway in the aggregated cells, optionally within about 1 to about 10 days of aggregation, for example within 6 days of aggregation, optionally after about 27 to about 36 days of culture.

In one embodiment, embryoid bodies (EBs) of the pluripotent stem cells are formed by culturing the pluripotent stem cells in the presence of BMP4 (optionally 1-5 ng/ml BMP4 or about 5 ng/ml BMP4) for 12 to 36 hours, optionally about 24 hours.

After the EBs are formed, they may be recultured in induction medium supplemented with a nodal agonist for 3 to 10 days, optionally 4 to 8 days or about 5 or 6 days to induce an endodermal cell population. The nodal agonist is optionally Activin A. The EBs of are also optionally contacted with a wnt/beta-catenin agonist such as Wnt3a or a GSK-3 selective inhibitor such as CHIR-99021 to induce an endodermal cell population.

In some embodiments, the EBs are cultured in the presence of a nodal agonist such as Activin A for an additional 1 to 4 days (e.g. the extended nodal agonist treatment) (i.e., prior to contacting the endodermal cell population with a combination of at least one FGF agonist and one BMP4 agonist).

As mentioned cells are then treated to induce maturation, further lineage specification and/or expansion including for example aggregation and treatment with various maturation factors. These steps for example can generate a population of cells that is responsive to cAMP activation. Extended nodal agonist treatment and aggregation are steps that generate cells responsive to cAMP activation.

Cells responsive to cAMP activation are for example after 26 days of culture for monolayer based methods.

In an embodiment, the aggregated cell maturation/specification media can comprise factors which promote hepatocyte maturation or factors which promote cholangiocyte development or both and/or which increase expansion of a precursor population.

For example, the aggregates comprise hepatoblasts which as demonstrated can be specified to hepatocytes or cholangiocytes.

Optionally, inducing maturation, further lineage specification and/or expansion further comprises contacting the cell aggregates with i) a cAMP signaling activator (e.g. cAMP analog and/or agonist) and/or ii) an antagonist of Wnt/beta-catenin signaling (for example, Wnt inhibitor XAV 939) and/or an inhibitor of MEK Erk signaling (for example, MEK Erk inhibitor PD0325901). Addition of a Wnt antagonist and/or a MEK/Erk antagonist during activation of cAMP signaling enhances expression of CYP enzymes, for example up to levels or greater than levels seen in adult liver cells. For example, inhibition of MEK/Erk in the presence of cAMP, for example added to about day 28 to about day 32 cultures, results in hepatocytes with increased levels of CYP3A4. Addition of a MEK/Erk antagonist in combination with a Wnt antagonist is shown to also increase levels of CYP1A2. In an embodiment, wnt antagonists include for example XAV939, IWP2, DKK1, XXX (IWP2 (STEMGENT 04-0034), Dkk-1 (R&D, 5439-DK-01 0)), IWR-1 endo (Calbiochem 681 699-10). Known antagonists of Wnt signaling include Dickkopf (Dkk) proteins, Wnt Inhibitory Factor-1 (WIF-1), and secreted Frizzled-Related Proteins (sFRPs) and can be used in an embodiment. In another embodiment, the MEK/Erk antagonist is selected from PD0325901, U01 26 (Promega V 1121), PD 098059 (Sigma-Aldrich P215-1MG).

Optionally, the cell aggregates are contacted with 0.1 to 10 µM, optionally 0.5 to 2 µM or about 1 µM XAV 939 and/or PD0325901.

Concentrations of other inhibitors/activators are for example concentrations that give similar activation/inhibition to inhibitors activators described herein.

In another embodiment, inducing maturation, further lineage specification and/or expansion further comprises contacting the cell aggregates with both a cAMP analog and/or cAMP agonist and wnt agonist such as a GSK3 selective inhibitor (for example, CHIR99021) or a TGF-β antagonist (for example, inhibitor SB431542). Optionally, the cell aggregates are contacted with 0.1 to 10 µM, optionally 0.2 to 4 µM CHIR99021 and/or about 2 to 10 µM or about 6 µM SB431 542. TGF-β inhibitors include SB431 542 (Sigma-Aldrich S4317-5MG), SB 525334 (Sigma-Aldrich S8822-5MG), and A83-01 (Tocris, 2929).

As demonstrated herein, activation of the Wnt pathway and inhibition of TGF-p/SMAD pathway at for example day 27, promotes expansion of an albumin$^+$/HNF4$^+$ progenitor population. It is demonstrated for example that up to a 10 fold expansion of said population can be obtained when a wnt agonist is added.

In an embodiment, the aggregated cells are treated with a wnt agonist and optionally a TGF3 antagonist (such as SB431542) for about 6 to about 12 days, preferably about 8 to about 10 days, optionally 9 days. Such treatment, for example results in expansion of the hepatoblasts. In an embodiment the method comprises producing an expanded population of hepatoblasts. These cells can be used to produce more differentiated population of cells including mature hepatocytes and/or cholangiocytes.

In an embodiment, the TGF-β antagonist is selected from SB431542 (Sigma-Aldrich S4317-5MG), SB 525334 (Sigma-Aldrich S8822-5MG), A83-01 (Tocris, 2929).

In an embodiment, the aggregated cell maturation media comprises one or more factors which promote maturation, further lineage specification and/or expansion, optionally:

a wnt agonist such as CIHR 9902, optionally in combination with a TGFbeta antagonist such as SB431 542 which promotes expansion of an albumin$^+$/HNF4$^+$ progenitor population; or
  a Wnt antagonist such as XAV939 and/or a Mek/Erk antagonist, for example PD0325901 which is added during the cAMP activation step, which enhances expression of CYP enzymes and promotes maturation of hepatocyte precursors;

In another embodiment, the aggregated cell maturation media comprises one or more factors which promote maturation, further lineage specification and/or expansion, optionally:

a Notch agonist which promotes cholangiocyte lineage specification; a Notch antagonist such as gamma-secretase inhibitor (GSI) L695.458 which promotes hepatocyte lineage specification.

Figure 7A:
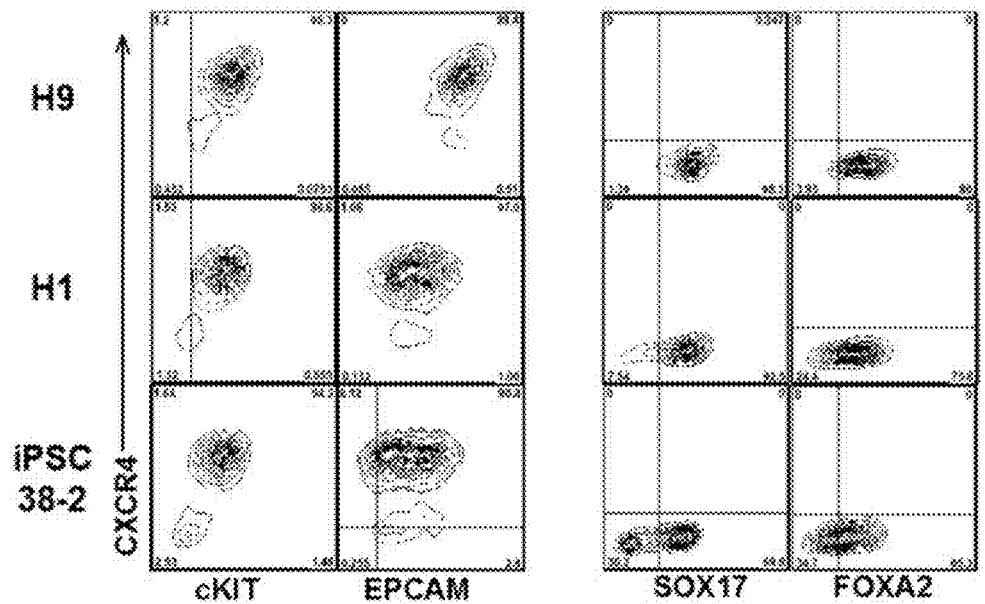
FIGS. 7A-7E show hepatic differentiation from different pluripotent stem cell lines.
Figure 7B:
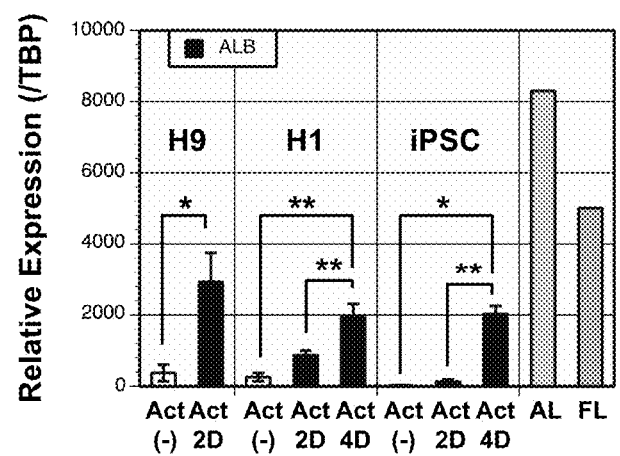
Figure 7C:
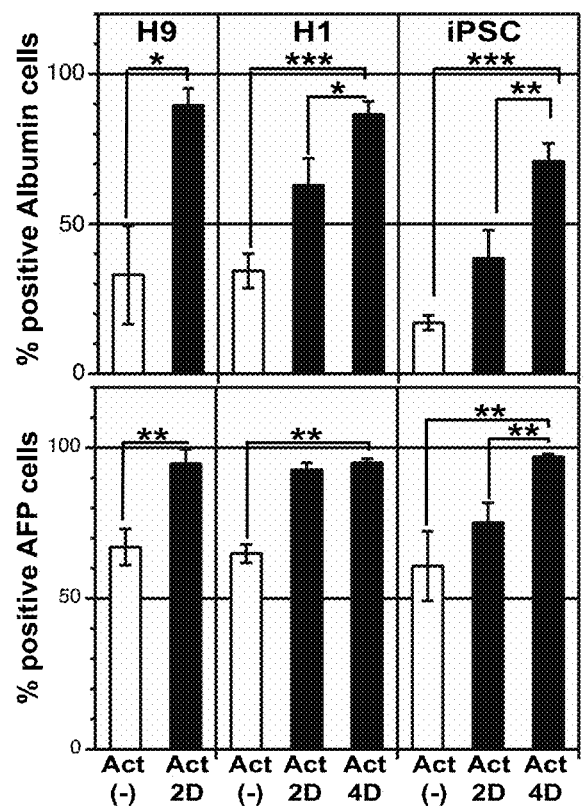
Figure 7D:
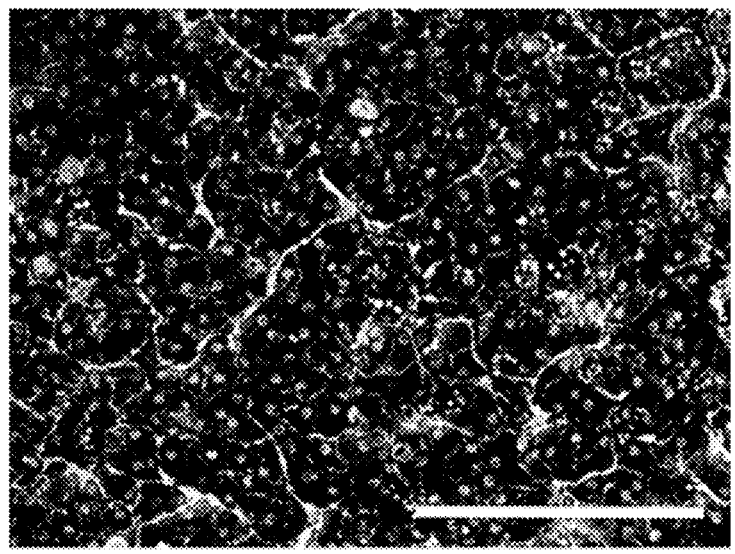
Figure 7E:
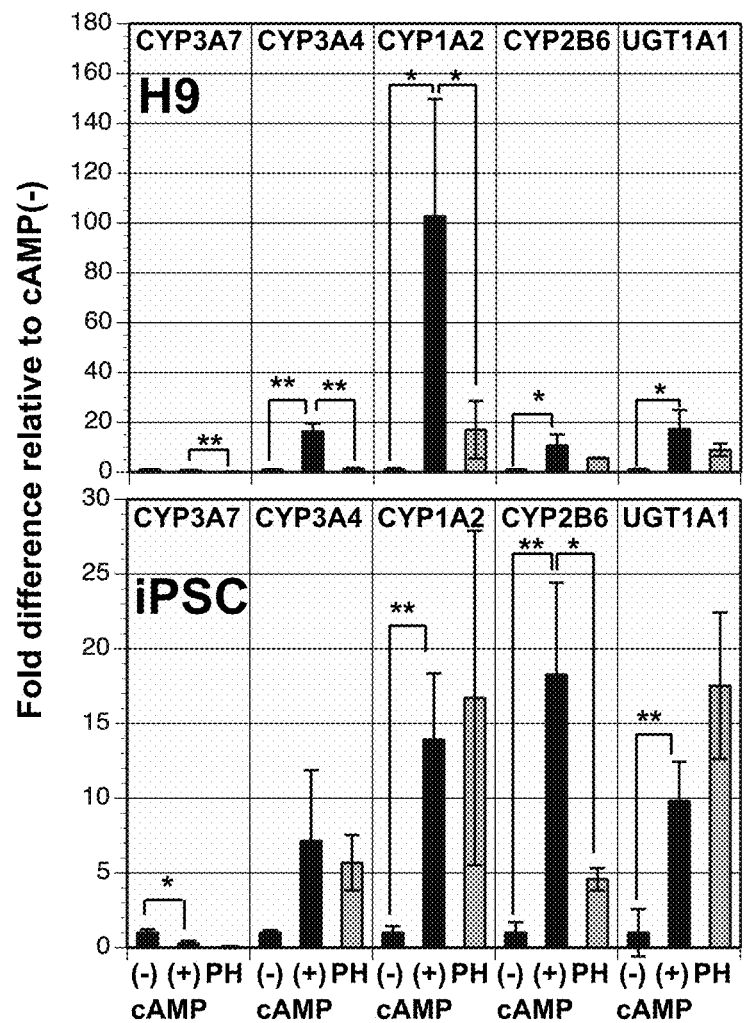

As described below, addition of cAMP analog 8-Br-cAMP, did induce significant levels of expression of CYP3A4 (16-fold), CYP1A2 (100-fold), and CYP2B6 (10-fold) and the Phase II enzyme UGT1A1 (16-fold) in the H9-derived aggregates (FIG. 7e).

In another embodiment, cell aggregates are generated from a monolayer of the cell population comprising hepatocyte and cholangiocyte progenitors by enzymatic treatment and/or manual dissociation.

In an embodiment, the cell population comprising hepatocyte and/or cholangiocyte progenitors which have been cultured in maturation/specification media comprising HGF, OSM and DEX, optionally prior to cell aggregation, are co-cultured with endothelial cells, optionally CD3$^4$ positive endothelial cells. In an embodiment, the endothelial cells are derived from embryonic ESC, preferably human. In an embodiment, the endothelial cells are mature endothelial cells optionally human, and/or derived from mature endothelial cells.

CD34$^+$ endothelial cells can for example be generated as described in Example 8 from hESCs. As described in Example 8, endothelial cells can be generated by induction with a combination of BMP4, bFGF and VEGF for about 6 days at which time the CD34$^+$ cells (also CD31 and KDR$^+$) can be isolated by FACS. The sorted CD34$^+$ cells can be further cultured for example for 6 days in endothelial cell growth media, optionally EMG2 media, and then used for the generation of chimeric aggregates.

Figure 12A:
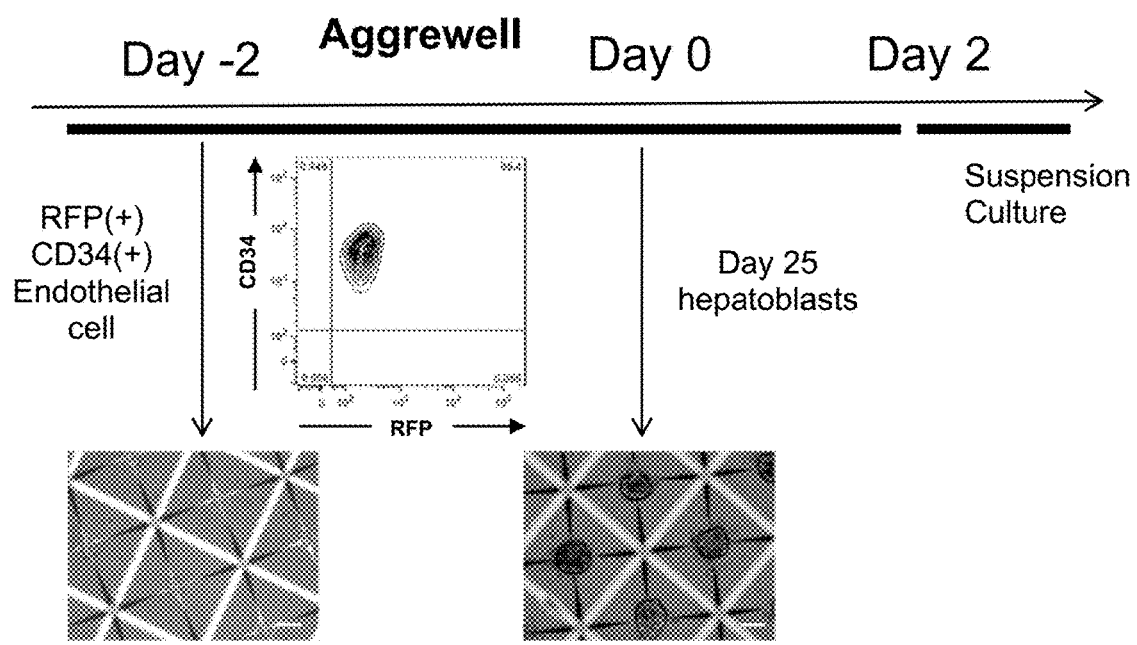
FIGS. 12A-12D demonstrate that hESCs-derived endothelial cells enhance hepatic maturation.
Figure 12B:
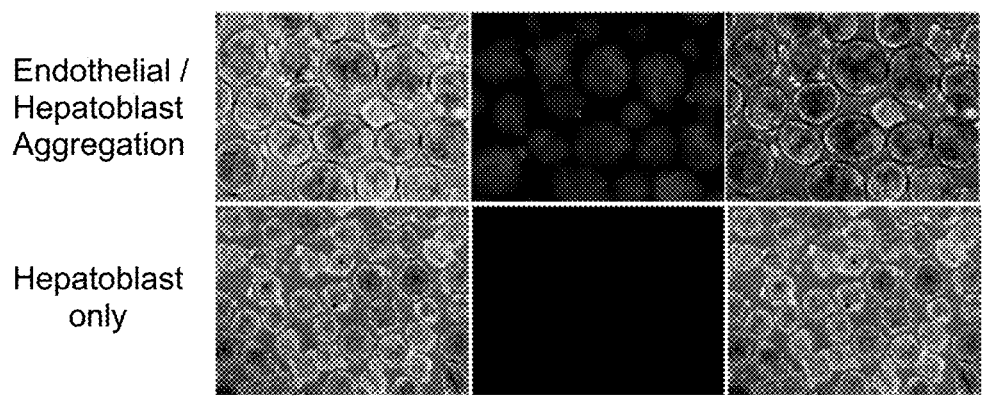
Figure 12C:
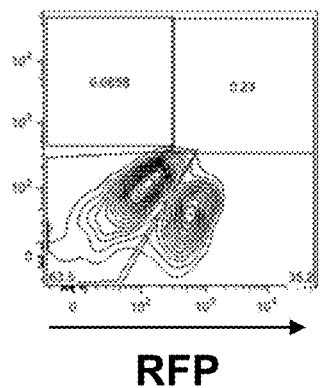
Figure 12D:
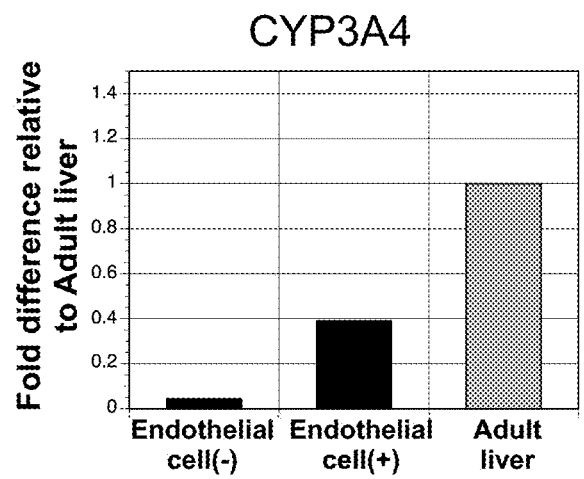

In an embodiment, the cell population comprising hepatocyte and/or cholangiocyte progenitors which have been cultured in maturation/specification media comprising HGF, OSM and DEX, are co-cultured with CD34$^+$ positive endothelial cells to form chimeric aggregates, optionally using an aggregation vessel (e.g. a vessel that promotes aggregation of a single cell type or mixed cell types) such as Aggrewells™ until chimeric aggregation is achieved, for example for about 1 day, about 2 days or about 3 days when using Aggrewells. Aggregation can also be performed using a method described herein or known in the art. As described in Example 8, the endothelial cells can be added to the vessels prior to the hepatic cell population to coat the bottom of the well. The hepatic cell population can be added as a single cell suspension, for example day 25/26 hepatoblasts can be added on top of the endothelial cells and the mixture cultured in the Aggrewells. Upon suitable aggregation, the chimeric hepatic/endothelial aggregates can be subsequently removed from the Aggrewells and cultured. As shown in FIG. 12B, the aggregates cultured together with the endothelial cells contained endothelial cells and were larger than those cultured alone. It is also demonstrated by qRT-PCR analyses that the chimeric hepatic/endothelial aggregates cultured for an additional 12 days expressed substantially higher levels of CYP3A4 message than the hepatic aggregates generated without the endothelial cells (FIG. 12d). As these levels were achieved without the addition of cAMP, endothelial cells may promote maturation of the hPSC-derived hepatic cells. In an embodiment, the hepatic/endothelial chimeric aggregates are cultured for at least or about 6 days, at least or about 8 days, at least or about 10 days, at least or about 12 days, or until a desired or preselected level of CYP3A4 message is attained.

In a further embodiment, the hepatic endothelial chimeric aggregates are cultured in a gelatinous matrix, optionally a collagen comprising matrix, optionally a gel. In an embodiment, the collagen is collagen I or IV. In an embodiment the gelatinous matrix comprises Matrigel, laminin, fibronectin, extracted ECM (e.g. extra cellular matrix from liver tissue) and/or combinations thereof.

In an embodiment, the aggregates cultured in a collagen comprising matrix are cultured in the presence of cAMP, PD0325901 and XAV939.

Figure 9D:
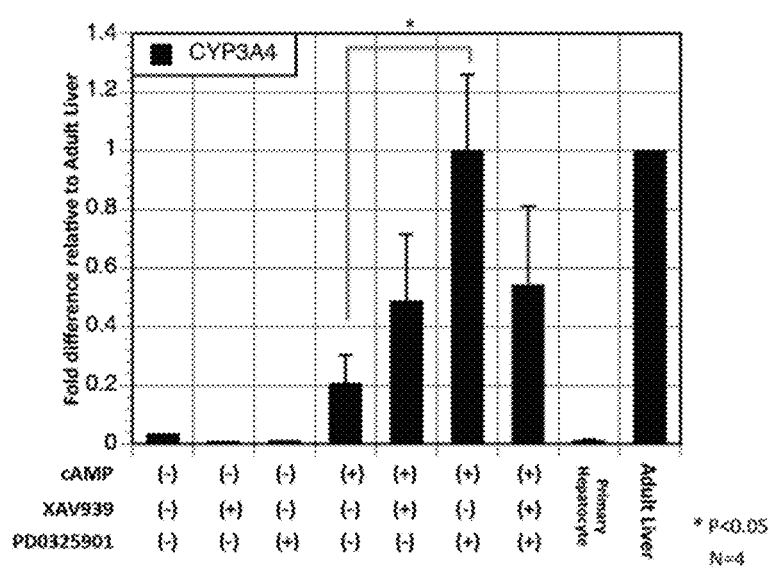
Figure 9E:
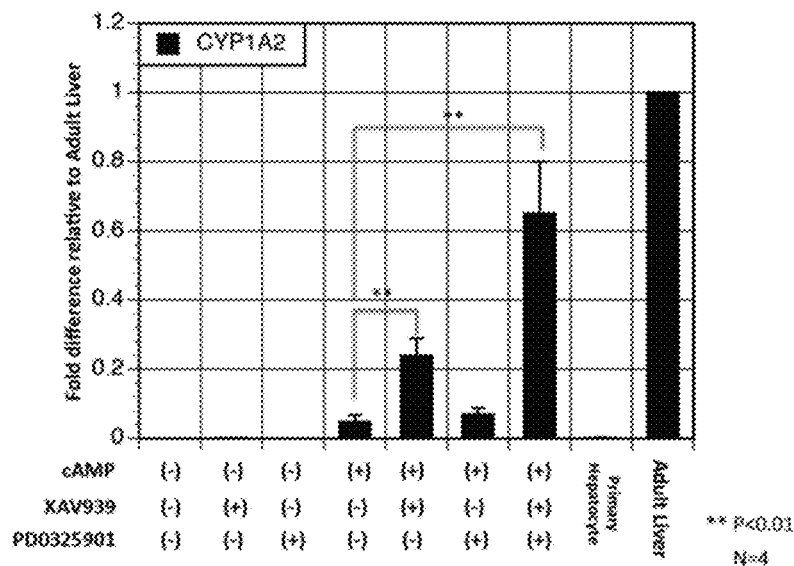
Figure 9F:
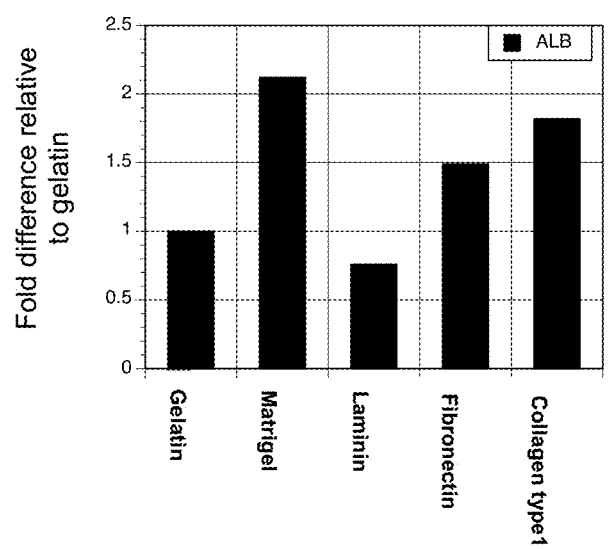
Figure 13:
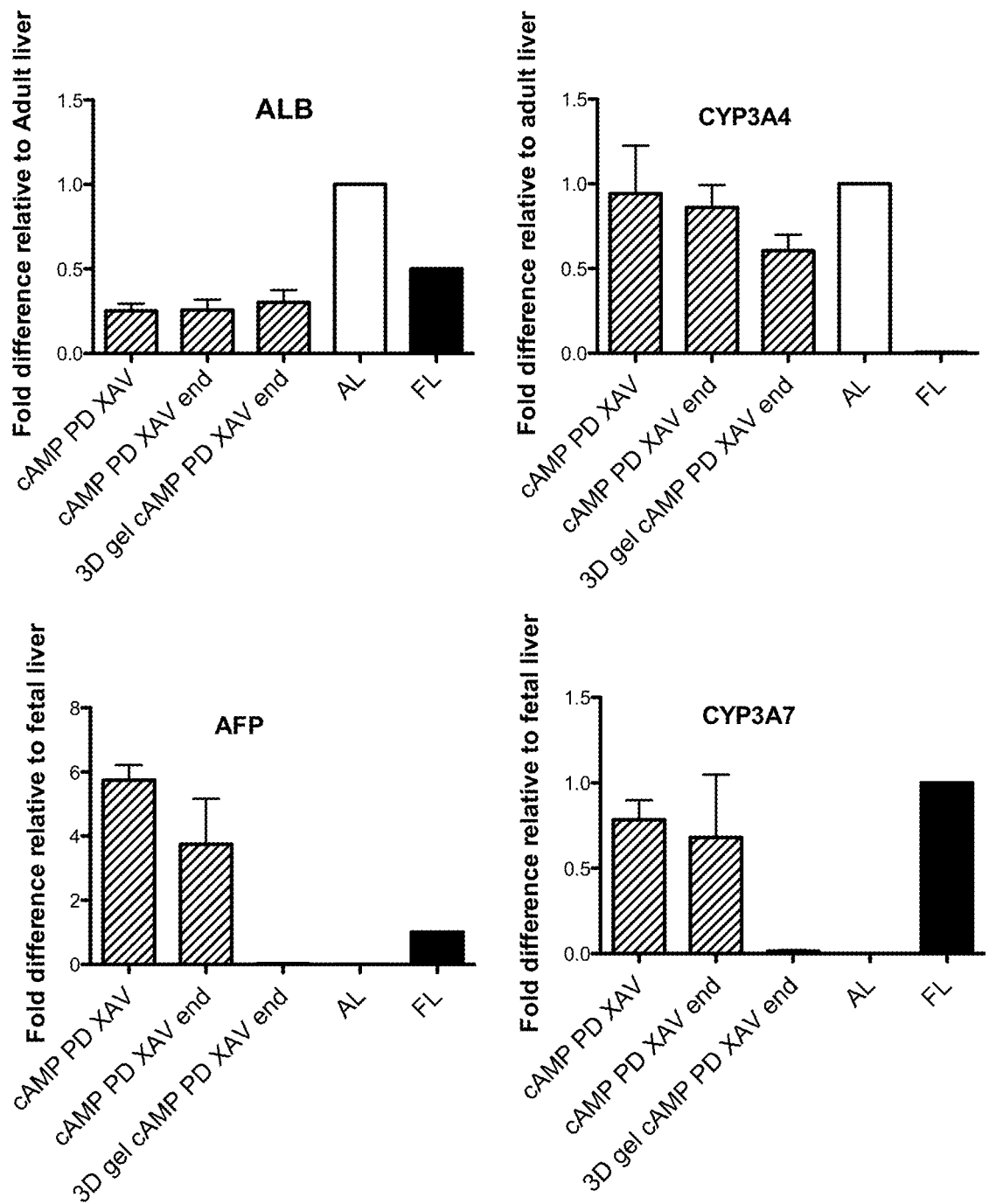
FIG. 13 demonstrates the effect of 3D gel culture on maturation of hPSC-derived hepatocytes. Aggregates consisting of hepatoblasts or hepatoblasts and endothelial cells (end) were generated at day 25 of culture and then cultured for an additional 7 days in liquid in hepatocyte culture medium supplemented VEGF and bFGF and followed by 12 days of culture in the same medium supplemented with cAMP, PD0325901 (PD) and XAV939. To test the effects of collagen on maturation, day 32 chimeric aggregates were embedded in a Collagen type 1 gel and cultured in the presence of cAMP, PD0325901 and XAV939 for 12 days. All cultures were harvested at day 44 and analyzed for expression of the indicated genes by qRT-PCR. Values are determined relative to TBP. The expression of ALB and CYP3A4 is presented as fold change relative to their levels in adult liver. The expression of AFP and CYP3A7 is presented as fold change relative to their levels in fetal liver. AL: Adult liver, FL: Fetal liver.

The combination of 3D aggregation, cAMP and PD/XAV was shown to promote significant differentiation of the human pluripotent stem cell-derived hepatocytes (FIG. 9), (FIGS. 9D and 9E). Some expression of AFP and fetal CYP3A7 was retained. It is demonstrated in Example 8, that treating the hepatic endothelial chimeric aggregates with a combination of cAMP, PD and XAV in collagen gels to provide a source of extracellular matrix proteins, promotes further maturation of the population. As shown in FIG. 13, the addition of endothelial cells to the aggregates (end) did not significantly impact the expression levels of ALB, CYP3A4, AFP or CYP3A7 when the aggregates were maintained in liquid culture. In contrast, culture of the aggregates in the collagen gel had a dramatic effect on AFP and CYP3A7 expression, as both were reduced to almost undetectable levels, similar to those found in the adult liver.

In an embodiment, for example within approximately 1 to about 4 days after aggregation the cells are treated with a notch agonist. Addition of a notch agonist at such stages promotes cholangiocyte maturation. In some embodiments, for example where cholangiocyte maturation is preferred, inducing cAMP signaling is omitted.

Accordingly, the disclosure also provides a method of inducing maturation of cholangiocyte progenitors into cholangiocytes, the inducing maturation, further lineage specification and/or expansion comprising:

(i) culturing a cell population comprising cholangiocyte progenitors with a Notch agonist to induce the maturation of cholangiocyte progenitors into cholangiocytes, optionally functional cholangiocytes.

In one embodiment, the method of producing functional cholangiocytes from pluripotent stem cells (PSCs) such as embryonic stem cells (ESCs) or induced pluripotent stem cells (iPSCs):

a) contacting the pluripotent stem cells cultured as a monolayer or formed into embryoid bodies, with an induction media comprising nodal agonist such as ActA and optionally a wnt/beta-catenin agonist such as i) Wnt3a and/or ii) a GSK-3 selective inhibitor such as CHIR-99021 to provide an induced endodermal cell population;

b) contacting the induced endodermal cell population with a nodal agonist to provide an extended nodal agonist treated induced endodermal cell population;

c) specifying by contacting the extended nodal agonist treated induced endodermal cell population with a specification media comprising at a FGF agonist and a BMP4 agonist and/or active conjugates and/or fragments thereof to obtain a cell population comprising hepatocyte and/or cholangiocyte progenitors; and d) inducing maturation and inducing further lineage specification and/or expansion of cholangiocyte progenitors into cholangiocyte, the inducing maturation, further lineage specification and/or expansion comprising:

(i) generating aggregates of the cell population, optionally when the cell population comprises at least 70%, 80%, 85%, 90% or 95% albumin positive cells or after about 20 to about 40 days of culture for example after about 24 to about 28 days of culture;

(ii) culturing the cell population comprising cholangiocyte progenitors with a maturation media comprising a Notch agonist, wherein when the Notch agonist is a Notch signaling donor cell, optionally OP-9, OP-Jagged1 and/or OP-9delta1 cells, the Notch signaling donor cell is co-aggregated with the cell population.

In a further embodiment, the aggregates are cultured (or co-cultured when comprising Notch signaling donor cells) in a gelatinous matrix, optionally a collagen comprising matrix, optionally a gel. In an embodiment, the collagen is collagen I or IV. In an embodiment the gelatinous matrix comprises Matrigel, laminin, fibronectin, extracted ECM (e.g. extra cellular matrix from liver tissue) and/or combinations thereof.

Further, inhibiting Notch signaling for example with a Notch antagonist such as gamma-secretase inhibitor (GSI) L695.458 (Tocris #2627) DAPT (Sigma Aldrich D5942) LY 411575 (Stemgent 04-0054) and L-685458) is demonstrated herein to inhibit cholangiocyte development and cells produced retain the characteristics of hepatocytes.

In another embodiment, the method of producing hepatocyte lineage cells such as hepatoblasts, hepatocytes and/or cholangiocytes from pluripotent stem cells (PSCs) such as embryonic stem cells (ESCs) or induced pluripotent stem cells (iPSCs), the method comprises:

a) contacting the pluripotent stem cells cultured as a monolayer for formed into embryoid bodies, with an induction media comprising a nodal agonist such as ActA and optionally a wnt/beta-catenin agonist such as i) Wnt3a and/or ii) a GSK-3 selective inhibitor such as CHIR-99021, optionally for about 4 to about 8 days, to provide an induced endodermal cell population;

b) contacting the induced endodermal cell population with a nodal agonist, optionally for about 2, 3, or about 4 days, to provide an extended nodal agonist treated induced endodermal cell population; and c) specifying by contacting the extended nodal agonist treated induced endodermal cell population with a specification media comprising at least one FGF agonist and one BMP4 agonist and/or active conjugates and/or fragments thereof, optionally for about 4 to about 10 days, to obtain a cell population comprising hepatocyte and/or cholangiocyte progenitors, and d) inducing maturation, further lineage specification and/or expansion of hepatocyte or cholangiocyte progenitors into optionally an expanded hepatoblast population and/or hepatocytes and/or cholangiocytes, the inducing maturation, and optionally further lineage specification and/or expansion comprising:
  (i) culturing the cell population comprising hepatocyte and/or cholangiocyte progenitors with a maturation media comprising HGF, Dex and OSM optionally for about 10 to 14 days;
  (ii) generating aggregates of the cell population, optionally when the cell population comprises at least 70%, 80%, 85%, or 90% albumin positive cells or after about 20 to about 40 days of culture for example after about 24 to about 28 days of culture;
  (iii) culturing the aggregates in maturation medium comprising optionally comprising Dex for 1 to 10 days;
  iv)
    a) culturing aggregates in a maturation medium (e.g. aggregation maturation medium) comprising Dex and optionally a cAMP analog and/or cAMP agonist for about 6 days to about 10 days, optionally within about 1 to about 10 days of generating the aggregates, for example within 6 days of aggregation, optionally after about 27 to about 36 days of culture; or
    b) culturing the aggregates in a maturation medium comprising a notch agonist and optionally a cAMP agonist, HGF, and/or EGF for about 6 days to about 20 days, optionally adding the notch agonist within about 1 to about 10 days of the generating aggregates step, for example within 6 days of the generating aggregates step, optionally after about 20 to 40 days of culture.

The Notch agonist can for example be any notch ligand bound to a surface such as a cell, plastic, ECM or bead. In one embodiment, the notch ligand is notch ligand delta Jagged-1 (EUROGENTEC 188-204), Jagged1 peptide (abeam, ab94375). Recombinant Human Pref-1/DLK-1/FA1 (R&D 144-PR). In one embodiment, inducing maturation, and further lineage specification and/or expansion comprises contacting a cell population comprising cholangiocyte progenitors with a notch signaling donor such as OP9, OP9delta, and/or OP9 Jagged-1 cells and optionally in the presence of EGF, TGFbeta-1, HGF and EGF, and/or HGF, TGFbeta-1 and EGF, for at least or about 5 to about 10, about 14 or more days, for example 90 days, optionally for at least or about 5 to at least or about 60 days, at least or about 30 days, at least or about 25 days, 2 at least or about 1 days and/or at least or about 14 days, to induce the maturation of cholangiocyte progenitors into functional cholangiocytes. It has been demonstrated that the structures produced can be maintained in culture for over 60 days. Accordingly in an embodiment, the cell population comprising cholangiocyte progenitors is contacted with a notch signaling donor (notch agonist) such as OP9, OP9delta, and/or OP9 Jagged-1 cells and optionally in the presence of EGF, TGFbeta-1, HGF and EGF, and/or HGF, TGFbeta-1 and EGF, for at least 5 days and optionally up to any day between 5 and 90, or 5 and 60 days.

Optionally, contacting a cell population comprising cholangiocyte progenitors with a notch signaling donor comprises co-culturing the cell population comprising cholangiocyte progenitors with a notch signaling donor such as OP9, OP9delta, and/or OP9 Jagged-1 cells and optionally in maturation media comprising EGF, TGFbeta-1, HGF and EGF, and/or HGF, TGFbeta-1 and EGF, for at least or about 5 to at least or about 90 days, optionally for at least or about 5 to at least or about 60 days, at least or about 30 days, at least or about 25 days, 2 at least or about 1 days and/or at least or about 14 days to induce the maturation of cholangiocyte progenitors into a cholangiocytes, optionally functional cholangiocytes.

In one embodiment, inducing maturation, and optionally further lineage specification and/or expansion comprises co-culturing the cell population comprising cholangiocyte progenitors with OP9, OP9delta, and/or OP9 Jagged-1 cells and optionally in the presence of EGF, TGFbeta-1 HGF and EGF, and/or HGF, TGFbeta-1 and EGF, for at least 5, 8, 9, 10, 11, 12, 13 or 14 days or more, 90 days, optionally for at least or about 5 to at least or about 60 days, at least or about 30 days, at least or about 25 days, 2 at least or about 1 days and/or at least or about 14 days.

As used herein, the term "activator of Notch signaling" or "notch agonist" refers to as used herein any molecule or cell that activates Notch signaling in a hepatocyte and/or cholangiocyte and includes, but is not limited to, notch signaling donors such as OP9 cells, a line of bone marrow-derived mouse stromal cells and notch ligands. OP-9 cells endogenously express and have been engineered to overexpress one or more notch ligands. OP-9-Jagged1 are engineered to overexpress recombinant/exogenous Jagged-1 notch ligand and OP9-delta1 are engineered to overexpress recombinant delta 1 notch ligand. In an embodiment, the OP9 notch signaling donor is selected from OP9, OP9-Jagged1 or OP-delta1 cells. OP9 cells express notch ligand delta. As they express notch ligands they thereby can act as activators of Notch signaling. Also included are molecules and/or cells expressing Jagged-1 (EUROGENTEC 188-204), Jagged-1 peptide (abeam, ab94375) as well as recombinant Human Pref-1/DLK-1/FA1 (R&D 144-PR). The "notch agonist" can for example be bound to a surface such as a cell, plastic, ECM or bead.

In one embodiment, the cell population comprising cholangiocyte progenitors is co-cultured with OP9, OP9delta and/or OP9Jagged1 cells in the presence of 10 to 20 ng/ml, optionally about 20 ng/ml HGF and/or 25 to 75 ng/ml, optionally about 50 ng/ml EGF induce the differentiation of at least one cholangiocyte progenitor into a functional cholangiocyte.

As mentioned, the hepatoblast cells (e.g. stage day 25 or 26 as shown in FIGS. 1a and 14a can be aggregated (also referred to as 3D aggregates) as described in step g), step g) comprising inducing maturation, further lineage specification and/or expansion of hepatocyte and cholangiocyte progenitors of the cell population into hepatocytes and/or cholangiocytes, the inducing maturation, further lineage specification and/or expansion comprising generating aggregates of the cell population. These 3D aggregates comprise hepatoblast cells that can be matured/differentiated to hepatocytes or further specified to cholangiocytes. In embodiments where cholangiocytes are desired, further lineage specification is obtained by co-culturing the aggregates with a Notch signaling donor such as OP9, OP9delta and/or OP9 Jagged-1 cells, optionally as chimeric aggregates comprising hepatoblast cells and Notch signaling donor cells.

In an embodiment, the hepatoblast cell population comprising cholangiocyte progenitors is co-cultured with OP9, OP9delta and/or OP9Jagged1 cells, optionally as chimeric aggregates, in a matrix/gel comprising Matrigel and/or collagen.

In an embodiment, the matrix/gel comprises at least 20%, at least 30%, at least or up to 40%, at least or up to 50%, at least or up to 60%, at least or up to 70%, at least or up to 80%, at least or up to 90%, and/or up to 100% Matrigel.

In an embodiment, the collagen comprises collagen I and/or collagen IV. In an embodiment, the matrix/gel comprises from about 0 to about 5 mg/mL collagen I, optionally about 1.0 mg/mL, about 2 mg/mL, about 3.0 mg/mL, or about 4.0 mg/mL collagen I. In an embodiment, the matrix/gel comprises from about 1.0 mg/mL, about 1.2 mg/mL about 1.4 mg/mL, about 1.6 mg/mL, about 1.8 mg/mL, about 2.0 mg/mL, about 2.25 mg/mL, about 2.5 mg/mL, about 2.75 mg/mL, or about 3.0 mg/mL collagen I As demonstrated in Example 9, cyst structures are obtainable wherein the co-culture comprises a Matrigel composition of at least 30% or more. If increased branched structures are desired, the Matrigel concentration can be decreased to for example about 20%.

As demonstrated in Example 9, CFTR expressing cholangiocyte branched and cyst structures can be produced using a method described herein. The CFTR is functional as shown using swelling assays. Accordingly, in an embodiment, the cholangiocytes produced and/or isolated are CFTR expressing cholangiocytes.

The term "nodal agonist" as used herein means any molecule that activates nodal signal transduction such as "nodal" (for example human nodal such as Gene ID: 4338) or "activin" in a hepatocyte lineage cell.

The term "activin" or "ActA" as used herein refers to "Activin A" (for example Gene ID: 3624), for example human activin, as well as active conjugates and fragments thereof, optionally including naturally occurring active conjugates and fragments, that can for example activate nodal signal transduction as well as active conjugates and fragments thereof, including naturally occurring active conjugates and fragments. The concentration of activin can for example range from about 1 ng to about 500 ng/ml for example from about 1 ng to about 250 ng/ml, from about 10 ng to about 250 ng/ml from about 10 ng to about 100 ng/ml. In another embodiment, the activin concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

The term "HGF" as used herein refers to hepatocyte growth factor (Gene ID: 3082), for example human HGF, as well as active conjugates and fragments thereof, including naturally occurring active conjugates and fragments. The concentration of HGF can for example range from about 1 ng to about 500 ng/ml for example from about 1 ng to about 250 ng/ml, from about 10 ng to about 250 ng/ml from about 10 ng to about 100 ng/ml. In another embodiment, the HGF concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

The term "TGFbeta" as used herein means any one of TGFβ1, TGFβ2 and TGFβ3, for example human TGFβ1, TGFb2 and TGFb3, as well as active conjugates and fragments thereof including naturally occurring active conjugates and fragments. As described below, TGFβ1, promotes cholangiocyte branching when hepatoblasts are co-cultured with OP9. TGFβ2 and TGFβ3 have also been tested and promote branching structures under similar conditions.

The term "TGFbeta-1" as used herein refers to transforming growth factor beta 1, for example human TGFbeta1 Gene ID 7040) as well as active conjugates and fragments thereof including naturally occurring active conjugates and fragments. The concentration of TGFbeta1 for cholangiocyte specification can for example range from about 5 ng/ml to about 10 ng/ml.

The term "a wnt/beta-catenin agonist" as used herein means any molecule that activates wnt/beta-catenin receptor signaling in a hepatocyte and includes for example Wnt3a and as well as GSK3 selective inhibitors such as CHIR99021 (Stemolecule™ CHIR99021 Stemgent), 6-bromo-Indirubin-3'-Oxime (BIO) (Cayman Chemical (cat: 13123)), or Stemolecule™ BIO from Stemgent (cat: 04003). CHIR99021 is a selective inhibitor of GSK3. The GSK3 selective inhibitors contemplated are for example selective inhibitors for GSK-3/3 in the Wnt signaling pathway. Wnt/beta receptor signaling in a hepatocyte can be determined by for example by measuring increases in Axin2 gene expression for example by qPCR and/or measuring beta catenin phosphorylation, for example using Cignal TCF/LEF reporter from Qiagen (Cignal TCF/LEF Reporter (luc) Kit: CCS-01 8L).

The term "Wnt3a" as used herein refers to wingless-type MMTV integration site family, member 3A factor (e.g. Gene ID: 89780), for example human Wnt3a, as well as active conjugates and fragments thereof, including naturally occurring active conjugates and fragments. The concentration of Wnt3a can for example range from about 1 ng to about 500 ng/ml for example from about 1 ng to about 250 ng/ml, from about 10 ng to about 250 ng/ml from about 10 ng to about 100 ng/ml. In another embodiment, the Wnt3a concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

The term "agonist" as used herein means an activator, for example, of a pathway or signaling molecule. For example, a nodal agonist means a molecule that selectively activates nodal signaling.

The term "antagonist" as used herein means a selective inhibitor, for example of a pathway or signaling molecule. For example, a TGF beta antagonist is a molecule that selectively inhibits TGFbeta signaling, for example by measuring phosphorylation of Smad. A83-01 is a more potent inhibitor of smad2 than SB431 542.

The term "selective inhibitor" as used herein means the inhibitor inhibits the selective entity or pathway at least 1.5×, 2×, 3×, 4× or 10× more efficiently than a related molecule. For example a GSK-3 selective inhibitor inhibits GSK-3 in the wnt pathway at least 1.5×, 2×, 3×, 4× or 10× more efficiently than it is inhibited by for example LiCl or at least 1.5×, 2×, 3×, 4× or 10× more efficiently than it inhibits other kinases, other GSKs and/or GSK3 in other pathways. For example, CHIR 99021 has been shown in in vitro kinase assays to specifically inhibit GSK3B with an IC50 of about 5 nM and GSK3a with an IC 50 of 10 nM with little effect on other kinases. Accordingly, a selective inhibitor can exhibit an IC50 that is at least 1.5×, 2×, 3×, 4× or 10× lower than other for example, 2 other, 3 other etc. unrelated kinases. Similarly the term "selective activator" means an activator that activates the selective entity or pathway at least 1.5×, 2×, 3×, 4× or 10× more efficiently than a related molecule. The term "active fragments" as used herein is a polypeptide having amino acid sequence which is smaller in size than, but substantially homologous to the polypeptide it is a fragment of, and where the active fragment has at least 50%, or at least 60% or at least 70% or at least 80% or at least 90% or at least 100% effective biological action as compared to the full length polypeptide of which it is a fragment of or optionally has greater than 100%, for example 1.5-fold, 2-fold, 3-fold, 4-fold or greater than 4-fold effective biological action as compared to the polypeptide from which it is a fragment of.

The term "active conjugates" as used herein means a polypeptide (or other molecule" that is conjugated to a tag such as a fluorescent tag or stabilizing entity for example for improving stability under extended storage, heat, enzymes, low pH, stirring etc. that does not at all or substantially interfere with the activity of the active portion of the molecule. For example, the conjugate can have about at least 50%, or 60% or 70% or at 80% or 90% or 100% or greater than 100%, for example 1.5-fold, 2-fold, 3-fold, 4-fold or greater than 4-fold effective biological action (e.g. receptor activating activity) as compared to the unconjugated polypeptide or other molecule.

In one embodiment, the term "active fragments and conjugates" refers to fragments and conjugates of a molecule that retain the ability to activate the cognate receptor of the molecule. Optionally, active fragments and conjugates are at least 60%, 70%, 80%, 90% or 95% as active as the full length and/or unconjugated molecule.

Variants such as conservative mutant variants and activating mutant variants for each of the polypeptides can also be used.

The term "Dex" as used herein refers to dexamethasone (Dex). The concentration of Dex can for example range from about 1 ng to about 500 ng/ml for example from about 1 ng to about 250 ng/ml, from about 10 ng to about 250 ng/ml from about 10 ng to about 100 ng/ml. In another embodiment, the Dex concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

The term "OSM" as used herein refers to Oncostatin M. The concentration of OSM can for example range from about 1 ng to about 500 ng/ml for example from about 1 ng to about 250 ng/ml, from about 10 ng to about 250 ng/ml from about 10 ng to about 100 ng/ml. In another embodiment, the OSM concentration is about 10 ng/ml, about 20 ng/ml, about 30 ng/ml, about 40 ng/ml, about 50 ng/ml, about 60 ng/ml, about 70 ng/ml, about 80 ng/ml, about 90 ng/ml, about 100 ng/ml, about 150 ng/ml, about 200 ng/ml, about 300 ng/ml, about 400 ng/ml, or about 500 ng/ml.

As mentioned, some embodiments of the present disclosure, comprise activating the cAMP pathway within the aggregates to induce hepatocyte and/or cholangiocyte maturation.

As used herein, the term "cAMP pathway" refers to the adenyl cyclase pathway, a G protein-coupled receptor-triggered signaling cascade used in cell communication. The cAMP pathway is optionally the human cAMP pathway.

As used herein, the term "activating the cAMP pathway" refers to inducing the pathway to convert ATP into cAMP e.g increase levels of cAMP. When the cAMP pathway is activated, activated GPCRs cause a conformational change in the attached G protein complex, which results in the G alpha subunit exchanging GDP for GTP and separation from the beta and gamma subunits. The G alpha subunits, in turn, activate adenylyl cyclase, which converts ATP into cAMP. The cAMP pathway can also be activated downstream by directly activating adenylyl cyclase or PKA. Molecules that activate the cAMP pathway include but are not limited to cAMP, cAMP analogs such as 8-bromoadenosine-3',5'-cyclic monophosphate (8-Br-cAMP), dibutyryl-cAMP, Adenosine-3',5'-cyclic monophosphorothioate, Sp-isomer (Sp-cAMPS) and/or 8-Bromoadenosine-3',5'-cyclic monophosphorothioate, Sp-isomer (Sp-8-Br-cAMPS)). 8-Br-cAMP, dibutyrl-cAMP and Sp-cAMPS are examples of cell permeable analogs of cAMP. A number of other cAMP analogs that activate cAMP signaling are also known in the art and can be used. Other compounds that activate the cAMP pathway (e.g. cAMP agonists) include, but are not limited to, cholera toxin, forskolin, caffeine, theophylline and pertussis toxin. Experiments have been conducted for example using Sp-8-Br-cAMP (Biolog: Cat. No.: B 002 CAS No.: [127634-20-2]), 8-Br-cAMP and forskolin (FSK) (Sigma: 66575-29-9) showing that these compounds can be interchanged.

In some embodiments of the present method, the cAMP pathway is optionally activated by contacting the hepatic aggregates with 0.5 to 50 mM of a cell permeable cAMP analog such as 8-Br-cAMP, optionally 1-40, 1-30, 1-20, 5-15, 8-12 or about 10 mM 8-Br-cAMP. The hepatic aggregates are optionally contacted with the cell permeable cAMP analog for example 8-Br-cAMP for 1, 2, 3, 4, 5, 6, 7, 8, 9, or 10 days.

Inducing maturation, further lineage specification and/or expansion can comprise a series of steps.

In some embodiments, the cell population, comprising hepatocyte and/or cholangiocyte progenitors and/or the aggregates, is cultured in cell culture medium comprising HGF, dexamethasone and Oncostatin M. In other embodiments, the aggregates are cultured in cell culture medium comprising Iscove's Modified Dulbecco's Medium (IMDM) supplemented with B27, ascorbic acid, glutamine, MTG, HGF, dexamethasone and Oncostatin M. In other embodiments, the cells are cultured in cell culture medium comprising HGF, dexamethasone and Oncostatin M, optionally Iscove's Modified Dulbecco's Medium (IMDM) supplemented with B27, ascorbic acid, glutamine, MTG, HGF, dexamethasone and Oncostatin M prior to aggregation and/or during aggregation. The cell culture medium is optionally also supplemented with Rho-kinase inhibitor and BSA. For example, the cell population comprising hepatocyte and/or cholangiocyte progenitors can be cultured in a maturation media comprising HGF, DEX and OSM for 10, 11, 12, 13 or 14 days and/or the aggregates can be cultured in a maturation media comprising HGF, DEX and OSM for 6, 7, 8, 9, 10 days.

In another embodiment, the inducing maturation, further lineage specification and/or expansion step further comprises activating the cAMP pathway within the aggregates to induce the maturation of at least one hepatocyte or cholangiocyte progenitor into a functional hepatocyte and/or cholangiocyte cell. In another embodiment, activating the cAMP pathway comprises contacting the aggregates with a cAMP analog and/or cAMP agonist for example with a cAMP analog or cAMP agonist described above.

For example, in an embodiment, a maturation media comprising a cAMP analog and/or cAMP agonist and DEX and optionally HGF is added to the aggregates subsequent to culturing in the maturation media comprising HGF, DEX and OSM, for example for about 10, 11, 12, 13 or 14 days.

In one embodiment, aggregates are cultured in cell culture medium comprising HGF, Dex and OSM until the cAMP pathway is activated. In one embodiment, the aggregates are cultured medium containing a cAMP analog and/or cAMP agonist and Dex. OSM is removed from the medium when a cAMP analog and/or cAMP agonist is added. In some embodiments, HGF is also removed from the medium when a cAMP analog and/or cAMP agonist is added. In another embodiment, the amount of HGF in the medium is reduced following the addition of a cAMP analog and/or cAMP agonist (for example 10 ng/ml HGF is reduced from 20 ng/ml HGF).

In another embodiment, aggregates are cultured in HGF, Dex and OSM for about 6, 7, 8, 9, 10, 11 or 12 days at which point the cAMP analog and/or cAMP agonist is added. In one embodiment, OSM and optionally HGF are removed when the cAMP analog and/or cAMP agonist is added. In other embodiments, when cAMP analog and/or cAMP agonist is added, the concentration of HGF in the media is reduced (for example from about 20 ng/ml to about 10 ng/ml).

In some embodiments, at least 10%, at least 15%, at least 20%, at least 25%, at least 30%, at least 35%, at least 40%, at least 45% or at least 50% or at least 60% or at least 70%, at least 80%, at least 90% or at least 95% of the induced endodermal cell population differentiates/matures into functional hepatocytes and/or cholangiocytes.

Accordingly in an embodiment, the methods induce the production of greater than about 10%, 20%, 25%, 30%, 35%, 40%, 45%, 50% 55%, 60%, 65%, 70%, 75%, 80%, 85%, 90%, or about 95% functional hepatocytes and/or cholangiocytes from a population of nodal agonist treated induced endodermal cells.

Maturation for example can be detected by determining the level of mature hepatocyte markers. For example, CYP1A2, CYP2B6, CYP2D6, CYP3A4, CYP7A 1, CYP2C9, ALB, CPS1, G6P, TAT, TD01, NAT2, UGT1A1 and/or ASGPR1 are mature hepatocyte or functional hepatocyte markers whose expression can be detected for example by RT-PCR. Differentiation can also be detected using antibodies that recognize mature hepatocyte cells, for example an antibody that detects ASGPR-1.

In an embodiment, the endodermal cell population is differentiated from pluripotent stem cells (PSCs) such as an embryonic stem cells (ESCs) or an induced pluripotent stem cells (iPSCs).

In an embodiment, the pluripotent stem cell is from a mammal, such as a human. In an embodiment, the pluripotent stem cell is a human ESC (hESC) or a human iPSC (hiPSC).

As used herein, the terms "iPSC" and "induced pluripotent stem cell" are used interchangeably and refers to a pluripotent stem cell artificially derived (e.g., induced or by complete reversal) from a non-pluripotent cell, typically an adult somatic cell, for example, by inducing expression of one or more genes (including POU4F1/OCT4 (Gene ID; 5460) in combination with, but not restricted to, SOX2 (Gene ID; 6657), KLF4 (Gene ID; 9314), cMYC (Gene ID; 4609), NANOG (Gene ID; 79923), LIN28/LIN28A (Gene ID; 79727)).

In an embodiment, the method comprises steps for obtaining the endodermal cell population. For example, methods are provided herein for inducing a definitive endoderm in a pluripotent stem cell such as an ESC or an iPSC.

In one embodiment, obtaining the endodermal cell population comprises forming embryoid bodies from the pluripotent stem cell culture. EBs are formed by any method known in the art, for example the method described in Nostro, M. C. et al.[18], wherein EBs are formed from small aggregates in culture for 24 hours in low levels of a BMP4 agonist.

In another embodiment, obtaining the endodermal cell population comprises obtaining and/or growing the pluripotent stem cell culture in a monolayer.

The EBs and/or monolayer cells are subsequently contacted with high concentrations of activin A to induce definitive endoderm. Optionally, the EBs and/or monolayer are exposed to 80 to 120 ng/ml or 90 to 110 ng/ml activin, optionally about 100 ng/ml activin A for about 1, 2, 3, 4, 5, 6, 7, 8, 9 or 14 days.

In another embodiment, the EBs and/or monolayer cells are contacted with a wnt/beta-catenin agonist such as Wnt3a or a GSK-3 selective inhibitor such as CHIR-99021, 6-bromo-Indirubin-3'-Oxime (BIO), or Stemolecule™ BIO in addition to activin A. For example, GSK-3 specific inhibitor BIO was demonstrated to maintain pluripotency in human and mouse ESC through activation of Wnt signaling.[53]

Optionally, the EBs and/or the monolayer cells are exposed to from 10 to 40 ng/ml Wnt3a, or 20 to 30 ng/ml Wnt3A, optionally about 25 ng/ml Wnt3a for about 1, 2, 3, 4, 5, 6, 7, 8, 9 or 10 days. In another embodiment, the EBs and/or the monolayer cells are exposed to from about 0.03 µM to about 30 µM CHIR-99021, or from about 0.1 µM to about 3 µM, optionally about 0.3 µM to about 1 µM CHIR-99021. In an embodiment, the EBs are exposed to from about 0.1 µM to about 2 µM. In another embodiment, the monolayer cells are exposed to from about 1 µM to about 30 µM, for example from about 1 µM to about 3 µM CHIR-99021. A person skilled in the art would be able to ascertain equivalently useful amounts of other GSK-3 inhibitors.

In some embodiments, the EBs and/or monolayer cells are first contacted with 80 to 120 ng/ml activin, or 90 to 110 ng/ml activin, optionally about 100 ng/ml activin A for about 1, 2, 3, 4, 5, 6, 7, 8, 9 or about 10 days prior to being contacted with 80 to 120 ng/ml activin, or 90 to 110 ng/ml activin, optionally about 100 ng/ml activin A and 10 to 40 ng/ml Wnt3a, or 20 to 30 ng/ml Wnt3A, optionally about 25 ng/ml Wnt3a for about 1, 2, 3, 4, 5, 6, 7, 8, 9 or about 10 days to produce an induced endodermal cell population.

In an embodiment and as described elsewhere, the induced endodermal cell population is cultured with a nodal agonist such as ActA for at least 36, 38, 42, 44, 46, 48, 50, 52, 56, 58 or 60 hours or for about 1 to about 4 days to produce the extended nodal agonist treated induced endodermal population.

Optionally, the base culture media for inducing definitive endoderm is any media known in the art for inducing definitive endoderm, optionally neural base media or StemPro34. In some embodiments, the cell culture medium is supplemented with activin A, glutamine, ascorbic acid, MTG, bFGF and BMP4. In other embodiments, the cell culture medium is further supplemented with a wnt/beta-catenin agonist such as Wnt3a or a GSK-3 selective inhibitor such as CHIR-99021.

Other methods of differentiating cells to obtain an induced endodermal cell population may also be used.

The definite endoderm or induced endodermal cell population is optionally defined by expression of the surface markers CXCR4, CKIT and EPCAM and the transcription factors SOX17 and FOXA2 or any combination thereof. In some embodiments, greater than 50%, 60%, 70%, 80%, 85%, 90% or 95% of the endodermal cell population expresses CXCR4, CKIT and EPCAM following activin induction. In another embodiment, greater than 50%, 60%, 70%, 80%, 85%, 90% or 95% of the endodermal cell population expresses SOX17 and/or FOXA2 following activin induction.

In certain embodiments, the method further comprises enriching and/or isolating functional hepatocytes and/or cholangiocytes to optionally generate an isolated population of functional hepatocytes and/or cholangiocytes.

In an embodiment, the isolating step comprises contacting the population of cells with a specific agent that binds functional hepatocytes and/or cholangiocytes.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from. The cells can for example be single cell suspensions, monolayers and/or aggregates. In some embodiments, for example comprising cholangiocytes, the isolated population can also comprise a notch ligand expressing cells such as OP9, OP9delta and/or OP9Jagged1 cells. In some embodiment, for example comprising hepatocytes, the isolated population can also comprise endothelial cells. The isolated population, optionally in dissociated cell suspension and/or aggregates can be used for example in screening applications, disease modeling applications and/or transplanting applications comprising for example scaffold etc.

The term "substantially pure", with respect to a particular cell population, refers to a population of cells that is at least about 65%, preferably at least about 75%, at least about 85%, more preferably at least about 90%, and most preferably at least about 95% pure, with respect to the cells making up a total cell population. Similarly, with regard to a "substantially pure" population of functional hepatocytes and/or cholangiocytes, refers to a population of cells that contain fewer than about 30%, fewer than about 20%, more preferably fewer than about 15%, 10%, 8%, 7%, most preferably fewer than about 5%, 4%, 3%, 2%, 1%, or less than 1%, of cells that are not functional hepatocytes and/or cholangiocytes or their progeny as defined by the terms herein. In some embodiments, the present invention encompasses methods to expand a population of functional hepatocytes and/or cholangiocytes, wherein the expanded population of functional hepatocytes and/or cholangiocytes is a substantially pure population of functional hepatocytes and/or cholangiocytes.

The terms "enriching" or "enriched" are used interchangeably herein and mean that the yield (fraction) of cells of one type is increased by at least about 10%, at least about 20%, at least about 30%, at least about 40%, at least about 50% or at least about 60% over the fraction of cells of that type in the starting culture or preparation. Enriching and partially purifying can be used interchangeably.

The population of cells can be enriched using different methods such as methods based on markers such as cell surface markers (e.g. FACS sorting etc.).

Cells and Compositions

As discussed above, functional hepatocytes and/or cholangiocytes can be isolated using the methods described herein. Accordingly, a further aspect of the application includes a population of cells produced according to a method described herein. In an embodiment, the population of cells is an enriched, purified or isolated cell population of hepatoblasts, hepatocytes and/or cholangiocytes, optionally mature and/or functional hepatocytes and/or cholangiocytes, for example produced according to a method described herein, and expressing for example markers of mature and/or functional cells. The enriched, purified or isolated are optionally single cell suspensions, aggregates, chimeric aggregates, and/or structures, including branched structures and/or cysts.

In an embodiment, the mature and/or functional hepatocytes lack expression of AFP and/or fetal CYP3A7.

In an embodiment, the mature and/or functional cholangioctye cells express MDR transporter gene, aquaporin, CFTR and/or a mutant thereof.

In an embodiment, the cell population is a hepatoblast cell population, optionally expressing Notch2.

In an embodiment, the isolated, purified and/or enriched population is in vitro produced.

In an embodiment, the population of cells are comprised in a composition with a suitable diluent.

A suitable diluent includes for example a suitable culture medium, or freezing medium containing for example serum, a serum substitute or serum supplement and/or a suitable cryoprotectant such as dimethyl sulphoxide (DMSO), glycerol methylcellulose or polyvinyl pyrrolidone. A further aspect comprises a culture medium supplement composition comprising optionally a FGF and/or a BMP4 agonist which can be used as a supplement for a cell culture base medium. The supplement can also include other components discussed herein such as activin A, Wnt3A, a GSK-3 selective inhibitor such as CHIR-99021, HGF, dexamethasone, Oncostatin M, ascorbic acid, glutamine and B27 supplement.

In an embodiment, the functional hepatocyte and/or cholangiocyte is derived from an iPS of a subject affected with a liver and/or biliary disease. In an embodiment, the disease is a monogenic disease e.g. cystic fibrosis, Alagille syndrome, progressive familial intrahepatic cholestasis (PFIC types 1, 2 and 3).

In an embodiment, the disease is cystic fibrosis. In an embodiment, the subject carries a mutation, for example in the cystic fibrosis gene, for example deltaF508, 997 CFTR del and/C1 CFTR mutation. As shown in FIG. 9, the methods described can generate hepatoblast populations from iPSCs generated/derived from a cystic fibrosis patient.

In an embodiment, the disease is a complex biliary disease, optionally primary sclerosing cholangitis or biliary atresia.

Another aspect includes an implantable construct or extracorporeal bioartificial liver device (BAL) comprising a population of cells described herein, prepared according to a method described herein.

Uses

The functional hepatocytes and/or cholangiocytes described herein and their derivatives are can be used in one or more applications. For example the methods can used to produce a population of hepatic lineage cells from iPSCs derived from or obtained from a subject affected by a liver and/or biliary disease.

Accordingly another aspect is a method for generating a liver and/or biliary disease cell model comprising:
  i) generating iPSCs from a cell derived or obtained from a subject affected the liver and/or biliary disease; and
  ii) generating hepatic lineage cells and/or hepatic lineage cell comprising aggregates and/or structures optionally branched structures and/or cysts according to a method described herein.

The disease is in an embodiment the disease is a monogenic disease e.g. cystic fibrosis, Alagille syndrome, progressive familial intrahepatic cholestasis (PFIC types 1, 2 and 3). In an embodiment, the disease is complex biliary disease, optionally primary sclerosing cholangitis or biliary atresia.

Another aspect is a method for generating a cystic fibrosis cell model comprising:
  i) generating iPSCs from a cell derived or obtained from a subject affected by cystic fibrosis; and
  ii) generating cholangiocyte lineage cells and/or cholangiocyte lineage cell comprising structures optionally branched structures and/or cysts according to a method described herein.

For example, the functional hepatocyte and/or cholangiocyte cells can be used for predictive drug toxicology, drug screening and drug discovery.

Accordingly, in an embodiment is provided is an assay comprising: contacting a functional hepatocyte and/or cholangiocyte population generated using a method described herein with a test compound, and measuring: 1) cell expansion, 2) maturation of hepatocyte cells and/or cholangiocyte specification, 3) one or more hepatoblast, hepatocyte and/or cholangiocyte properties; and/or 4) restoration and/or amelioration of one or more liver and/or biliary disease cell model deficiencies and compared to a wildtype cell population and/or other control tested in the absence of the test compound.

In an embodiment, the method further comprises measuring one or more hepatoblast, hepatocyte and/or cholangiocyte properties, including for example as measured in Example 9.

In an embodiment, the one or more cholangiocyte properties comprises:
  a) hepatoblast/cholangiocyte lineage differentiation capacity compared to wildtype iPSCs, optionally assessing I) presence and/or number of branched structures and/or cysts; II) cholangiocyte marker expression level, form (mature and/or immature form) and/or expression pattern;
  b) kinetics of cholangiocyte lineage formation compared to wildtype iPSCs; and/or
  c) transporter activity, optionally CFTR activity.

CFTR activity can for example be assessed by measuring cyst swelling, for example using a cAMP agonist such as forskolin. Example 9 provides an example of a method that can be employed to measure CFTR activity. For example, it was shown that chemical correctors VX809 and Corr-4a could restore/enhance mutant CFTR activity in cholangiocyte cysts, as measured by cyst swelling in the forskolin stimulation assay (Example 9). Restoration and/or amelioration of this or another property could be assessed when testing with putative or known CFTR treatments, for example providing for assessment of new drugs/biologies and/or for assessing patient specific response.

Another aspect includes a functional CFTR assay comprising:
  i) contacting cholangiocyte lineage cells, optionally in cysts, differentiated from iPSCs derived from a patient with CF and/or a CF related disease with a cAMP activator, optionally forskolin and IBMX (3-isobutyl-1-methylxanthine)
  ii) measuring swelling, optionally in the presence of a test agent, and
  iii) comparing to a wildtype cell or other control, optionally in the presence or absence of the test agent.

For example, the test agent can be compared to and/or tested in the presence of CFTR channel potentiator such as VX-770. VX-770 is an FDA approved drug (also known as Kalydeco) which is used for a patients carrying a particular CF mutation, G551 D.

The cells described can also be used for cell transplantation. For example, mixed population of cells, enriched and/or isolated functional hepatocytes and/or cholangiocytes can be introduced into a subject in need thereof, for example for treating liver disease.

Accordingly, an aspect includes obtaining cells and/or preparing isolated hepatocytes and/or cholangiocytes optionally functional hepatocytes and/or cholangiocytes according to a method described herein, and administering said cells to a subject in need thereof, for example a subject with liver and/or biliary disease.

For example, Yusa et al (55) described correcting a known gene defect in iPSC-derived hepatocytes and re-transplanting them. The corrected cells were re-transplanted back into mice and showed functionality that was previously absent in the diseased state. Yusa et al found the most suitable transposon for their purposes to be piggyBac, a moth-derived DNA transposon, which can transpose efficiently in mammalian cells including human embryonic stem (ES) cells. The mobile element enables the removal of transgenes flanked by piggyBac inverted repeats without leaving any residual sequences. The iPSC-3-G5-A7 generated, had the corrected A1AT, an intact genome compared to the parental fibroblast and expressed normal A1AT protein when differentiated to hepatocyte-like cells.

A transposon is optionally used. Other method of introducing an expression construct include lentiviral, adenoviral based methods. Efficient systems for the transfer of genes into cells both in vitro and in vivo are vectors based on viruses, including Herpes Simplex Virus, Adenovirus, Adeno-associated virus (AAV) and Lentiviruses. Alternative approaches for gene delivery in humans include the use of naked, plasmid DNA as well as liposome-DNA complexes (Ulrich et al., 1996; Gao and Huang, 1995). It should be understood that more than one transgene could be expressed by the delivered vector construct. Alternatively, separate vectors, each expressing one or more different transgenes, can also be delivered to the cell.

Cotransfection (DNA and marker on separate molecules) are optionally employed (see, e.g. U.S. Pat. Nos. 5,928,914 and 5,817,492). As well, a marker (such as Green Fluorescent Protein marker or a derivative) is useful within the vector itself (preferably a viral vector).

Commonly used systems for genome editing in human pluripotent stem cells are the transcription activator-like effector nucleases (TALENs) and the CRISPR-Cas9 system for example as described in Joung and Sander 2013 (56) and Ran et al 2013 (57) respectively.

A further method includes ZFN (Zinc finger nuclease), optionally combined with TALENs (transcription activator like effector nuclease for gene editing and correction of a mutated gene. See for example Gaj et al (58).

Accordingly, in an embodiment, the method comprises obtaining cells, optionally blood cells, from a patient affected by a liver and/or biliary disease, genome editing and/or inserting a construct encoding a functional and/or therapeutic protein; and either before or after inserting the construct, inducing hepatoblasts, hepatocytes and/or cholangiocytes according to a method described herein.

In an embodiment, the population of cells administered is an about day 25/26 population of cells. In an embodiment, the cells are specified to a hepatocyte or cholangiocyte fate.

Also included are uses of said cells and compositions comprising said cells for transplanting and/or treating a subject in need thereof, for example a subject with liver disease.

Figure 8A:
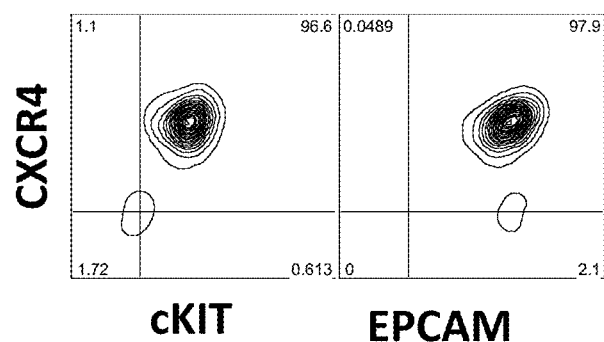
FIGS. 8A-8D (a) (b) (c) demonstrate that CHIR99021 can induce definitive endoderm cells.
Figure 8B:
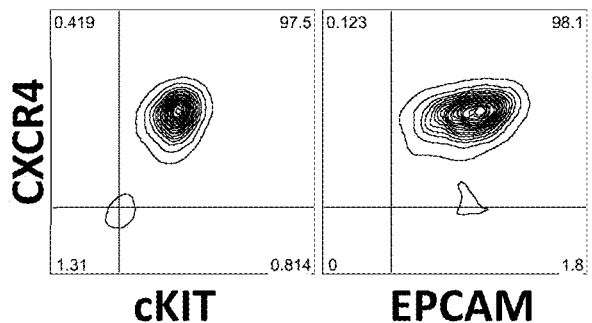
Figure 8C:
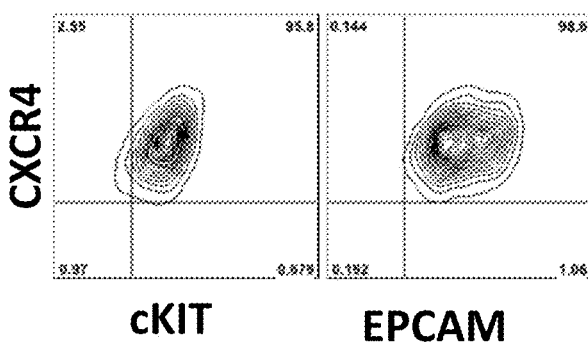
Figure 8D:
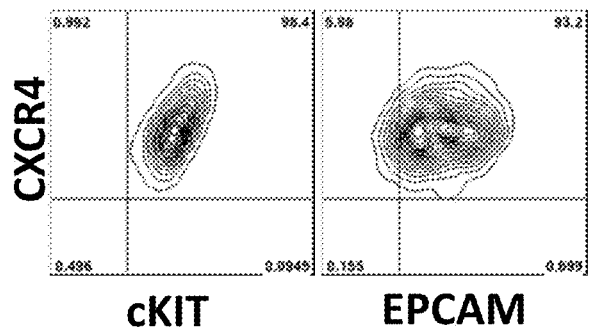
Figure 8E:
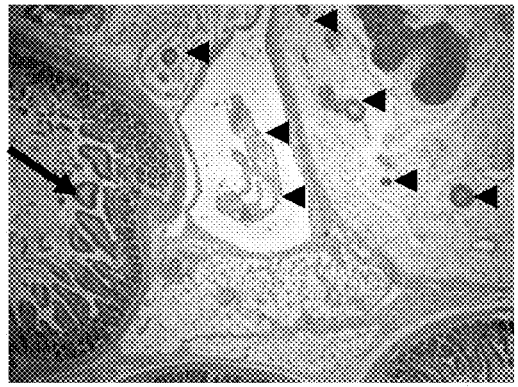
FIGS. 8E-8H show photomicrographs of ectopic liver tissue in NSG Mice.

It is demonstrated for example in FIGS. 8C-8E and described in Example 3 that ESC-derived transplanted hepatocyte cells engraft and are able to differentiate into hepatocytes and cells of the cholangiocyte lineage. Similarly Example 9 demonstrates that CFTR functional cholangiocytes can be produced in vitro and/or in vivo.

Accordingly, provided in an embodiment is a method of transplanting or treating a subject in need thereof with hepatocytes generated according to a method described herein. In an embodiment, the disclosure includes use of the cells generated according to a method described herein for treating a subject in need thereof of example a subject with liver disease and/or a biliary disease.

In an embodiment, a therapeutically effective amount is administered.

Takebe et al have demonstrated the generation of a vascularized and functional human livers from human iPSCs by transplantation of liver buds created in vitro.

In an embodiment, the cells obtained are derived from autologous cells, for example iPSCs generated from blood and/or skin cells from a subject. In an embodiment, the PSC can for example be iPSCs obtained from a biopsy, blood cells, skin cells, hair follicles and/or fibroblasts.

In another embodiment, hepatocytes and/or cholangiocytes generated using a method described herein are contacted with a test agent in a toxicity screen. CYPs are the major enzymes involved in drug metabolism and bioactivation. Various assays can be performed including drug-drug interaction assays, CYP inhibition assays and CYP induction assays.

For example, drugs may increase or decrease the activity of various CYP isozymes, either by inducing a CYP isozyme (CYP induction) or by directly inhibiting the activity of a given CYP (CYP inhibition). Changes in CYP enzyme activity may affect the metabolism and/or clearance of various drugs. For example, if one drug inhibits the CYP-mediated metabolism of another drug, the second drug may accumulate within the body to toxic levels.

In other embodiments, CYP inhibition screens can be conducted. As it is demonstrated that hepatocytes produced using a method described herein are shown to express CYP1A2, CYP2B6, CYP3A4, CYP2B6, CYP2C9, CYP2D6, and/or CYP7A1, screens for inhibition of one or more these isozymes for example using LC-MS/MS or fluorescent assays, can be conducted. CYP $IC_{50}$ and/or $K_i$ can be determined.

In yet other embodiments, induction of CYP enzymes can be assessed. For example, some compounds induce CYP enzymes resulting in increased metabolism of co-administered drugs that are substrates for the induced CYP enzymes. Such co-administered drugs can hence lose efficacy. CYP enzymes such as CYP1A2, CYP2B6, CYP2C and CYP3A4 are susceptible to induction. Catalytic activity and mRNA levels of the CYPs can be measured relative to controls with the result being expressed as a fold induction.

Further in other embodiments, drug metabolites can be assessed, e.g. the metabolite spectrum of a drug can be determined.

In an embodiment, different concentrations of the test agent are added to cells obtained using a method described herein, and the cells evaluated for survival, CYP 450 isozyme activity, CYP 450 isozyme mRNA level, and/or metabolite profile. The methods can be used for example to screen drugs generally or to assess a patient's specific toxicity to a drug.

In an embodiment, the functional hepatocytes and/or cholangiocytes are used in tissue engineering. For example, access to purified populations of functional hepatocytes and/or cholangiocytes allows generation of engineered constructs with defined numbers of functional hepatocytes and/or cholangiocytes. In other examples, access to purified populations of functional hepatocytes and/or cholangiocytes allows generation of bioartifical liver devices Alternatives to whole organ liver transplantation under investigation including using isolated cell transplantation, tissue engineering of implantable constructs and extracorporeal bioartificial liver devices (BAL) (reviewed in 51). As indicated on page 451 of this reference, "Their future use will depend on the choice and stabilization of the cellular component". Although cell lines and non-human cells have been assessed, there are difficulties with clinical use. Limitations in human functional hepatocytes and/or cholangiocyte sources have also hampered development of such devices.

As reviewed in 52, the liver is the main source of plasma proteins, including albumin, components of the complement system and clotting and fibrinolytic factors. Liver failure results in the inability to process low molecular weight substances, some of which are water soluble (ammonia, phenylalanine, tyrosine) but many of which are poorly water soluble and are transported in blood bound to transport proteins, mainly albumin (middle chain fatty acids, tryptophan and metabolites of it, endogenous benzodiazepines and other neuro-active substances, mercaptans, toxic bile acids, bilirubin, heavy metals and endogenous vasodilators). This leads to an accumulation of endogenous toxins that cause multiple secondary organ dysfunctions via direct cell toxicity (e.g., acute tubular necrosis due to jaundice), functional homeostatic alterations (e.g., hepatorenal syndrome as a consequence of hemodynamic dysregulation) or a combination of both (e.g., hepatic encephalopathy and coma). Combined dialysis and plasma exchange, selective plasma filtration and adsorption[27] or selective plasma exchange therapy techniques have been developed for liver support therapies. Plasma exchange techniques utilize for example highly selective membranes and albumin dialysis to increase the clearance of albumin-bound toxins along with water soluble toxins.

Obtaining functional hepatocytes and/or hepatocytes that produce albumin can be used with BAL. For example, if functional hepatocytes are obtained, it may not be necessary to perform albumin dialysis. ES/iPS derived hepatocytes that are able to generate albumin protein, which is a major protein secreted from liver, can also be used with BAL and albumin dialysis. The production of albumin from a human source is for example important in BAL. Albumin transports hormones, fatty acids and other compounds including toxic agents. The benefit of albumin dialysis is that toxic compounds binding Albumin can be eliminated from the blood stream. Human serum albumin, which is clinically used for liver and kidney disease is only obtained at present from donated blood. Generating albumin secreting cells and/or together with higher hepatic function activity, would be an advantage for establishing a BAL system.

In an embodiment, the methods are applied to patient specific disease hiPSCs and used for example to model liver disease. For example, liver or other cells from a patient with liver disease can be isolated, treated to obtain hiPSCs which can then be cultured and induced to differentiate to functional hepatocyte and/or cholangiocyte cells. These cells can be used to assess characteristics of the disease, such as the genes involved in the disease or the response to patients' immune cells.

For example, normal cells and patient specific disease hiPSCs can be induced to functional hepatocytes and/or cholangiocytes and compared. For example, genetic, epigenetic and proteomic analyses of pancreatic progenitors and beta cells from normal and patient specific hiPSCs can be conducted. Such detailed analyses can lead to the discovery of signaling pathways, transcriptional regulatory networks and/or cell surface markers that regulate normal human liver development as well as those that play a role in disease.

The term "subject" as used herein includes all members of the animal kingdom including mammals, and suitably refers to humans.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the terms "administering," "introducing" and "transplanting" are used interchangeably in the context of delivering cells (e.g. functional hepatocytes and/or cholangiocytes) into a subject, by a method or route which results in at least partial localization of the introduced cells at a desired site. The cells can be implanted directly to the liver, or alternatively be administered by any appropriate route which results in delivery to a desired location in the subject where at least a portion of the implanted cells or components of the cells remain viable.

Kit

A further aspect includes a kit. The kit can comprise one or more of the agonists, antagonists, maturation factors etc. e.g. described above, one or more medias, vessels for growing cells and the like, which can be used in a method described herein and/or cells expanded and/or prepared according to a method described herein. In an embodiment, the kit comprises instructions for use according to a method herein. In an embodiment, the kit comprises a population of cells produced herein, optionally with instructions, one or more of the agonists, antagonists, maturation factors etc. e.g. described above, including for example one or more medias, vessels for growing cells and the like.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

Examples Example 1

Endoderm Induction in EBs

Figure 1B:
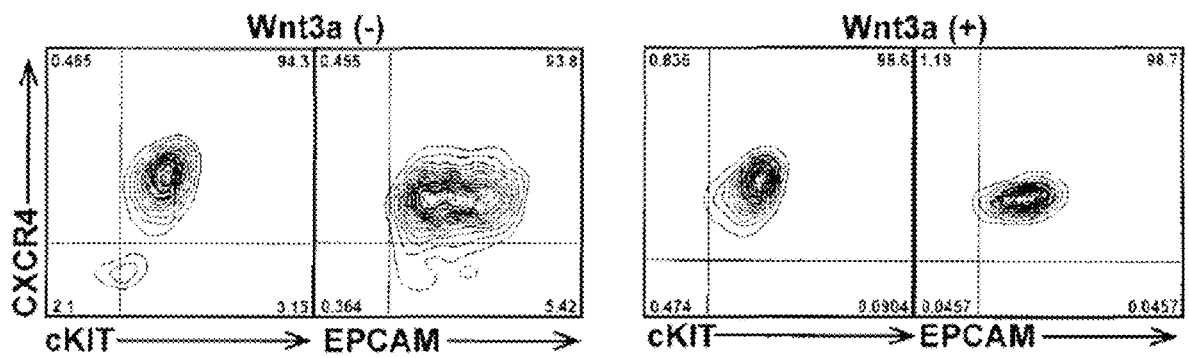

The strategy used to generate hepatic cells from hESCs using embryoid bodies (EBs) is shown in FIG. 1A. Similar to protocols using monolayer cultures[16], it involves specific steps that recapitulate the critical stages of liver development in the early embryo. EBs are formed from small aggregates by culture for 24 hours in low levels of BMP4, as previously described[18]. The EBs are subsequently exposed to high concentrations of activin A (hereafter referred to as activin) for five days to induce definitive endoderm, a population defined by expression of the surface markers CXCR4, CKIT and EPCAM and the transcription factors SOX17 and FOXA2. As shown in FIG. 1B, greater than 90% of the induced EB population co-expresses CXCR4 and CKIT or CXCR4 and EPCAM following five days of activin induction (six days total culture). Intracellular flow cytometric analyses revealed that more than 90% of the population expressed SOX17 and greater than 80% was FOXA2$^+$.

Figure 1C:
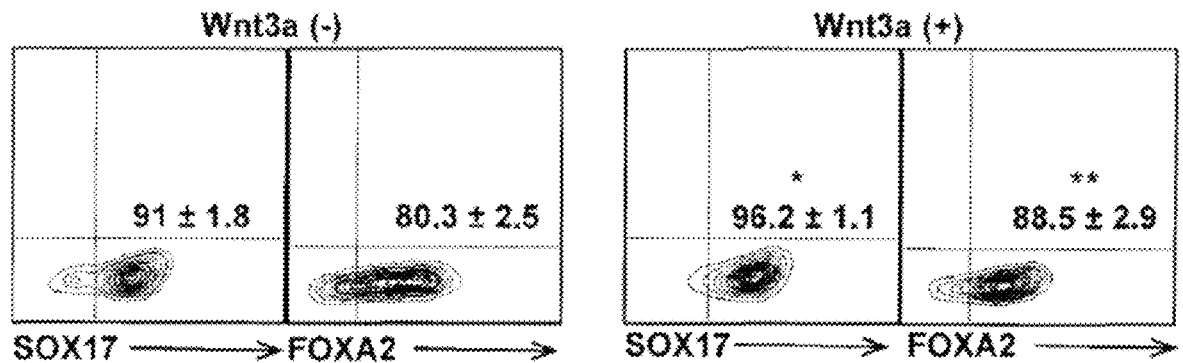
Figure 1D:
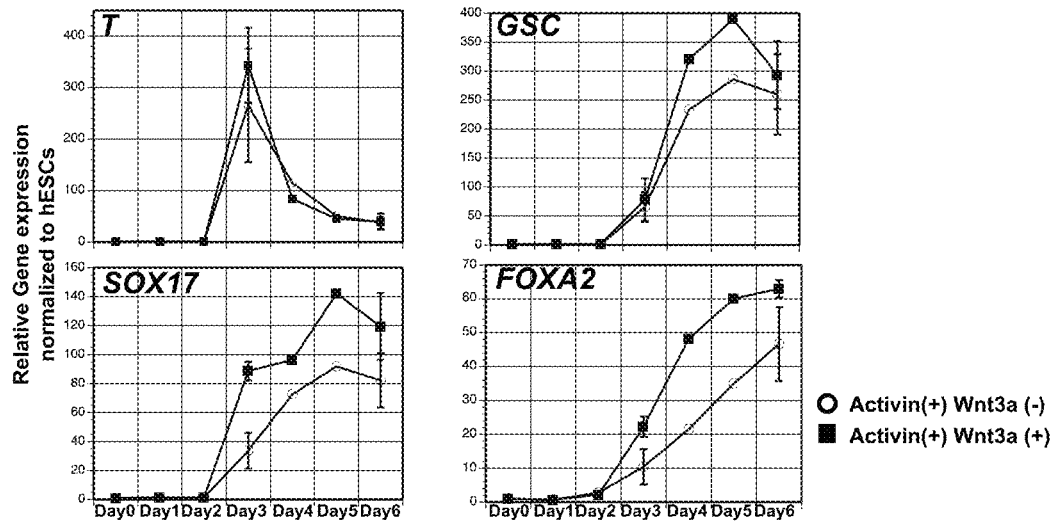
Figure 1E:
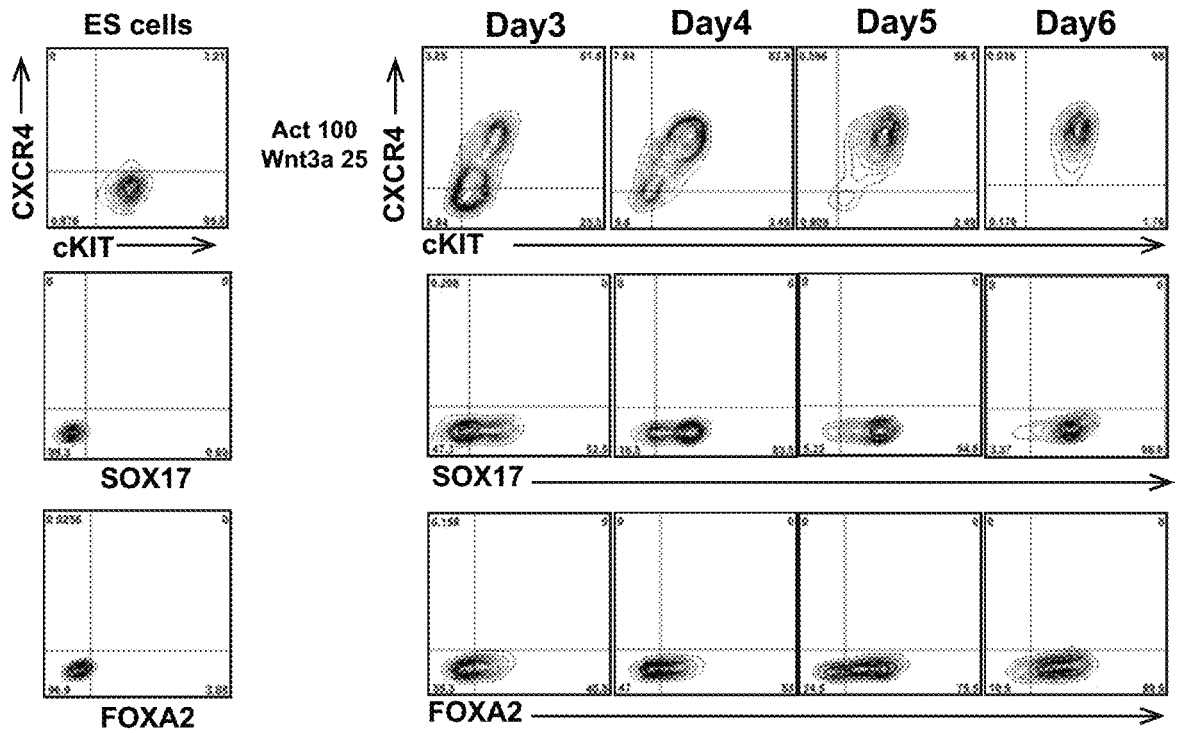
Figure 1F:
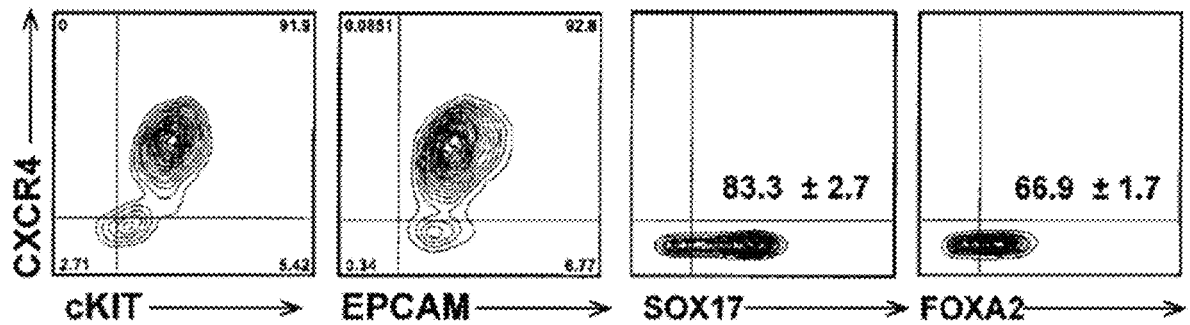

Studies using monolayer induction protocols demonstrated that Wnt signaling augments activin-induced endoderm development, likely due to enhancement of anterior primitive streak formation[10]. Addition of Wnt3A to the activin-induced EB cultures led to reproducible increases in the proportion of CXCR4$^+$, SOX17$^+$ and FOXA2$^+$ cells within the EBs (FIG. 1c). With the increase in CXCR4 expression, the proportion of CKIT$^+$CXCR4$^+$ and CXCR4$^+$EPCAM$^+$ cells increased to greater than 95% of the population. Molecular analyses showed elevated levels of SOX17 and FOXA2 expression in the Wnt induced EBs, confirming the flow cytometric data (FIG. 1d). The addition of Wnt did not accelerate the decline in expression of Oct3/4 but did lead to an increase in T (brachyury) expression at day three and Goosecoid (GSC) expression at days four and five (FIG. 1d). Wnt enhances primitive streak formation as demonstrated in the mouse ESC model 19 and in monolayer hESC-derived cultures[10]. Kinetic analyses showed a rapid and dynamic increase in the proportion of CKIT$^+$CXCR4$^+$, SOX17$^+$ and FOXA2$^+$ positive cells between days 3 and 6 of differentiation (FIG. 1e). Endoderm induction in the EBs was influenced by the base culture media used. StemPro34 supported more efficient endoderm induction than neural basal media that we used previously (FIG. 1f). The induction of highly enriched endoderm is an important first step in the efficient and reproducible generation of hepatocyte-like cells from hPSCs. Induction levels of for example of at least 90% CXCR4$^+$CKIT$^+$ and 80% SOX17$^+$ cells were found to result in optimal hepatic lineage development.

Duration of Nodal/activin Signaling Impacts Hepatic Development.

Figure 2A:
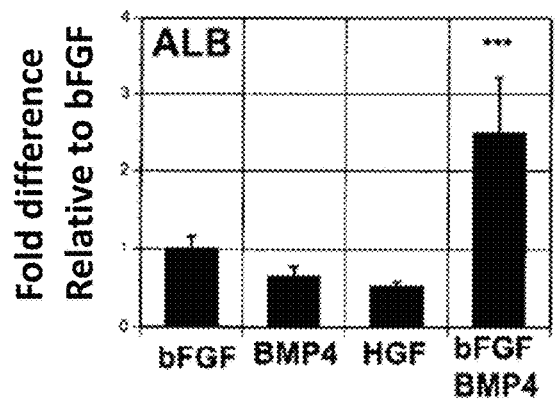
FIG. 2A shows an RT-qPCR analysis of albumin expression in monolayer cultures specified with the indicated cytokines. Cells were treated with the different factors (bFGF 10 ng/ml; BMP4 50 ng/ml; HGF 20 ng/ml; or bFGF 20 ng/ml plus BMP4 50 ng/ml) from 6 days to day 12 and then cultured with DEX, HGF and OSM and analyzed at day 24. Bars represent the standard deviation (SD) of the mean of three independent experiments. Values are determined relative to TBP and presented relative to expression in bFGF (20 ng/ml) culture, which is set a one. *** P<0.001 as compared with the culture treated bFGF. Student's t-test, n=3.
Figure 2B:
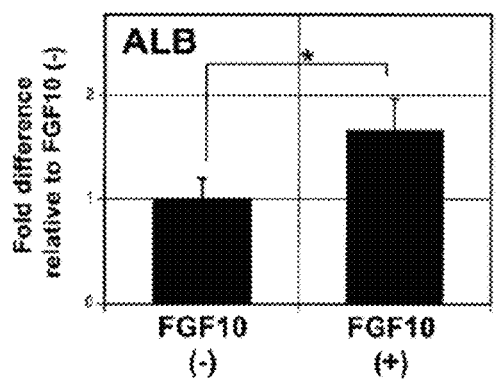
FIG. 2B shows an RT-qPCR analysis of albumin expression in populations specified in the presence and absence of FGF10. Cultures were treated (or not) with FGF10 (50 ng/ml) plus BMP4 (50 ng/ml) between days 6 and 8. At this stage, the FGF10 was removed and the cells cultured in bFGF/BMP4 between 8 and 12. Bars represent the standard deviation (SD) of the mean of three independent experiments. Values are determined relative to TBP and presented relative to expression in FGF10 (−) culture, which is set at one. * P<0.05, Student's t-test, n=3.

To specify the CXCR4$^+$CKIT$^+$ population to a hepatic fate, day six EBs were dissociated and the cells plated as a monolayer on Matrigel coated plates in the presence of FGF10 and BMP4 for 48 hours and then in bFGF and BMP4 for six days. It has been previously demonstrated in mouse[20] and human ESC differentiation cultures[16] that FGF and BMP are important for human and mouse specification. In Si-Tayeb et al, FGF2 and BMP4 were combined and 80-85% of cells generated expressed albumin. It was found that the combination of these two factors was required for optimal hepatic induction under the tested conditions (FIG. 2a). The FGF10/BMP4 step was included as it was found to increase albumin expression compared to bFGF/BMP4 alone in the differentiation cultures (FIG. 2b). With these induction conditions, substantial numbers of albumin positive cells consistently developed in the cultures between days 12 and 24 of differentiation.

While the BMP4/FGF specification step promotes hepatic development, analyses of cultures at day 10 revealed that the proportion of SOX17$^+$ and FOXA2$^+$ cells within the culture had decreased significantly, from more than 90% to approximately 50% (FIG. 3a). Without being bound by theory, this decrease suggested that either the day six population was contaminated with non-endoderm cells that preferentially expanded in the presence of FGF and BMP4 or that the endodermal fate of the cells was not yet fixed, and as a consequence some adopted another fate under the conditions used. It was previously demonstrated that prolonged activin/nodal signaling was required for establishing an endoderm fate from anterior primitive streak cells in an in vitro mouse ESC differentiation system[19]. It was not known if prolonged signaling would be useful with human PSC. The effect of increasing the duration of this signaling pathway was extended in the human system by culturing the monolayer cells for two days in activin prior to the FGF/BMP4 specification step. When induced with activin for an additional two days, the proportion of SOX17$^+$ and FOXA2$^+$ cells measured at day 12 was significantly higher than in the non-treated group (FIG. 3a). Without being bound by theory, since the total cell number was lower in the treated population (FIG. 3b) it is possible that activin signaling at this stage preferentially supports the survival of endodermal cells.

Figure 3F:
Figure 3G:
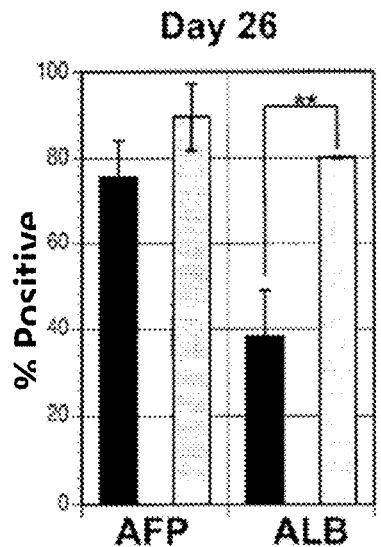

The extended activin treatment maintained the CXCR4$^+$CKIT$^+$ population until day 8 of culture (FIG. 3c) and resulted in higher levels of expression of genes indicative of hepatic progenitor (hepatoblast) development, including HEX, AFP, ALB and HNF4a at day 26 of culture (FIG. 3d). Cultures generated from non-treated CXCR4$^+$CKIT$^+$ endoderm contained contaminating mesoderm as demonstrated by the expression of MEOX1, MESP1, CD31 and CD90 and by the presence of CD90$^+$ mesenchymal cells and CD31$^+$ endothelial cells at day 24 (FIG. 3d,e). Populations derived from the activin-treated endoderm showed reduced expression of the mesoderm genes, had a higher portion of EPCAIVT cells, no detectable CD31$^+$ cells and a much smaller CD90 population (FIG. 3e). Consistent with these differences, a significantly higher proportion of albumin positive cells was observed in the treated compared to the non-treated population at day 26 of culture (FIG. 3f,g). Interestingly, the proportion of AFP positive cells was not different between the two groups. Without being bound by theory, this suggests that at this stage, its expression in the non-treated population may not be hepatic specific.

Aggregation Promotes Hepatic Maturation

Figure 4A:
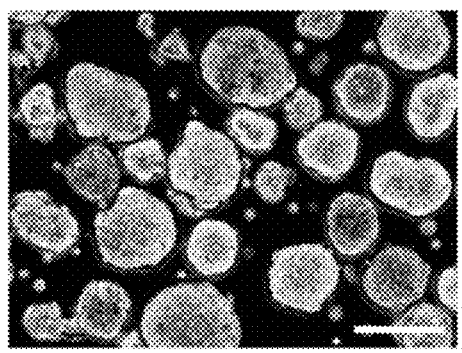
FIGS. 4A-4D show that aggregation promotes hepatic maturation.
Figure 4B:
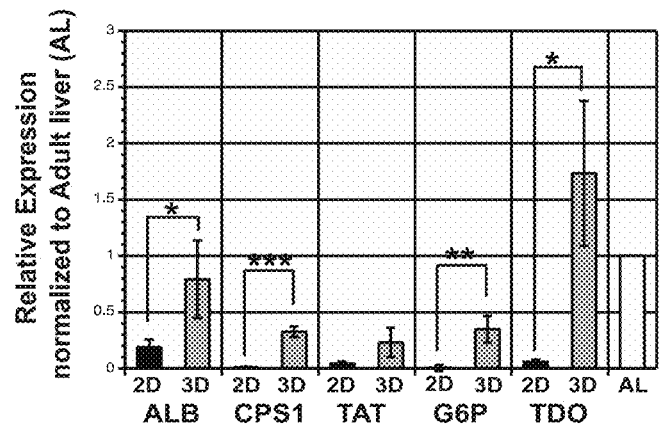
Figure 4C:
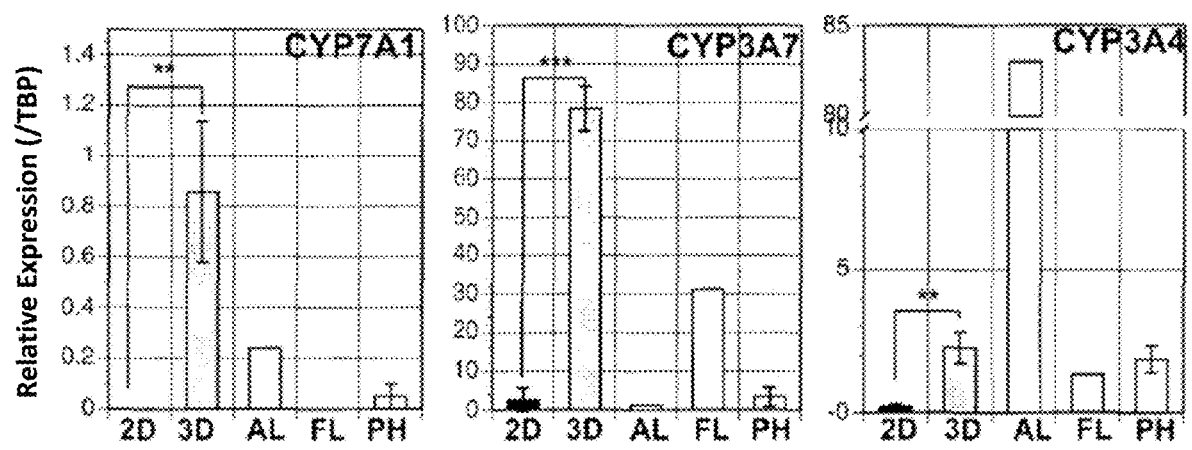

Although prolonged activin/nodal signaling promoted hepatic development, the expression levels of genes such as albumin and HNF4α were significantly lower in the hESC-derived population compared to adult liver, suggesting that the cells in the day 26 cultures are still immature. Previous studies have shown that cell aggregation can maintain the differentiated phenotype of primary hepatocytes[21][23] in culture and promotes some degree of maturation of hESC-derived hepatic cells[24]. The role of aggregation on maturation of the day 26 hepatoblast population derived from activin-treated endoderm was investigated next. Aggregates were generated from the monolayer by a combination of enzymatic treatment and manual dissociation and then cultured in the presence of HGF, Dexamethasone (Dex) and Oncostatin M (OSM) for six days (FIG. 4a). Aggregation did impact differentiation and led to an increase in the expression of a number of genes associated with liver function including ALB (albumin), CPS1 (Carbamoyl-phosphatase synthase 1), TAT (Tyrosine aminotransferase), G6P (Glucose 6 phosphatase) and TDO (Tryptophan 2,3-dioxygenase) (FIG. 4b). In some instances the levels were similar to (ALB) or higher than (TDO) the levels found in adult liver (FIG. 4b). Aggregation also increased the expression of several cytochrome P450 genes including CYP7A1, CYP3A7 and CYP3A4. The levels of CYP3A4 were similar to that in found in primary hepatocytes but well below that in adult liver (FIG. 4c). Expression of other P450 genes including CYP1A2 and CYP2B6 as well as the Phase II enzyme UGT1A1 were not induced to any significant level.

Figure 4D:
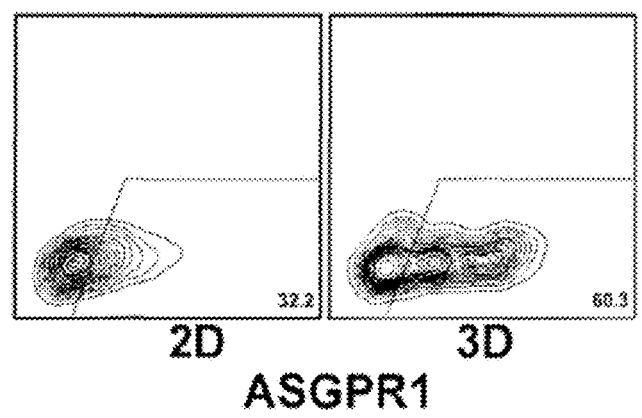

The cell surface marker asialo-glycoprotein receptor-1 (ASGPR-1) is found on mature hepatocytes and has been shown to mark maturing cells in hESC-differentiation cultures. Aggregation resulted in a dramatic increase in the proportion of ASGPR-1+ cells detected in the culture, consistently yielding populations that contain greater than 50% positive cells (FIG. 4d). Immunostaining showed that ASGPR-1 and E-cadherin was detected on albumin+ day 32 aggregate cells. Collectively, these findings show that the simple process of aggregation into 3-D structures promotes changes indicative of hepatic maturation.

cAMP Signaling Induces Maturation of hESC-Derived Hepatocyte-Like Cells.

Figure 5A:
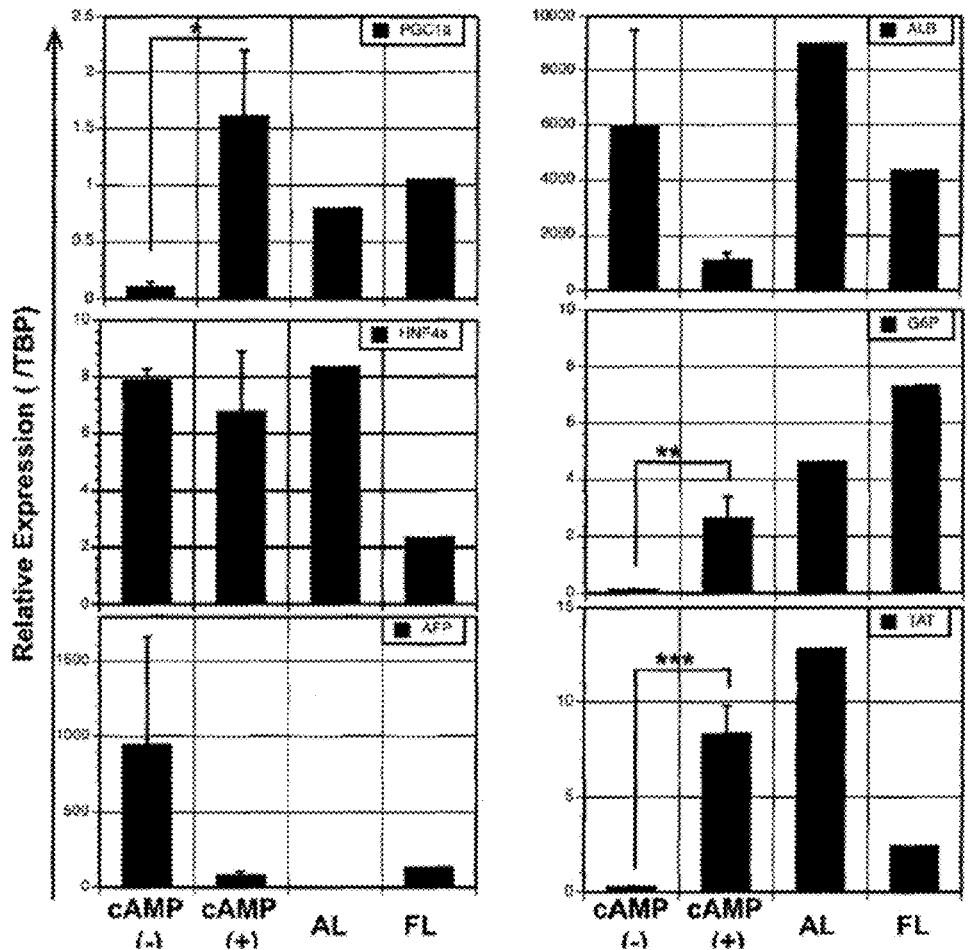
FIGS. 5A-5D show that cAMP signaling induces maturation of hESC-derived hepatocyte-like cells.
Figure 5B:
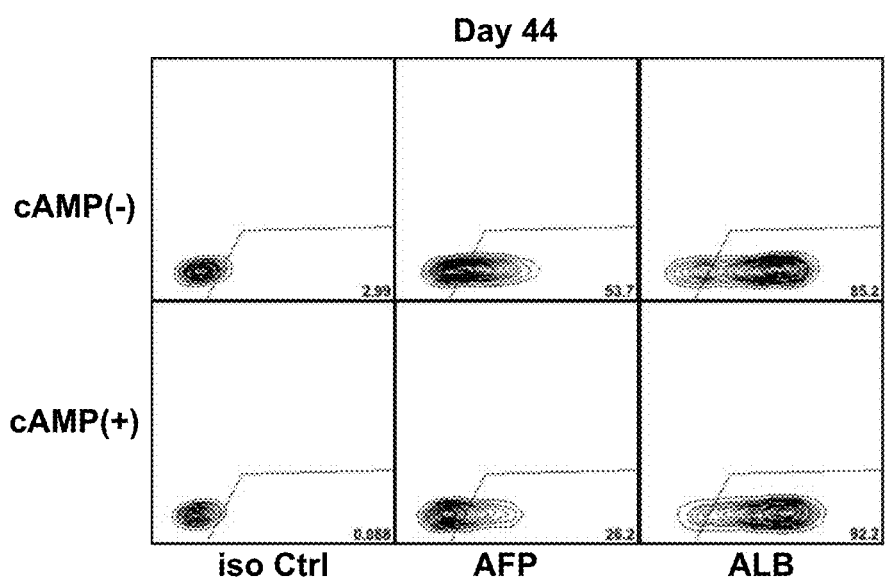
Figure 5C:
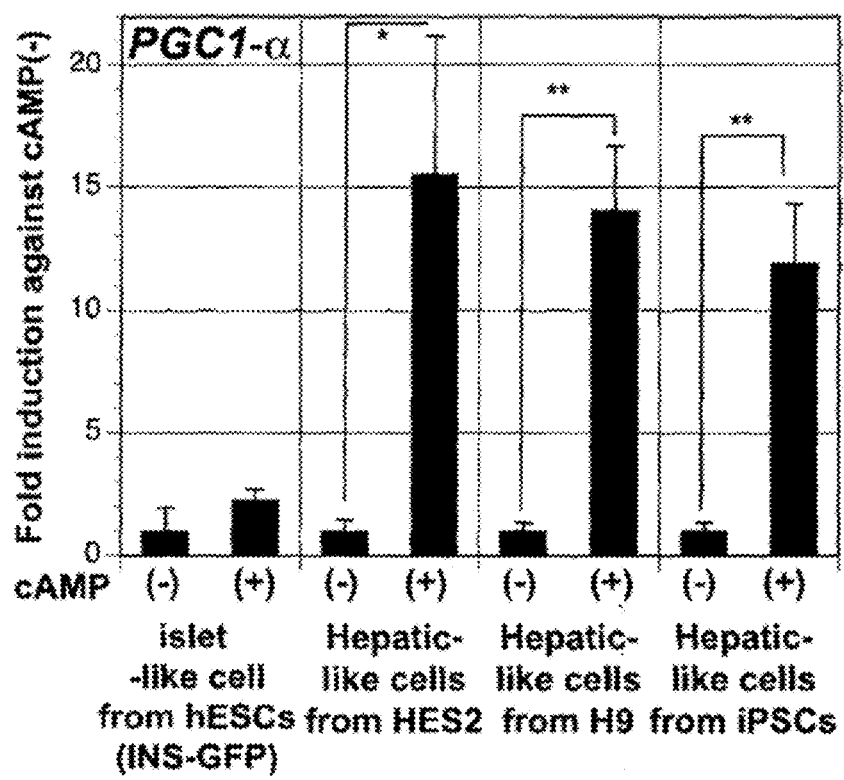

To further mature the cells, the role of cAMP signaling was investigated. Studies using hepatic cell lines have shown that activation of this pathway can induce hepatic gene expression, in part through the induction of the peroxisome proliferator-activated receptor gamma coactivator-1-alpha (PGC1-a), a coactivator that functions together with HNF4a to regulate the expression of many genes involved in hepatocyte function 25 28. To determine whether cAMP signaling could promote maturation of the hESC-derived hepatocyte-like cells, 8-bromoadenosine-3'5"-cyclic monophosphate (8-Br-cAMP), a cell permeable analogue of cAMP, was added to the hepatic aggregates from day 32 to 44 of culture. Treatment with 8-Br-cAMP significantly enhanced the expression of PGC1-a (15-fold), but not that of HNF4α in the hESC-derived hepatic cells (FIG. 5a). 8-Br-cAMP also induced expression of G6P and TAT an average of 25 and 33 fold respectively, to levels that approximate those in the adult liver (FIG. 5a). In contrast, the expression levels of AFP and ALB were downregulated by 8-Br-cAMP. Flow cytometric analyses confirmed the AFP expression analyses and showed a reduction in the number of AFP positive cells (54% to 26%) in the 8-Br-cAMP treated aggregates, compared to the non-treated controls. The proportion of ALB positive cells was not reduced in spite of the fact that the levels of mRNA declined (FIG. 5b). Without being bound by theory, these differences could reflect differences in RNA vs. protein expression. Other tissues, such as the pancreas, also express PGC-1a. However, in contrast to the observed induction in hepatic cells, expression of PGC1-a was not induced by cAMP signaling in hESC-derived insulin positive pancreatic cells (FIG. 5c) indicating that this response may be tissue specific.

Figure 5D:
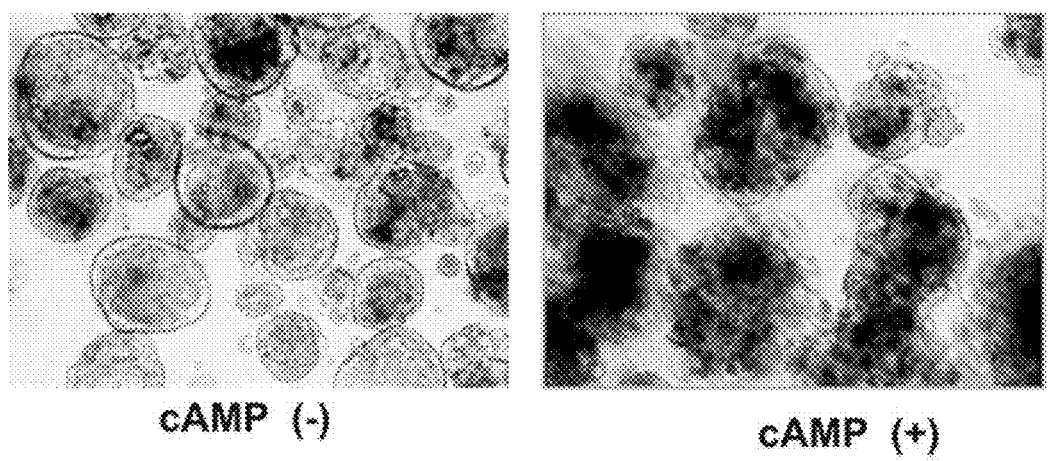

Cellular uptake of Indocyanine green (ICG) is considered to be a characteristic of adult hepatocytes[29] and is used clinically as a test substrate to evaluate hepatic function[30]. cAMP signaling dramatically increased the proportion of cells that displayed this activity as demonstrated by the observation that almost all treated aggregates stained with ICG (FIG. 5d).

Confocal microscopy was used to assess co-expression of ALB and AFP or ALB and HNF4a in day 44 aggregates cultured in the presence and absence of 8-Br-cAMP. Immunostaining analyses were consistent with the flow cytometry data and showed that cAMP-treated aggregates expressed similar levels of ALB but lower levels of AFP compared with the non-treated ones.

Figure 6A:
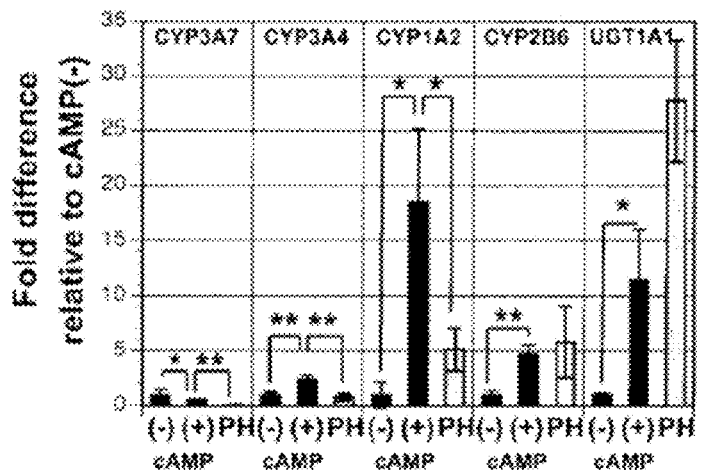
FIGS. 6A-H show that cAMP signaling increases metabolic enzyme activity in hESC-derived hepatocytes.

The levels of albumin (ALB) secreted by hESC-derived monolayer and aggregate populations, as well as by HepG2 cells, Huh7 cells and cryopreserved hepatocytes (PH, lot OSI) was detected using an ELISA assay. The levels of HNF4 protein in both aggregate populations were comparable, confirming the PCR analyses. Albumin secretion by the hESC-derived cells was not impacted by 8-Br-cAMP treatment but was dramatically enhanced by the aggregation step. Albumin secretion was detectable at day 20 in low levels in monolayer cultures but was dramatically increased (about 5 fold) in day 32 aggregated cultures. Only low levels were detected in HepG2, Huh7 and PH cells. By contrast, the capacity to take up indocyanine green (ICG), a characteristic of adult hepatocytes (Stieger et al., 2012) was enhanced by cAMP signaling. ICG uptake and release by cAMP-treated and non-treated was measured in day 44 aggregates.

cAMP Signaling Increases Metabolic Enzyme Activity in hESC-Derived Hepatocytes.

cAMP signaling also induced changes in the expression pattern of key Phase I cytochrome P450 genes, notably a reduction in the levels of expression of the fetal gene CYP3A7, and a significant increase in expression of the adult genes CYP3A4 (2.5-fold), CYP1A2 (18-fold) and CYP2B6 (4.7-fold) (FIG. 6a). UGT1A1, an important Phase II enzyme, was also significantly induced (11-fold) by 8-Br-cAMP (FIG. 6a). The induced levels of CYP3A4 and CYP1A2 were significantly higher than those found in primary hepatocytes whereas the levels of CYP2B6 were similar in the two populations. UGT1A1 expression in the hESC-derived population did not reach the levels found in the primary hepatocytes. Without being bound by theory, given that expression of CYP1A2 is restricted to the liver and only detected after birth[31], these findings suggest that cAMP signaling promotes differentiation beyond the fetal stage of development.

Figure 6B:
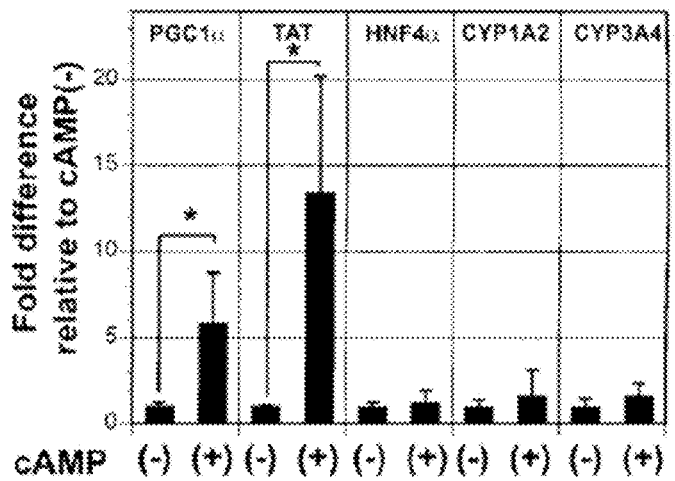
Figure 6C:
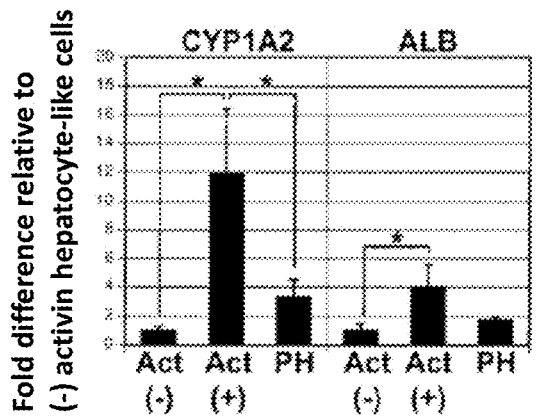
Figure 6D:
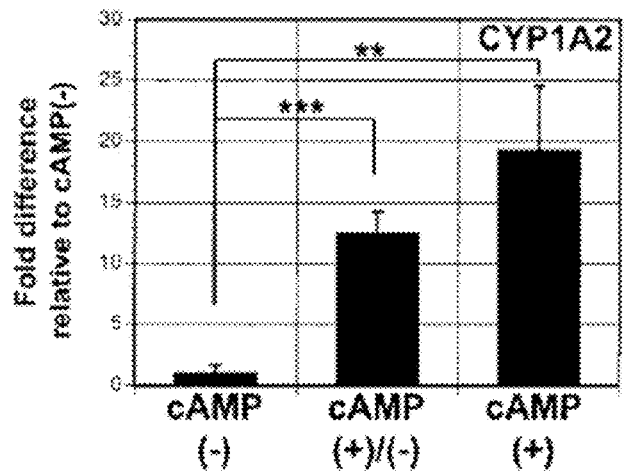

The inductive effects of cAMP signaling on the P450 genes were only observed in cells in the 3D aggregates, as little increase in expression of CYP1A2 and CYP3A4 was detected when it was added to monolayer cultures (FIG. 6b). Expression of PGC1-α and TAT was induced in the monolayer format, likely due to the fact that the promoter regions of these genes contain cAMP-response element binding protein (CREB) sites. To further define variables that influence the cAMP response aggregates generated from extended activin treated endoderm were compared to those generated from endoderm without the additional two days of activin/nodal treatment. Little induction of CYP1A2 and ALB was observed in the aggregates from the non-treated population (–Act), suggesting that cAMP signaling is only effective on highly enriched, appropriately patterned cells (FIG. 6c). For the above studies, 8-Br-cAMP was included in the cultures for 12 days (day 32-44). To determine whether the changes in gene expression are dependent on continuous signaling, cells induced with 8-Br-cAMP for six days and then maintained in the absence of 8-Br-cAMP for the remaining six days were compared to those cultured for the entire 12 days in 8-Br-cAMP (FIG. 6d). Expression of CYP1A2 was maintained following the shorter induction time, indicating that the higher levels of expression are not dependent on continuous signaling but rather reflect changes indicative of hepatocyte maturation.

Figure 6E:
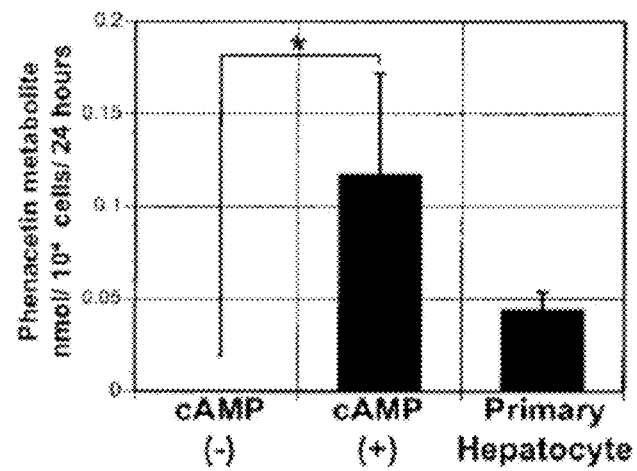
Figure 6F:
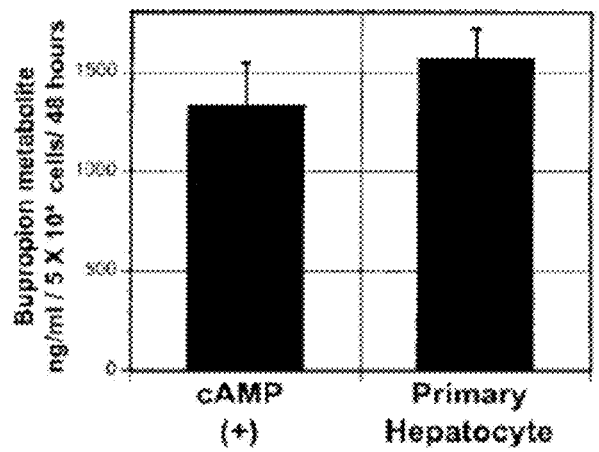
Figure 6G:
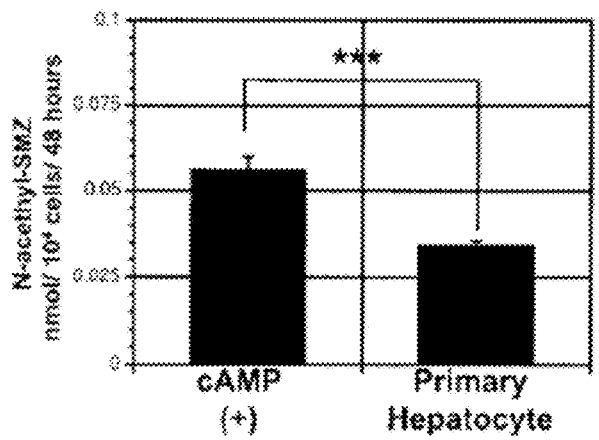
Figure 6H:
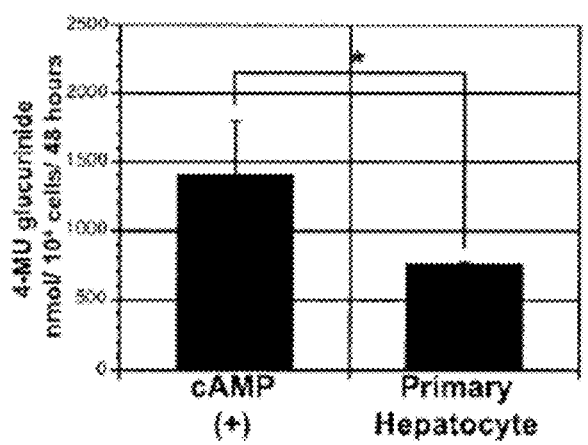

To investigate the functional activity of the P450 enzymes, the ability to metabolize isozyme-selective marker drugs was measured by high performance liquid chromatography (HPLC). The 8-Br-cAMP-treated cells O-deethylated the CYP1A2-selective substrate phenacetin at levels as high as primary cultured hepatocytes (FIG. 6e). Non-treated cells did not show detectable activity. CYP2B6 activity as measured by the hydroxylation of bupropion was also detected in the 8-Br-cAMP-treated cells, at levels comparable to those found in primary hepatocytes (FIG. 60. Analyses of phase II metabolic enzymes, including the arylamine A/-acetyltransferases NAT1 and/or NAT2 (FIG. 6g) and UDP-glucuronosyltransferase (UGT) (FIG. 6h) revealed activity higher than that of primary cultured hepatocytes, indicating that cAMP signaling induced the up-regulation of expression of a broad range of enzymes, consistent with maturation of the population. Together, these observations indicate that cAMP signaling promotes maturation of the hESC-derived hepatocyte-like cells in the 3-D aggregates.

Additionally, the inducibility of the metabolic activity of two of the key enzymes, CYP1A2 and CYP3A4, was also evaluated. 8-Br-cAMP-treated cells were able to metabolize the CYP1A2-selective substrate phenacetin. Induction of the cells with lansoprazole for 72 hours resulted in a 3.4-fold increase in this activity. The non-treated (8-Br-cAMP) cells had low levels of activity that were not inducible. Two independent primary hepatocyte samples showed lower or comparable levels of basal metabolic activity, but did display higher levels of induction (18- and 9-fold). CYP3A4 activity was measured by the ability of the cells to metabolize testosterone to 6β-hydroxyl testosterone. 8-Br-Camp treated cells displayed this activity. Addition of the CYP3A4 inducer rifampicin increased the activity 2.2-fold, indicating that this enzyme was also inducible in the hESC-derived cells. As observed with CYP1A2, little CYP3A4 activity was detected in the non-induced cells. The primary hepatocytes showed low but significant levels of CYP3A4 induction.

Hepatic Specification and Maturation from Other hPSC Lines

To determine whether the approach detailed above is broadly applicable to different human pluripotent stem cell lines the protocol was used to differentiate the hESC lines H9 and H1 as well as an induced pluripotent cell (iPSC) line 38-2 to a hepatic fate. Day six EBs from all three lines contained high proportions of CKIT$^+$CXCR4$^+$ and CKIT$^-$EPCAM* cells following the Wnt3a/activin induction step (FIG. 7a). Although the proportion of EPCAIVT cells was high in all EBs, the H9-derived cells expressed substantially higher levels of EPCAM than cells generated from the other lines. The levels of EPCAM expression correlated with the degree of endoderm induction, as greater than 95% of the H9-derived population expressed SOX17$^+$ and FOXA2$^+$ whereas only 65-70% of the iPSC-derived cells expressed these transcription factors (FIG. 7a). These findings indicate that surface marker analysis alone is not sufficient to monitor endoderm development and that quantitative analyses of SOX17 and FOXA2 expression is required to measure induction of this germ layer. As observed with the HES2 cells, extended activin/nodal signaling improved hepatic development of the CKIT$^+$CXCR4$^+$ population from each line (FIG. 7b). However, the duration of activin treatment necessary to generate significant levels of ALB expression varied between cell lines. Whereas higher levels of ALB expression were achieved following two days of activin treatment with H9-derived cells, both H1 and 38-2 cells required four days of additional activin signaling. With this treatment, it was possible to generate cultures consisting of 90%, 85% and 70% ALB$^+$ cells from the H9, H1 and 38-2 cell lines, respectively (FIG. 7c). H9-derived cells at day 26 of differentiation showed a cobblestone morphology very similar to that of cultured hepatocytes FIG. 7d).

Addition of 8-Br-cAMP did induce significant levels of expression of CYP3A4 (16-fold), CYP1A2 (100-fold), and CYP2B6 (10-fold) and the Phase II enzyme UGT1A1 (16-fold) in the HQ-derived aggregates (FIG. 7e). The magnitude of induction was substantially greater than in the HES2-derived cells and the levels of expression of CYP1A2 and CYP3A4 were significantly higher than those in the primary hepatocytes. The reason for the differences in induction between the two hESC lines is currently not known. 8-Br-cAMP also induced the expression of these enzymes in hiPSC-derived aggregates to levels as high as those in primary hepatocytes s (FIG. 7e).

As observed with the HES2 line, the H9-derived cells possessed that lansoprazole-inducible CYP1A2 activity. H9 and iPSC-derived cells also showed CYP3A4 activity that was inducible with rifampicin. Inducible CYP1A2 activity was not detectable in the iPSC-derived cells, possibly reflecting suboptimal differentiation of this population.

Microarray Analyses of cAMP Stimulated Hepatic Populations.

To further evaluate the consequence of cAMP induction and to assess the developmental status of the hESC-derived hepatic populations relative to primary hepatocytes, a microarray analysis was carried out to compare the global expression profile of the different populations. A total of 23038 filtered transcripts were used in the final analysis. A two-way unsupervised hierarchical cluster analysis revealed that the three groups appear as distinct populations. The three cAMP-induced populations were the most similar to one another, whereas the three primary hepatocyte populations showed the most divergent expression patterns. A FDR corrected ANOVA (q<0.05) was used to identify 784 transcripts that showed the most statistically significant variability across all three sample groups. A hierarchically clustered visualization of these data identified clusters of highly expressed transcripts in each of the biological groups. These clusters consisted of 181 transcripts in the primary hepatocytes, 106 transcripts in the 8-Br-cAMP-induced cells and 80 transcripts in the non-treated cells. Genes enriched in 8-Br-cAMP-induced cells included most of the key P450 enzymes, as well as gene ontogeny categories of those involved in many aspects of liver function including gluconeogenesis, glucose homeostasis and lipid metabolism. The cluster expressed at highest levels in the primary hepatocytes consisted of immune system, inflammatory related and MHC genes. The cluster detected in the non-induced hESC-derived cells did not contain any enriched gene ontology categories.

For a more detailed comparison of the populations, selected sets of transcripts that encode proteins involved in key aspects of liver function were analyzed. These included a subset of Phase I and II drug metabolizing enzymes, transporters, coagulation factors, lipoproteins, nuclear receptors and transcription factors and general liver enzymes and other functional molecules. Analyses of these data revealed that many of the genes are expressed at comparable levels in the 8-Br-cAMP-treated hESC-derived cells and the primary hepatocytes. Select genes in each category are expressed at significantly higher levels in the 8-Br-cAMP treated cells compared to the untreated cells or the primary hepatocytes. These include the Phase I enzymes CYP1A2 and CYP3A4, confirming the qPCR and functional studies, the Phase II enzyme SULT2A1, the transporter SLC01B1, the general liver enzymes TAT, G6P and TDO (responsible for tyrosine metabolism, gluconeogenesis and tryptophan metabolism, respectively), the surface receptor ASGPR-1, and ALB. Since cellular uptake of ICG in hepatocytes is regulated by the organic anion transporters SLC01B1 and SLC01B3 and the Na$^+$-independent transporter SLC10A1[29] induction of their expression is consistent with the findings that cAMP treated aggregates showed higher levels of ICG uptake. Taken together, these data from the microarray analyses indicate that induction of the hepatoblast-stage aggregates with cAMP results in global expression changes indicative of hepatocyte maturation. Based on these analyses, the hESC-derived hepatic cells generated by this approach appear to represent a developmental stage at least equivalent to that of primary human hepatocytes.

Discussion

For hPSC-derived hepatocytes to be useful for drug metabolism analyses and for transplantation for the treatment of liver disease, the cells must be relatively mature and display many characteristics of adult hepatocytes including measurable levels of key Phase I and Phase II drug-metabolizing enzymes. To date, a number of different studies have shown that it is possible to generate immature hepatic lineage cells from both hESCs and hiPSCs using staged protocols designed to recapitulate critical developmental steps in the embryo. The success of these studies reflects the fact that the pathways controlling the early stages of differentiation are reasonably well defined. In contrast, the factors and cellular interactions that control hepatocyte maturation are poorly understood, and as a consequence only a few studies have reported the development of metabolically functional cells. Duan et al[12] showed that it was possible to derive hepatic cells from H9 hESCs that displayed levels of CYP1A2, CYP3A4, CYP2C9 and CYP2D6 enzyme activities comparable to those found in primary hepatocytes. Duan et al used serum in their methods which comprises numerous factors some of which vary between batches of serum. The factors responsible were undefined. While these findings indicate that relatively mature hESC-derived hepatocytes can be generated, the study did not provide any details on the pathways that promote maturation nor did it demonstrate that the strategy is broadly applicable to other hPSC lines. As shown in FIG. 6 of Duan et al, they measured metabolism drugs in hepatocyte from human ES cells (H9). Phenacetin induces and provides an assessment of CYP1A2 activity, Midazolam, Bufuralol and Diclofenac induces and provides an assessment of CYP3A4, and CYP2B6 and CYP2D6, respectively. In for example the HES2 cell line described herein, et al almost equivalent levels of enzyme activity (CYP1A2 and CYP2B6) compared to primary hepatocytes was seen. In qPCR analysis, the level of expression of CYP1A2 and CYP2B6 in H9 cells was 5-8 fold higher than those found in HES2 cell line. The methods described herein result in cells that more closely resemble primary hepatocytes in terms of CYP enzymes CYP1A2 and CYP2B6. Similarly almost the same or comparable level of CYP2D6 expression is seen in cells generated using the present methods compared to primary hepatocyte.

Several other groups have shown that forced expression of specific transcription factors in hESC-derived populations alone or together with co-culture with Swiss 3T3 cells can promote maturation resulting in the generation of cells that express key metabolic enzymes[32,34]. A major drawback of this approach, however, is the need for viral transduction for every experiment and the variability that results from these manipulations including differences in efficiencies in infection and in establishing appropriate levels of expression of potent transcription factors. When compared to primary hepatocytes, the expression levels in the hESC-derived populations generated through this approach were considerably lower than found in primary hepatocytes.

Herein, insights into pathways that regulate maturation are provided. It is also demonstrated that the combination of 3D aggregation and cAMP signaling plays a pivotal role in the maturation of hepatoblasts. Further, activin/nodal signaling following endoderm induction is essential for the optimal generation of the hepatoblast progenitor population, and enriched progenitor populations are useful for the derivation of mature populations. The combination of these three distinct steps for example results in the generation of hepatocyte-like cells that display expression profiles and levels of functional metabolic enzymes similar to those found in primary adult hepatocytes.

The observation that sustained activin/nodal signaling within the CXCR4$^+$C-KIT$^+$ population is useful for the generation of mature hepatocytes highlights the importance of appropriate manipulation of early stage cells for the efficient generation of mature cells. The effect of extended activin/nodal signaling between days 6 and 8 of differentiation (for HES2 cells) impacted gene expression patterns and the proportion of albumin-positive cells detected at day 26 of culture. This step also promoted the development of a population of hepatic cells that, in response to cAMP, mature to give rise to metabolically functioning hepatocytes. This additional signaling step is not compensation for poor endoderm induction, as the day six EB target population consisted of greater than 95% CXCR4$^+$CKIT$^+$EPCAM$^+$ SOX17$^+$ cells. Rather, without being bound by theory, it appears to reduce contaminating mesoderm-derivatives (CD90$^+$ and CD31$^+$ cells), possibly due to the inability of activin to induce these lineages or promote their survival in the absence of BMP or FGF. In addition to reducing mesodermal contamination, the additional activin culture step may also play a role in appropriately patterning the endoderm to a ventral foregut fate, as this pathway is known to play role in the anterior-posterior patterning of the gut tube[35,36]. It was previously demonstrated that sustained activin/nodal signaling also impacted pancreatic development from hESCs[18].

In particular embodiments, the maturation stage of the protocol involves two distinct, but interdependent steps. The first is the generation of 3D aggregates. Previous studies have shown that 3D culture can improve hepatocyte survival and the maturation of mouse and human primary fetal hepatocytes[24,37,38]. Recently, Miki et al. reported that 3D culture in perfusion bioreactors can improve the differentiation of hESC-derived hepatocytes indicating that a 3D environment may be important for maturation of the cells. The magnitude of these differences was, however, difficult to interpret, as comparisons were not made to fetal and adult liver control. The present studies have extended these findings to show that culture in a static 3D format promotes differentiation as demonstrated by significant increases in expression of key liver genes such as ALB, CPS1, G6P and TDO and by a dramatic increase in the proportion of cells that express ASGPR1, a receptor found on mature hepatocytes. Maturation within the aggregates is also important for responsiveness to cAMP, as genes such as CYP1A2 and CYP3A4 were not induced in the 2D cultures. The mechanism by which aggregation promotes maturation is currently not known, but without being bound by theory, it could be related to enhanced cellular interactions and possibly the generation of polarized epithelial cells within the 3D structures, mimicking, to some extent the cell morphology of the hepatocytes within the liver.

The second step of the maturation strategy is optionally the activation of the cAMP pathway within the 3D aggregates through the addition of the cell permeable and more slowly hydrolyzed cAMP analogue 8-Br-cAMP. Specific genes within the liver, including PGC-1α, TAT and G6P, contain CREB elements in their promoter regions and as a consequence are direct targets of cAMP signaling[25,39,40]. Given this, these target genes were induced in 2D monolayers as well as in the 3D aggregates. The PCR and microarray analyses clearly demonstrate that the effect of cAMP signaling extends beyond the induction of target genes as activation of the pathway induced changes in gene expression patterns associated with different aspects of hepatocyte function including drug metabolism, mitochondrial biogenesis, lipid synthesis and glucose metabolism. These global changes support the interpretation that cAMP signaling promotes maturation of hepatoblasts. The fact that sustained cAMP signaling was not required to maintain the elevated levels of expression further supports the interpretation that the effect is one of maturation and not simply induction and maintenance of expression of specific genes. Some of the most notable changes in expression were observed with key drug-metabolizing enzymes including CYP1A2, CYP3A4 and UGT1A1 which were detected at levels as high as or higher than those found in primary human hepatocytes. The transcript levels were indicative of function, as the HES2-derived cells displayed levels of functional enzyme comparable to that in primary hepatocytes. Similar patterns of induction were observed in hepatocyte-like cells from two hESC lines and one hiPSC line indicating that this maturation strategy is broadly applicable.

Endocrine hormones such as insulin and glucagon can influence cAMP levels in the adult liver that have acute effects on glucose metabolism as well as chronic effects via regulating gene expression. Under conditions of fasting, cAMP levels are upregulated resulting in the rapid induction of PGC-1α and genes involved in gluconeogenesis, ensuring an energy supply[41, 42]. In addition to conditions of fasting, it has been reported that expression of PGC-1α is dramatically upregulated 1 day after birth in the mouse liver[43]. This upregulation is thought to rapidly promote maturation of the neonatal hepatocytes. Without being limited by theory, through the upregulation of PGC-1α expression, the effects of cAMP signaling on the hESC-derived hepatoblasts may be recapitulating to some extent, the change observed in the liver during fasting and/or in hepatocyte lineage at birth resulting the generation of cells that display many features of mature cells.

In summary, the inventors have, for the first time, defined steps that promote the maturation of hepatic lineage cells from hPSCs resulting in the generation of cells that display gene expression profiles similar to those of primary human hepatocytes. The development of metabolically functional cells is an important end point as it demonstrates that these advances will enable the routine production of hPSC-derived hepatocyte-like cells for drug metabolism analyses in the pharmaceutical industry. The cAMP-induced cells also provide an ideal candidate population for the development of bio-artificial liver devices and ultimately for transplantation for cell replacement therapy for the treatment of liver disease.

Materials and Methods:
HPSC Culture and Differentiation

HPSCs were maintained on irradiated mouse embryonic feeder cells in hESC media consisting of DEME/F12 (50:50; Gibco) supplemented with 20% Knock-out serum replacement (KSR) as described previously[44]. Prior to the generation of embryoid bodies (EBs), hESCs were passaged onto Matrigel™-coated plates for 1 day to deplete the population of feeder cells. At this stage, the hESCs were dissociated by 0.25% Trypsin-EDTA to generate small cluster as previously described[44,45] and then cultured in serum free differentiation (SFD) media in the presence of BMP4 (3 ng/ml) for 24 hours (day 0 to day 1). At day 1, the EBs were harvested and re-cultured in induction medium A that consisted of Stem-PRO-34® supplemented with glutamine (2 mM), ascorbic acid (50 pg/ml; Sigma), MTG ($4.5 \times 10^4$ M; Sigma), basic fibroblast growth factor (bFGF; 2.5 ng/ml), activin A (100 ng/ml), Wnt3a (25 ng/ml) and BMP4 (0.25 ng/ml) for 3 days. On day 4, the EBs were harvested and re-cultured in StemPRO-34® supplemented with bFGF (10 ng/ml), activin A (100 ng/ml), Wnt3a (25 ng/ml) and BMP4 (0.25 ng/ml) (medium B). EBs were harvested at day 6, dissociated to single cells and the cells cultured for 2 days on Matrigel™-coated 12 well plates at a concentration of $4 \times 10^5$ cells in media B without Wnt3A and with activin A at a concentration of 50 ng/ml. At day 8, medium B was replaced with hepatic specification media that consisted of Iscove's Modified Dulbecco's Medium (IMDM) supplement with 1% vol/vol B27 supplement (Invitrogen: A11576SA), ascorbic acid, MTG, FGF10 (50 ng/ml) (from day 8 to day 10), bFGF (20 ng/ml) (from day 10 to day 14), and BMP4 (50 ng/ml). Media was changed every 2 days from day 8 to day 14. To promote maturation of HES2-derived hepatic cells, they were cultured in maturation media A for 12 days. Maturation media A consisted of IMDM with 1% vol/vol B27 supplement, ascorbic acid, Glutamine, MTG, Hepatocyte growth factor (HGF) (20 ng/ml), Dexamethasone Dex) (40 ng/ml) and Oncostatin M (20 ng/ml). Aggregates were generated from the population at day 26 of culture. To generate aggregates the cells were dissociated with collagenase and TrypleE and then cultured in six well ultra-low cluster dishes at a concentration of $6 \times 10^5$ cells per well in maturation medium A supplemented with Rho-kinase inhibitor and 0.1% BSA. Aggregates were maintained under these conditions until day 32, with media changes every 3 days. At day 32, the media was changed to maturation medium B that consisted of Hepatocyte culture medium (HCM) (Lonza: CC-4182) without EGF. 0 mM 8-Br-cAMP (Biolab: B007) was added at this stage. Media was changed every 3 days. To generate hepatocyte like cells from H9, H1 and IPS cells, the following changes were made to the hepatic specification media. The concentration of bFGF was increased to 40 ng/ml and the base media was switched from IMDM to H16 DMEM for culture from days 8 to 14 and then to H16 DMEM plus 25% Ham's F12 from days 14 to 20. IMDM was replaced with H21 DMEM plus 25% Ham's F12 and 0.1% BSA for the maturation media A used from days 20 to 32. All cytokines were human and purchased from R&D Systems, unless stated otherwise. EB and monolayer cultures were maintained in a 5% $CO_2$, 5% $O_2$, 90% $N_2$ environment. Aggregation cultures were maintained in a 5% $CO_2$ ambient air environment.

Flow Cytometry

Flow cytometric analyses were performed as described previously[45]. For cell surface markers, staining was carried out in PBS with 10% FCS. For intracellular proteins, staining was performed on cells fixed with 4% paraformaldehyde (Electron Microscopy Science, Hatfield, PA, USA) in PBS. Cells were permeabilized with 90% ice-cold methanol for 20 minutes for Sox17 and FoxA2 staining as previously described[45]. Albumin and alpha-fetoprotein staining was performed in PBS with 10% FCS and 0.5% saponin (Sigma). Stained cells were analyzed using an LSRII flow cytometer (BD).

Immunostaining

Immunostaining was carried out as described previously[45]. Cells were fixed in the culture wells with 4% PFA at 37° C. for 15 minutes, washed three times in DPBS (with $CaCl_2$ and $MgCl_2$)+0.1% BSA, and then permeabilized in wash buffer with 0.2% Triton-X100 for 20 minutes. Following an additional 3 washes in DPBS (with $CaCl_2$ and $MgCl_2$)+0.1% BSA, the cells were blocked with protein block solution (DAKO; X0909) for 20 minutes at room temperature. For evaluation of albumin and alpha-fetoprotein positive cells, the cells were stained for 1 hour at room temperature with either a goat anti-ALB antibody (Bethyl) or a rabbit anti-AFP antibody (DAKO). Concentrations of isotype controls were matched to primary antibodies. To visualize the signal, the cells were subsequently incubated for 1 hour at room temperature with either a donkey anti-goat Alexa 488 antibody (Invitrogen) or a donkey anti-rabbit-Cy3 antibody (Jackson Immunoresearch). For Sox17 staining, the cells were fixed, permeabilized and blocked as described above. The cells were incubated with goat-anti-SOX17(R&D) over night at 4° C. The signal was visualized by incubation with donkey anti-goat Alexa 488 (Invitrogen). For ASGPR-1 staining, aggregates were cultured on Matrigel™-coated cover glass for 1 day. Following attachment and spreading, the cells were fixed with 4% PFA at 37 C for 15 minutes and then permeabilized with cold 100% methanol for 10 minutes. The cells were washed and blocked as above. The fixed cells were incubated with goat anti-ASGPR-1 (Santa Cruz) overnight at 4° C. and then with the rabbit anti ALB (DAKO) for 1 hour at room temperature. The signals were visualized by incubation with donkey anti-goat Alexa 488 antibodies and donkey anti-rabbit CY3 antibodies. Primary and secondary antibodies were diluted in DPBS+2% BSA+0.05% Triton-X100. ProLong® Gold Antifade with DAPI (Invitrogen) was used to counterstain the nuclei. The stained cells were visualized using a fluorescence microscope (Leica CTR6000) and images captured using the Leica Application Suite software.

Quantitative Real Time-PCR

Total RNA was prepared with RNAqueous® Micro Kit (Ambion) and treated with RNase-free DNase (Ambion). 500 ng to 1 µg RNA was reverse transcribed into cDNA using random hexamers and Oligo(dT) with Superscript® III Reverse Transcriptase (Invitrogen). qPCR was performed on a MasterCycler® ep realplex (Eppendorf) using A QuentiFast SYBR Green PCR Kit (Quiagen) as described previously[45]. Expression levels were normalized to the housekeeping gene TATA box binding protein (TBP). To measure UGT1A1 expression, relative gene expression was calculated using delta-delta CT method relative to the level in 8-Br-cAMP (−) treatment cells. Total human adult and fetal liver RNA was purchased from Clontech. Two primary hepatocyte RNA samples were provided by Dr Stephen C. Strom (University of Pittsburgh) and a third sample was purchased from Zenbio (Lot; 2199). Two primary hepatocyte samples were cultured for two day and were harvested. One (HH1892) is isolated from a 1-year-old Caucasian male and the other (HH1901) is isolated from a 14 months old male, explanted liver due to cholestasis. A third sample (Zenbio: lot 2199) is isolated from a 48 years old male Caucasian organ donor.

Indocyanine Green Uptake of Hepatic Aggregates

The indocyanine green (ICG, Sigma) solution was added to the cells at final concentration of 1 mg/ml ICG in HCM (Lonza). The cells were incubated at 37° C. for 1 hour, washed 3 times with PBS, and then examined with an inverted Microscope (Leica).

Drug Metabolism Assay by HPLC

Hepatic aggregates were incubated in HCM containing either the CYP1A2 substrate phenacetin (200 µM), the CYP2B6 substrate bupropion (900 µM), the NAT1/2 substrate sulfamethazine (SMZ) (500 µM), or the total UGT substrate 4-methylumbeliferone (4-MU) (200 µM) for either 24 or 48 hours. After incubation, aliquots of the medium were collected and levels of metabolites were quantified using individually optimized high-performance liquid chromatography assays. Hydroxybupropion level was assayed based on the HPLC method in Loboz et al[46]. 4-MU glucuronide was measured by high-performance liquid chromatography coupled with tandem mass spectrometry as described previously[47]. Cryopreserved hepatocytes were thawed and plated on collagen culture dishes at a density of $1 \times 10^4$ cells per well for either 24 or 48 hours. Supernatant was harvested following either 24 or 48 hours of culture and activities for CYP1A2, CYP2B6, NAT1/2 and total UGT measured.

Microarray Processing and Data Analysis

RNA samples were run on Affymetrix Human Gene ST v 1.0 chips following standard Affymetrix guidelines at the University Health Network Genomics Centre. Briefly, 300 ng of total RNA starting material for each sample was used as input to the Ambion WT Expression Kit. 2.7 µg of amplified cDNA was then fragmented, labeled and hybridized to Affymetrix Human Gene ST v 1.0 chips for 18 hours (45° C. at 60 RPM). Arrays were washed using a GeneChip Fluidics Station P450 fluidic station and scanned with an Affymetrix GeneChip Scanner 7G. After scanning, each chip was checked and found to pass Affymetrix quality control guidelines. Raw CEL files were imported into Genespring software (Agilent, v 11.5.1) and probe level data was summarized using the ExonRMA1 6 algorithm based on the HuGene-1_0-st0v1_na31_hg19_2010-09-03 build. Furthermore, each gene was normalized to the median value across all samples under consideration. All statistics were performed on log 2 transformed data. In total, 28869 transcripts are represented on this array.

As a first step, transcripts were filtered to remove those that were consistently in the lower $20^{th}$ percentile of measured expression across all of the 3 sample groups. An unsupervised hierarchical clustering analysis with a Pearson centered distance metric under average linkage rules was used to address overall similarity and differences between the samples and groups. Directed statistical analysis between the 3 sample groups was performed using an ANOVA with a Benjamini and Hochberg False Discovery Rate (FDR, q<0.05)[48]. To find sets of differentially expressed transcripts with biological meaning, a gene ontology (GO) analysis was performed using a corrected Benjamini and Yuketieli hypergeometric test at the q<0.1 significance level[49]. Two a priori defined sets of specific transcripts were examined in more detail: transcripts related to specific liver related activity of interest; and transcripts found to be expressed and liver specific based on publicly available information from the HOMER database[50].

Example 2

CHIR99021 is a selective inhibitor of GSK3 that has been reported to mimic the canonical Wnt signal pathway. CHIR99021 was tested as a replacement of wnt3a (e.g. added in combination with activin) in inducing Embryoid bodies and monolayer induction for definitive endoderm cells from hPSCs. As see in FIGS. 8A and 8B, the proportion of CKIT*CXCR4$^+$ and CXCR4$^+$EPCAM$^+$ cells induced using CHIR99021 to replace Wnt3a is greater than 95% of the population and is comparable to what is seen with Activin/wnt3a induction. FIGS. 8A and 8B demonstrate that CHIR99021 can induce definitive endoderm cells. FIG. 8A is a flow cytometric analysis showing the proportion of CXCR4+, CKIT$^+$ and EPCAM$^+$ cells in day six activin/CHIR 99021 of Embryoid body induction with activin/wnt3a. FIG. 8B is a flow cytometric analysis of showing the proportion of CXCR4$^+$, CKIT$^+$ and EPCAM$^+$ cells in day six activin/CHIR 99021. FIGS. 8C and 8D show day seven of monolayer induction with 8C, activin/wnt3a, or 8D, activin/CHIR 99021.

Methods

Induction of Definitive Endoderm with GSK3 Beta Inhibitor.

For EBs induction, CHIR99021 (0.3 µM) was replaced from Wnt3a for endoderm induction.

For monolayer induction, HPSCs were maintained on irradiated mouse embryonic feeder cells in hESC media consisting of DEME/F12 (50:50: Gibco) supplemented with 20% Knock-out serum replacement (KSR) as described previously (Kennedy et al., 2007). Prior to the induction of endoderm in monolayer culture, hESCs were passaged onto a Matrigel coated surface (typically 2 well plates) for 1 day. At day 0, the cells were cultured in a RPMI based medium supplemented with glutamine (2 mM), MTG ($4.5\times10^{-4}$ M: Sigma), activin A (100 ng/ml), CHIR99021 (0.3 µM) or Wnt3a (25 ng/ml). From day 1 to day 3, medium was changed every day with RPMI supplemented with glutamine (2 mM), ascorbic acid (50 pg/ml; Sigma), MTG ($4.5\times10^{-4}$ M; Sigma), basic fibroblast growth factor (bFGF; 5 ng/ml), activin A (100 ng/ml). From days 3-5 the cells were cultured in SFD based medium supplemented with glutamine (2 mM), ascorbic acid (50 pg/ml; Sigma), MTG ($4.5\times10^{-4}$ M; Sigma), basic fibroblast growth factor (bFGF; 5 ng/ml), activin A (100 ng/ml). The media was changed every the other day. At day 7, the definitive endoderm was specified to a hepatic fate by treatment with FGF and BMP pathway agonists, as described above.

Example 3

Ectopic Liver Tissue in NSG Mice

Transplanted hESC-derived hepatoblasts engraft and generate cells that express hepatocyte differentiation markers.

Figure 8F:
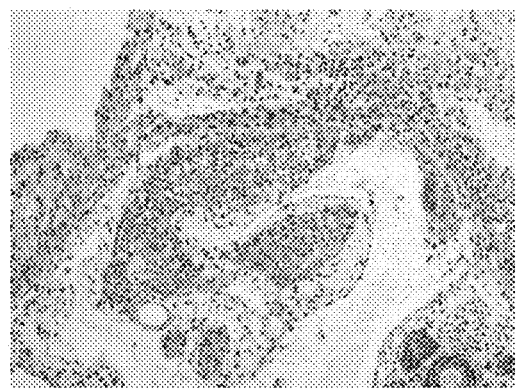

FIGS. 8E-8F demonstrate engraftment of ES derived liver cells prepared using the method described in Example 1 except that the GSK3 inhibitor CHIR99021 was used to make the transplanted cells as described in Example 2.

FIGS. 8E-8H: Ectopic liver tissue in NSG Mice. FIG. 8E is a demonstrative photomicrograph of H&E staining of the intestinal mesentery area, showing a cluster of hESC-derived hepatocyte (arrowhead) 2 months after transplant. Magnification was 5×. Intestine (arrow), engrafted cells (arrowhead). FIG. 8F shows high magnification (10×) photomicrographs of H&E stained section from FIG. 8E.

Figure 8G:
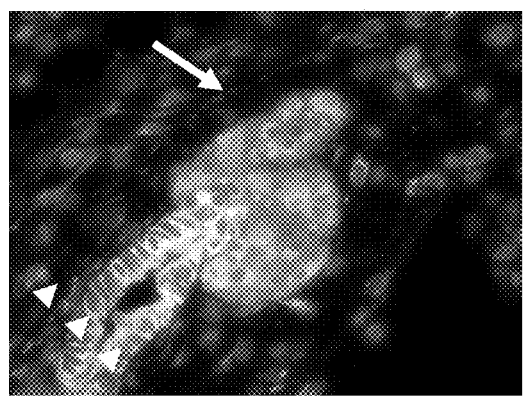
Figure 8H:
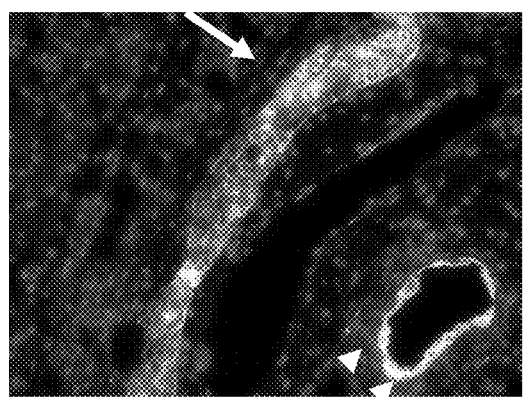

FIGS. 8G and 8H: Immunohistochemical staining shows the presence of hESC-derived cells in the intestinal mesentery area two months after transplant. Double staining for human Albumin (Alexa 488: green) (showing as an arrow) and CK19 (Cy3: red) (showing as an arrowhead) shows that the transplanted cells have the potential to differentiate into the hepatocyte and cholangiocyte lineages. HESC-derived hepatocyte-like cells were observed as albumin positive cells (Arrow), whereas cholangiocyte-like cells expressed CK19 and were found in duct like structures (Arrowhead).

Methods

Ectopic Liver Tissue in NSG Mice

Six week-old NSG mice were obtained from The Jackson Laboratories (Bar Harbor, ME, USA) and housed at UHN animal facility. Aggregates (day 27) consisting of hESC-derived hepatocyte progenitors (hepatoblasts) and hESC-derived CD34+ endothelial cells were suspended 50 µl Matrigel (BD bioscience) and kept on the ice until transplantation. Recipient mice were anesthetized with 1-3% isoflurane and laparotomized. The intestinal mesentery areas were exposed and the cells mixture with Matrigel was positioned on the mesentery area and covered with a absorbable hemostat agent, Surgicel (Ethicon 360, USA). Two months following transplantation, the, mice were sacrificed and evaluated for presence of hESC-derived cells by histological analyses.

Example 4

A small molecule related to Wnt/p-catenin pathway can expand hepatic progenitor cells. Day 27 hepatic progenitor cells (H9) were dissociated and plated on 96 well Matrigel coated dish at the density of $1\times10^4$ cell per well. Cells were treated with different concentrations of CHIR99021 (0.3 µM, 1 µM and 3 µM) and cultured for 9 days. Increases in the ratio of hepatic progenitor cells was examined by the counting the cell number compared to day 27 cell number without treatment (FIG. 9A).

Inhibition of Wnt and MEK/ErK pathway can increase the expression of gene associated to Phase I drug metabolism enzyme.

Gene expression of CYP3A4 in day 44 3D hepatic aggregation cultured with small molecule related to the inhibition of Wnt/p-catenin signal (XAV 939: 1 µM) and MEK/Erk signal (PD0325901: 1 µM). Together with 8-Br-cAMP, Inhibition of Wnt and MEK/ErK signal has an impact to increase gene expression of CYP3A4 (FIG. 9D).

Gene expression of CYP1A2 in day 44 3D hepatic aggregation cultured with small molecule related to the inhibition of Wnt/p-catenin signal (XAV 939: 1 µM) and MEK/Erk signal (PD032590: 1 µM). Together with 8-Br-cAMP, Inhibition of Wnt and MEK/ErK signal has an impact to increase gene expression of CYP1A2 (FIG. 9D).

Gene expression of ALB at day 26 hepatocyte-like cells culture on several different extra cellular matrix (ECM). The endoderm cells from Embryoid bodies (EBs) were dissociated and plated on the ECM at the cell at cell density of $4\times10^5$ cells and cultured in hepatic specification and maturation medium as described above by day 26. Total RNA was extracted at from day 26 cells and measured the level of Albumin expression. The expression level was determined by the fold difference compared to gelatin coated cultured condition (FIG. 9F).

Methods

Induction of Definitive Endoderm with GSK3 Beta Inhibitor.

For EBs induction, CHIR99021 (0.3 µM) replaced Wnt3a during endoderm induction.

For monolayer induction, HPSCs were maintained on irradiated mouse embryonic feeder cells in hESC media consisting of DEME/F12 (50:50: Gibco) supplemented with 20% Knock-out serum replacement (KSR) as described previously (Kennedy et al., 2007). In prior to the induction of endoderm in monolayer culture, hESCs were passaged onto 12 wells Matrigel coated plate for 1 day. At day 0, the cells were cultured in RPMI based medium that supplemented with glutamine (2 mM), MTG ($4.5\times10^{-4}$ M: Sigma), activin A (100 ng/ml), CHIR99021 (0.3 µM) or Wnt3a (25 ng/ml). From day 1 to day 3, Medium was changed every day consisted of RPMI supplemented with glutamine (2 mM), ascorbic acid (50 µg/ml; Sigma), MTG ($4.5\times10^{-4}$ M; Sigma), basic fibroblast growth factor (bFGF; 5 ng/ml), activin A (100 ng/ml). On day 3, 5, the cells were cultured SFD based medium supplemented with glutamine (2 mM), ascorbic acid (50 µg/m; Sigma), MTG ($4.5\times10^{-4}$ M; Sigma), basic fibroblast growth factor (bFGF; 5 ng/ml), activin A (100 ng/ml). Medium was changed every other day. At day 7, the definitive endoderm cells was started to differentiate with the hepatic specification medium as described above.

Example 5

Inducing Maturation of Cell Aggregates with cAMP Treatment

Cell aggregates were generated as in Example 1.

The cell aggregates were cultured in HGF, Dex and OSM until day 32 at which point cAMP was added. OSM was removed when cAMP analog and/or cAMP agonist is added. In some experiments, HGF was also removed from the cultures when cAMP analog and/or cAMP agonist is added. In other experiments, the addition of 10 ng/ml HGF (reduced from 20 ng/ml) when cAMP was added was shown to promote survival of the aggregates.

Without being bound by theory, it is believed that maintaining OSM has an inhibitory effect on the induction of expression of Phase 1 CYP enzymes, in particular CYP 3A4.

Example 6

Figure 10A:
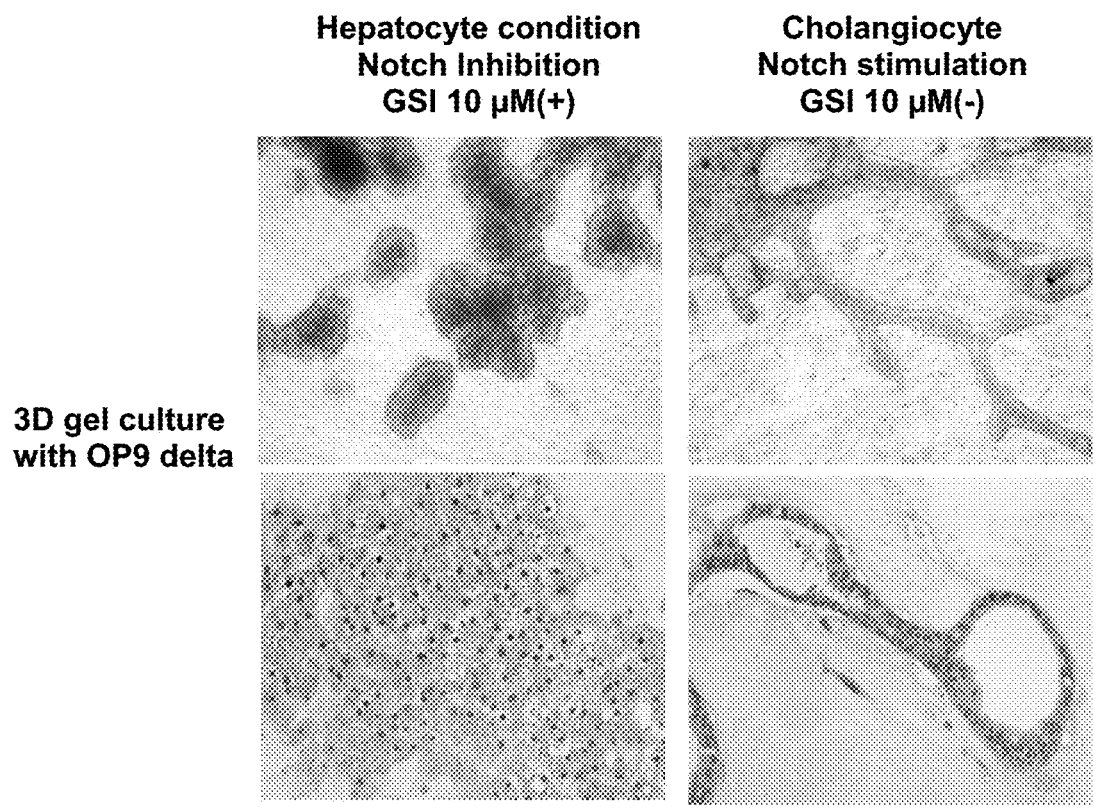
FIGS. 10A-10C show that the notch signaling pathway in hepatic progenitor cells influences the differentiation of the cholangiocyte lineage.

The Notch Signaling Pathway in Hepatic Progenitor Cells Influences the Differentiation of Cholangiocyte Lineage To investigate the differentiation of cholangiocyte-like cells, H9-derived day 27 hepatic progenitors were co-cultured with OP 9 cells (Notch signaling donor) in the presence of HGF 20 ng/ml and EGF 50 ng/ml. The H9-derived day 27 hepatic progenitors were derived as in Example 1. When the hepatic progenitor cells received Notch signaling activation from OP-9 cells, the albumin positive cells were completely diminished and turned into CK19 positive cells with an organized branching appearance (FIG. 10a, b). In contrast, when Notch signaling was inhibited in the co-cultured cells with gamma-secretase inhibitor (GSI) L-685, 458 (10 µM; Tocris), albumin and CK19 positive cells were found (FIG. 10A).

Further, an H&E section of the co-cultured cells either in the presence or absence of GSI showed that in the presence of GSI, chimeric aggregation was maintained. In the absence of GSI treatment, cells were arranged in an epithelial duct like structure containing lumen (FIG. 10A).

Figure 10B:
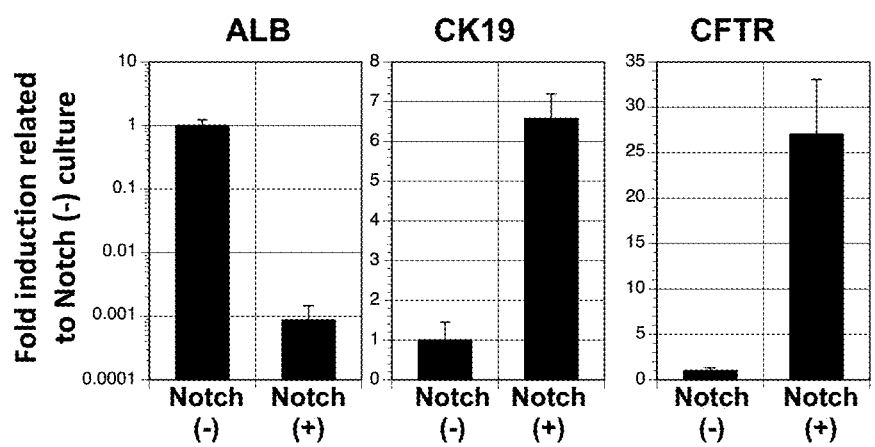

As shown in FIG. 10b, increased expression of CK19 and cystic fibrosis transmembrane conductance regulator (CFTR) in the OP9 coculture at day 36 and in the absence of GSI. Values shown are relative to cells cultured in the presence of GSI. The expression of albumin is seen when Notch signaling is inactivated by culturing in the presence of GSI, demonstrating the cells retain characteristics of hepatoblasts.

Figure 10C:
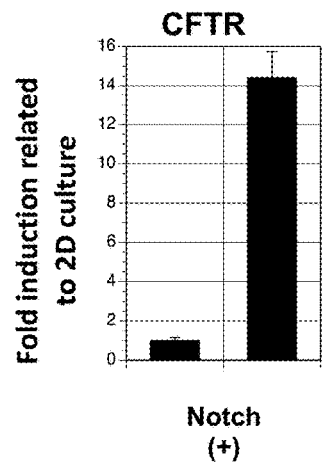

Lastly, a 3D co-culture of hepatic progenitors cells with OP 9 cells resulted in increased expression of CFTR at day 36 compared to a 2D culture (FIG. 10C).

The experiments described above demonstrate that cholangiocyte-like cells forming a bile-like structure can be induced from H9-derived hepatic progenitor cells through the activation of Notch signaling (for example by co-culturing with OP9, OP9delta and/or OP9Jagged1 cells). The expression of CFTR, a marker of functional cholangiocytes, was higher in 3D gel co-culture than in the 2D culture, showing that environment can also influence cholangiocyte maturation.

Example 7

Exemplary Maturation Media Formulations
For HES2 Cell Line from Day 14(EB)/Day 13 Monolayer- to Day 26(EB)/Day 25 (Monolayer)
Based Medium:
IMDM, 1% vol/vol B27 supplement, glutamine (2 mM), ascorbic acid (50 µg/m; Sigma), MTG ($4.5 \times 10^{-4}$ M; Sigma)
Cytokine and Growth Factors:
Hepatocyte growth factor (HGF) (20 ng/ml), Dexamethasone (Dex) (40 ng/ml) and Oncostatin M (20 ng/ml).
For H9 and iPS Cell Line from Day 14(EB)/Day 13 Monolayer- to Day 20 (EB)/Day 19 (Monolayer)
Based Medium:
H16/Ham's F12 (75%/25%), 1% vol/vol B27 supplement, glutamine (2 mM), ascorbic acid (50 pg/ml; Sigma), MTG ($4.5 \times 10^{-4}$ M; Sigma)
Cytokine and Growth Factors:
Hepatocyte growth factor (HGF) (20 ng/ml), Dexamethasone (Dex) (40 ng/ml) and Oncostatin M (20 ng/ml).
From Day 20(EB)/Day 19 monolayer- to Day 26(EB)/Day 25 (Monolayer)
Based Medium:
H21/Ham's F 12 (75%/25%), 1% vol/vol B27 supplement, glutamine (2 mM), ascorbic acid (50 µg/m; Sigma), MTG ($4.5 \times 10^{-4}$ M; Sigma)
Cytokine and Growth Factors:
Hepatocyte growth factor (HGF) (20 ng/ml), Dexamethasone (Dex) (40 ng/ml) and Oncostatin M (20 ng/ml).
Aggregation Stage
From day 26/day 25 to day 32/day 31
Based Medium:
IMDM or H21/Ham's F 12 (75%/25%), 1% vol/vol B27 supplement, glutamine (2 mM), ascorbic acid (50 pg/ml; Sigma), MTG ($4.5 \times 10^{-4}$ M; Sigma), Rho-kinase inhibitor (10 µM) and 0.1% BSA.
Cytokine and Growth Factors:
Hepatocyte growth factor (HGF) (20 ng/ml), Dexamethasone (Dex) (40 ng/ml) and Oncostatin M (20 ng/ml).
Aggregation stage with cAMP
From day 32/day 31 to day 44/day 43
Based Medium:
Hepatocyte culture medium (HCM) (Lonza: CC-41 82) without EGF. 10 mM 8-Br-cAMP (Biolab: B007), small molecule related to the inhibition of Wnt/beta.catenin signal (XAV 939: 1 □□) and MEK/Erk signal (PD032590: 1 µM).
Cholangiocyte Maturation Medium
Based Medium:
H21/Ham's F 12 (75%/25%), 1% vol/vol B27 supplement, glutamine (2 mM), ascorbic acid (50 pg/ml; Sigma), MTG ($4.5 \times 10^{-4}$ M; Sigma),
Cytokine and Growth Factors:
Hepatocyte growth factor (HGF) (20 ng/ml), Epidermal Growth factor (EGF) (50 ng/ml)

Example 8

The Effect of Endothelial Cells on hESC-Derived Hepatic Development.

Given that endothelial cells play an important role in liver development, this lineage was assessed for its influence on the growth and/or maturation of the hESC-derived hepatic cells. For these studies, CD34+ endothelial cells were generated from hESCs. For these studies, the HES2 hESC line was used which is engineered to express the red fluorescence protein (RFP) cDNA from the ROSA locus to enable us to track the endothelial cells. Endothelial cells were generated by induction with a combination of BMP4, bFGF and VEGF for 6 days at which time the CD34+ cells (also CD31+ and KDR+) were isolated by FACS. The sorted CD34+ cells were cultured for 6 days in EGM2 endothelial cell growth media and then used for the generation of chimeric aggregates using Aggrewells™. The endothelial cells were added to the Aggrewells 2 days prior to the hepatic cells to allow them to coat the bottom of the well (FIG. 12a). At this point, a single cell suspension of day 25 hepatoblasts was added on top of the endothelial cells and the mixture cultured in the Aggrewells for 48 hours. The aggregates were subsequently removed from the Aggrewells and cultured for an additional 6 days, at which time they were harvested and analyzed. As shown in FIG. 12B, the aggregates cultured together with the endothelial cells contained RFP+ cells and were larger than those cultured alone. Flow cytometric analysis revealed that the RFP+ cells represented greater than 30% of the population (FIG. 12c), indicating that significant numbers had integrated with hepatic cells in the aggregates. qRT-PCR analyses showed that the chimeric aggregates cultured for an additional 12 days expressed substantially higher levels of CYP3A4 message than the hepatic aggregates without the endothelial cells (FIG. 12d). Importantly, these levels were achieved without the addition of cAMP, suggesting that endothelial cells can promote maturation of the hPSC-derived hepatic cells. These findings indicate that the interaction with embryonic endothelial cells influences the survival and maturation of the hESC-derived hepatocytes.

Maturation of hESC-Derived Hepatocyte in Collagen Gels.

The combination of 3D aggregation, cAMP and PD/XAV did promote significant differentiation of the human pluripotent stem cell-derived hepatocytes (FIG. 9), (FIGS. 9D and 9E). The cells did retain some expression of AFP and fetal CYP3A7 indicating they may not be fully mature. To promote further maturation of the population, the chimeric endothelial/hepatic aggregates were treated with the combination of cAMP, PD and XAV. These aggregates were maintained either in liquid culture or in collagen gels to provide a source of extracellular matrix proteins. As shown in FIG. 13, the addition of endothelial cells to the aggregates (end) did not significantly impact the expression levels of ALB, CYP3A4, AFP or CYP3A7 when the aggregates were maintained in liquid culture. In contrast, culture of the aggregates in the collagen gel had a dramatic effect on AFP and CYP3A7 expression, as both were reduced to almost undetectable levels, similar to those found in the adult liver. The findings suggest that signaling pathways, cellular interactions and the extracellular environment all play a role in the maturation of hPSC-derived hepatocytes. This demonstrates that it is possible to generate cells that express little, if any AFP. This expression pattern suggests that these cells have progressed to a stage comparable to the hepatocytes in the adult liver.

Example 9

The development of protocols for the efficient generation of tissue specific cell types from human embryonic and induced pluripotent stem cells (pluripotent stem cells; PSCs) has helped towards the establishing of in vitro models of human development and disease and for designing new platforms for drug discovery and predictive toxicology. Lineages that comprise the liver are of particular importance as hepatocytes as well as cholangiocytes that make up the biliary system of the organ are primary targets of the adverse effects of drugs and of a range of inherited and infectious diseases. Given the central role of hepatocytes in drug metabolism, most efforts to date have been directed at the generation of this cell type from hPSCs. It has been possible to develop staged differentiation protocols that promote the generation of cells albeit in low efficiencies and lacking metabolic function, that display some characteristics of mature hepatocytes, including the expression of functional P450 enzymes. Recent studies have extended this strategy to patient specific induced pluripotent stem cells (iPSCs) and to model inherited liver diseases that affect hepatocyte function.

Disorders involving the biliary tract are common causes of chronic liver disease that result in significant morbidity and often require whole organ transplantation for definitive management. The underlying mechanisms of monogenic biliary diseases such as cystic fibrosis liver and Alagille syndrome remain incompletely understood, and more complex biliary diseases such as primary sclerosing cholangitis and biliary atresia lack appropriate models for understanding their pathophysiology or for screening novel pharmacological agents. The ability to generate functional cholangiocytes from hPSCs would fulfill these unmet needs.

The successful derivation of cholangiocytes from hPSCs will be dependent on the ability to accurately model the embryonic development of this lineage in the differentiation cultures. Cholangiocytes develop early in fetal life and derive from a bipotential progenitor known as the hepatoblast that also gives rise to the hepatocyte lineage. Targeting studies in the mouse have shown that specification of the cholangiocyte lineage from the hepatoblast is a Notch dependent event that is mediated by the interaction of Notch 2 expressed by the progenitors and Jagged-1 present on the developing portal mesenchyme. The discovery that the pediatric biliary tract disease Alagille syndrome is caused by mutations in either Notch 2 or Jagged 1 provides strong evidence that this pathway is also involved in cholangiocyte development in humans. As the cholangiocytes mature they organize to form a polarized epithelium that lines the developing primitive ductal structures, which gives rise to the biliary tract.

As a foundation for investigation of iPSCs from patients with biliary diseases, a robust protocol for the directed differentiation and maturation of functional cholangiocytes from hPSCs is described. hPSC-derived cholangiocytes could be induced to form epithelialized cystic structures that express markers found in mature bile ducts including the cystic fibrosis transmembrane conductance regulator (CFTR). CFTR function in these structures was demonstrated through the regulation of cyst swelling following stimulation of the cAMP pathway with forskolin. Cysts generated from cystic fibrosis patient iPSCs showed a deficiency in the forskolin-induced swelling assay that could be rescued by the addition of CFTR correctors. Collectively, these findings demonstrate that it is possible to generate cholangiocytes and biliary ductal-like structure from hPSCs and to use these derivative cell types to model aspects of cystic fibrosis biliary disease in vitro.

Results

Characterization of the hepatoblast stage of development in hPSC differentiation cultures.

Figure 14B:
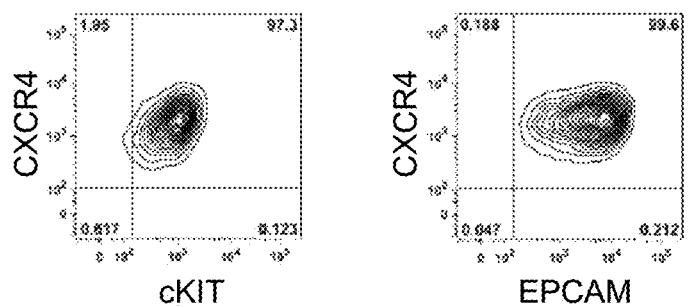

To generate cholangiocytes from hPSCs, it was necessary to first characterize the hepatoblast stage of development in the differentiation cultures. For these studies, we used a modified version of the protocol (FIG. 14A) that we developed for the generation of functional hepatocytes from hPSCs[1]. The major difference from our previous approach was that the endoderm induction step was carried out in monolayers rather than in 3D embryoid bodies (EBs). This change resulted in an acceleration of endoderm development in the cultures as populations consisting of greater than 90% CXCR4+ CKIT+ and EPCAM+ cells were generated by day three of differentiation (FIG. 14b). Comparable populations were not detected until day five of EB differentiation[1]. To specify the endoderm to a hepatic fate, the cultures were treated with a combination of bFGF and BMP4 at day 7 of differentiation.

Figure 14C:
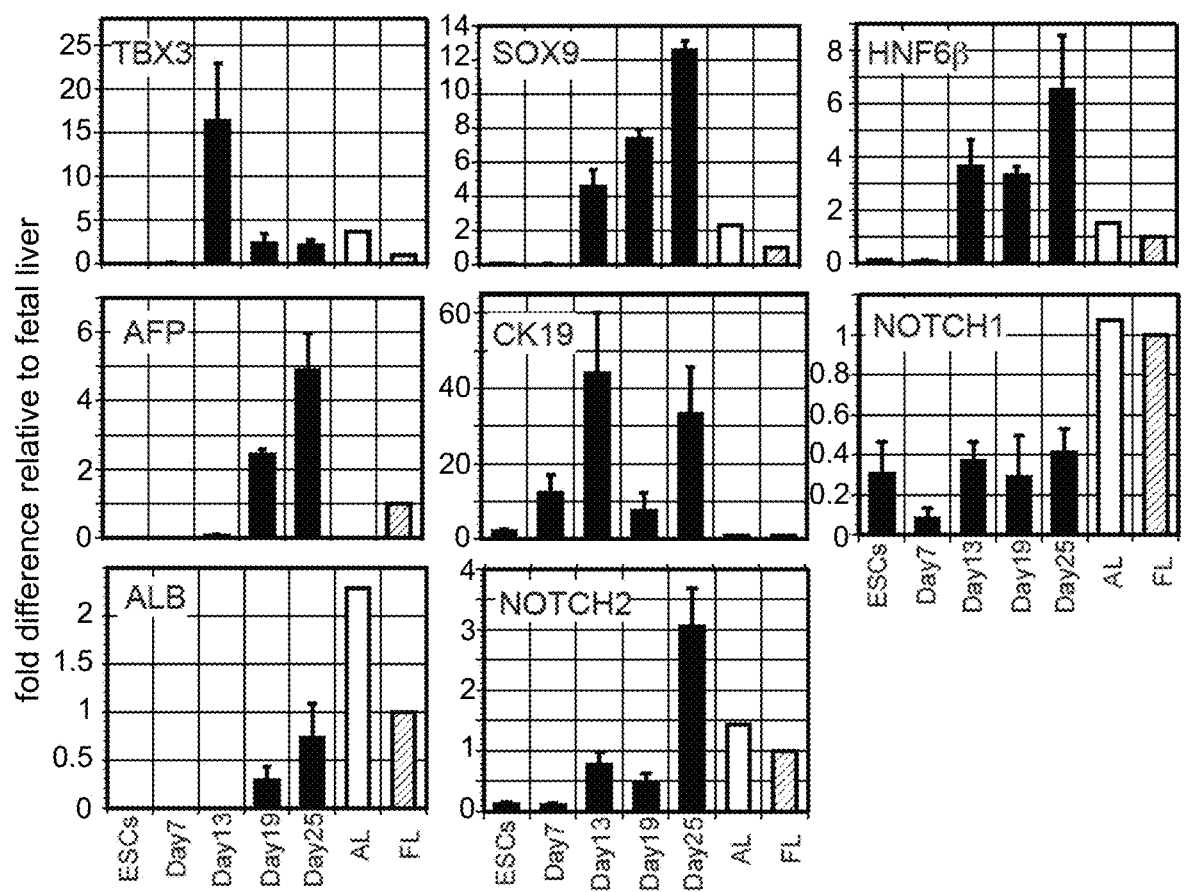

At the onset of hepatic development in the embryo newly formed hepatoblasts delaminate from the from the ventral foregut epithelium and invade the septum transversum to form the liver bud. The formation of the bud is dependent on the transcription factor Tbx3 that is expressed transiently during the early stages of this process[23]. As the bud expands, the progenitor cells downregulate Tbx3 and maintain and/or upregulate the expression of a combination of genes that are normally expressed in the hepatic and/or cholangiocyte lineages including albumin (ALB), alpha fetoprotein (AFP) cytokeratin 19 (CK19), Sox9, NHF6p and NOTCH2. RT-qPCR analyses of the bFGF/BMP4 treated hESC-derived endoderm population revealed a transient upregulation of TBX3 expression at day 13 of differentiation, identifying this time as the stage of hepatoblast specification (FIG. 14c). Immunostaining revealed that the majority of the cells in the day 13 population were TBX3+, indicating that hepatoblast specification was efficient. The onset of SOX9 and HNF6B expression overlapped with that of TBX3 (FIG. 14c). However, unlike TBX3, the expression of these genes continued to increase until day 25, the final day of the analyses. Expression of ALB and AFP was upregulated at day 19 and also increased at day 25. CK19 showed a biphasic pattern, with peak levels of expression detected at days 13 and 25. Immunofluorescent staining and flow cytometric analyses revealed that the majority of the cells at day 25 of differentiation were ALB+, AFP+ and CK19+. Together these findings strongly suggest that the cells within the day 25 population are representative of the expanded hepatoblast stage of development, the equivalent of the liver bud in vivo. Notch 2 but not Notch 1 expression was also upregulated at day 25, further supporting the interpretation that this population contains hepatoblasts capable of signaling through this pathway.

Notch Signaling Promotes Cholangiocyte Development from the hPSC-Derived Hepatoblast-Like Population.

To investigate the effect of Notch signaling on cholangiocyte development, we co-cultured the hepatoblast population (day 25) with OP9 stromal cells that are known to express different Notch ligands including Jagged-1[4,5]. The hPSC-derived cells did not survive well when cultured on the stroma as a single cell suspension. To overcome this problem, we generated 3D aggregates from the day 25 monolayer cells and cultured them on the OP9 stromal cells. Immunostaining and flow cytometric analyses revealed that the majority of the cells within the aggregates prior to co-culture were ALB+AFP+CD19+NOTCH2+ indicating that they maintained hepatoblast characteristics This aggregation step appears to select for hepatoblasts, as aggregates generated from day 25 populations consisting of only 80% ALB+AFP+CK19+ cells contained greater than 90% ALB+ AFP+CK19+ cells following 48 hours of culture. When co-cultured on the OP9 stroma (9 days) the aggregates formed distinct clusters of CK19+ cells that no longer expressed ALB, suggesting that they had undergone the initial stage of cholangiocyte specification As studies in the mouse have shown that HGF, EGF and TGFβ1 signaling play a role in bile duct development[6-8], we next added these factors, either individually or in combination to the cultures to determine if activation of these pathways would promote further development of the CK19+ clusters[6-8]. The addition of EGF or TGFβ1 or the combination of both led to an increase in the size of CK19+ aggregates In contrast, HGF alone had little effect. Interestingly the combination of either EGF and HGF or EGF, HGF and TGFβ1 induced a dramatic morphological change and promoted the formation of branched structures consisting of CK19+ cells. RT-qPCR FIG. 15A and flow cytometric analyses (FIG. 21) confirmed the immunostaining findings and demonstrated a complete absence of ALB+ cells following co-culture with OP9.

Figure 15A:
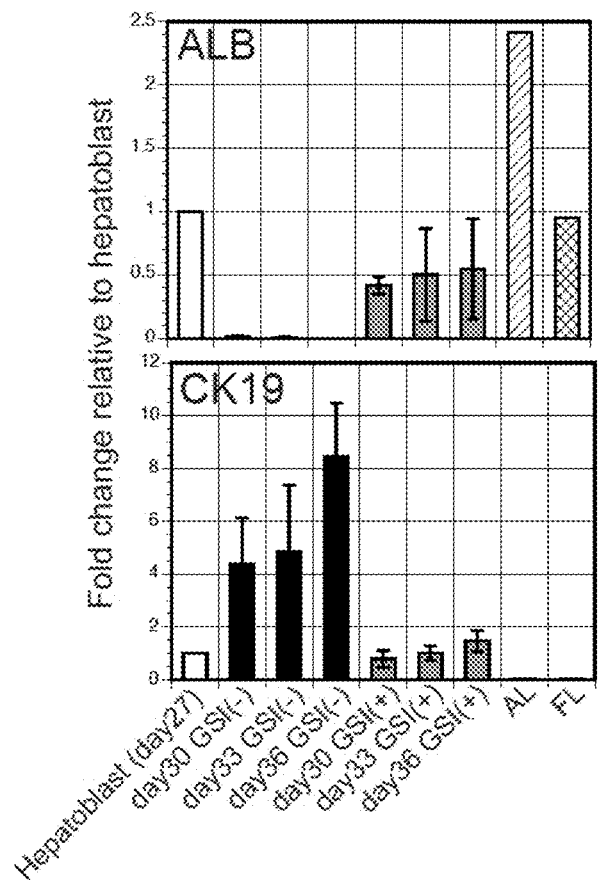
FIG. 15A demonstrates that Notch signaling promotes cholangiocyte development from the hPSC-derived hepatoblast-like population. RT-qPCR-based expression analysis of ALB and CK19 in the hepatoblast-derived cells following co-culture with OP9 in media supplemented with HGF (20 ng/ml), EGF (50 ng/ml), and TGFβ1 (5 ng/ml) in the presence or absence of the gamma-secretase inhibitor (GSI), an antagonist of the Notch pathway. Cells were harvested and analyzed at days 30, 33, and 36 of culture. Values were determined relative to TBP and presented as fold change relative to levels of expression in the day 27 hepatoblast aggregates which is set as 1.
Figure 15B:
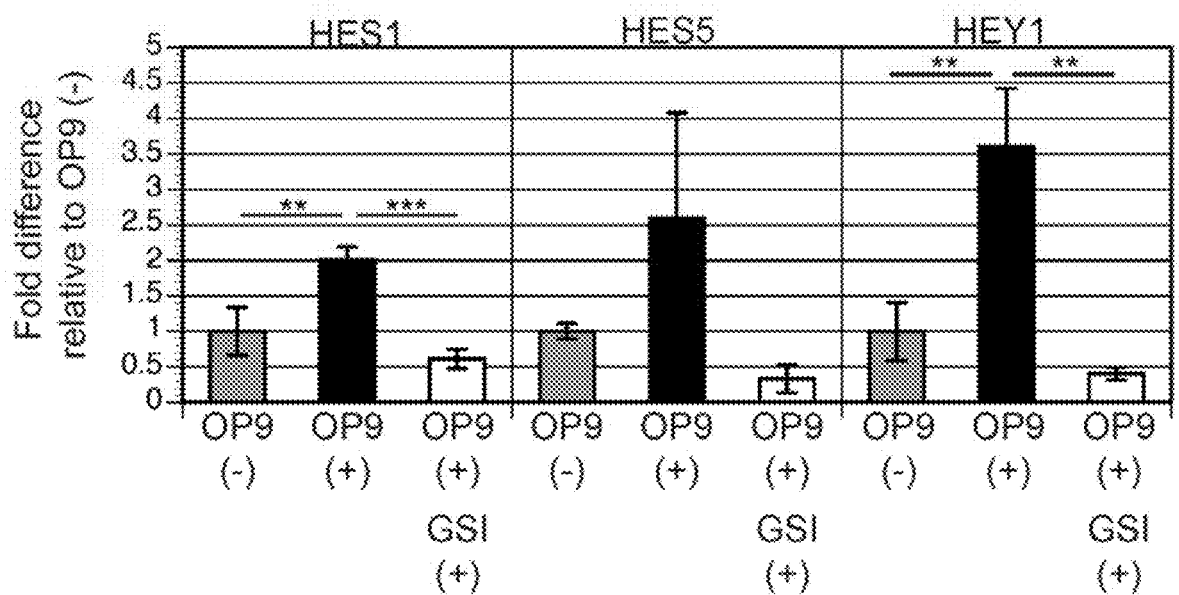
FIG. 15B is an RT-qPCR based expression analysis of the Notch target genes HES1, HES5 and HEY1 in hepatoblast-derived cells following culture with or without OP9. Cells were assayed at day 36 of culture. For this analyses, the day 27 hepatoblast aggregates were plated either on OP9 (OP9+) stromal cells or Matrigel (OP9−) in media containing HGF, EGF, and TGFβ1 (5 ng/ml) in the presence of absence of the Notch signaling antagonist gamma-secretase inhibitor (GSI) Values were determined relative to TBP and presented as fold change relative to the levels of expression in the cells at day 36 cultured on Matrigel. This value was set as 1. Bars in all graphs represent the standard deviation (SD) of the mean of three independent experiments. *P<0.05, P<0.01, *P<0.001 (Student's t-test; n=3).

The addition of gamma secretase inhibitor (GSI), an antagonist of the Notch pathway, blocked the downregulation of ALB expression, reduced the proportion of CK19+ cells in the cultures and inhibited the development of the branched structures indicating that these effects were mediated by Notch signaling (FIG. 15a). Expression of the Notch targets HES1, HES5 and HEY1 was upregulated following nine days of culture on OP9. (FIG. 15b) This increase in expression was block by the addition of the γ-secretase inhibitor demonstrating that co-culture with OP9 effectively activated the Notch pathway (FIG. 15b). Analyses of the differentiation potential of two other hPSC lines (ESC HES2 and iPSC Y2-1) revealed similar temporal patterns of TBX3 and hepatoblast marker expression, indicating that the transition through these stages is a characteristic of hepatic development in vitro. (FIG. 22) Aggregates derived from both lines generated branched structures consisting of CK19+ALB cells following co-culture with the OP9 stromal cells. As observed with the H9-derived populations, the downregulation of ALB expression and the development of these structures were NOTCH dependent events. Collectively, these findings indicated that activation of Notch signaling in the hepatoblast population induces the initial stages of cholangiocyte development and the combination of HGF, EGF and TGFβ1 signaling promotes morphological changes leading to the formation of branched structures, possibly reflective of the early stages of duct morphogenesis.

Three-Dimensional Culture Promotes Cholangiocyte Maturation

Figure 16A:
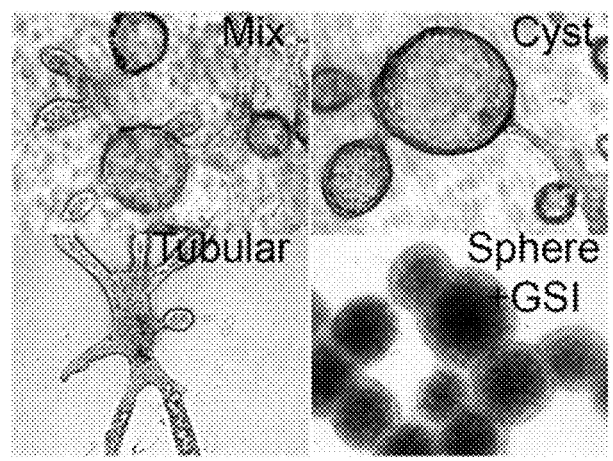
FIG. 16A demonstrates that three-dimensional culture promotes cholangiocyte maturation: Morphology of chimeric aggregates consisting of day 25 hESC-derived cells and OP9 stromal cells (GFP+). H9-derived day 25 hepatoblast were mixed (aggregated) with OP9 stromal cells at a ratio of 4:1, in low cluster culture dishes for 48 hours. The chimeric aggregates were embedded in a mixture of type 1 collagen (1.2 mg/ml) and Matrigel (40%) to establish a 3D gel culture. The cultures were maintained over 2 weeks in the media containing of HGF, EGF and TGFβ1 in the presence or absence of GSI.
Figure 16B:
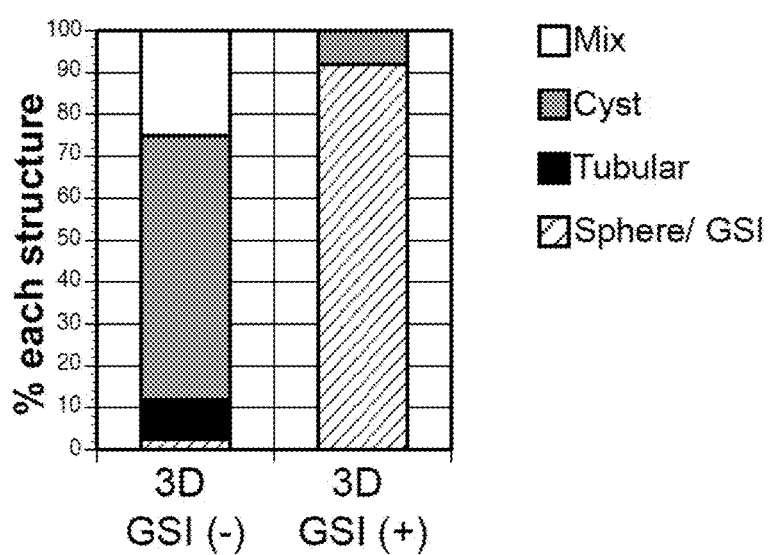
FIG. 16B shows a proportion of structures displaying a tubular, cyst or sphere morphology that develop in the 3D cultures. Values are presented as proportion of total structure that develop in the presence or absence of GSI. The values are representative of 3 independent experiments.
Figure 16C:
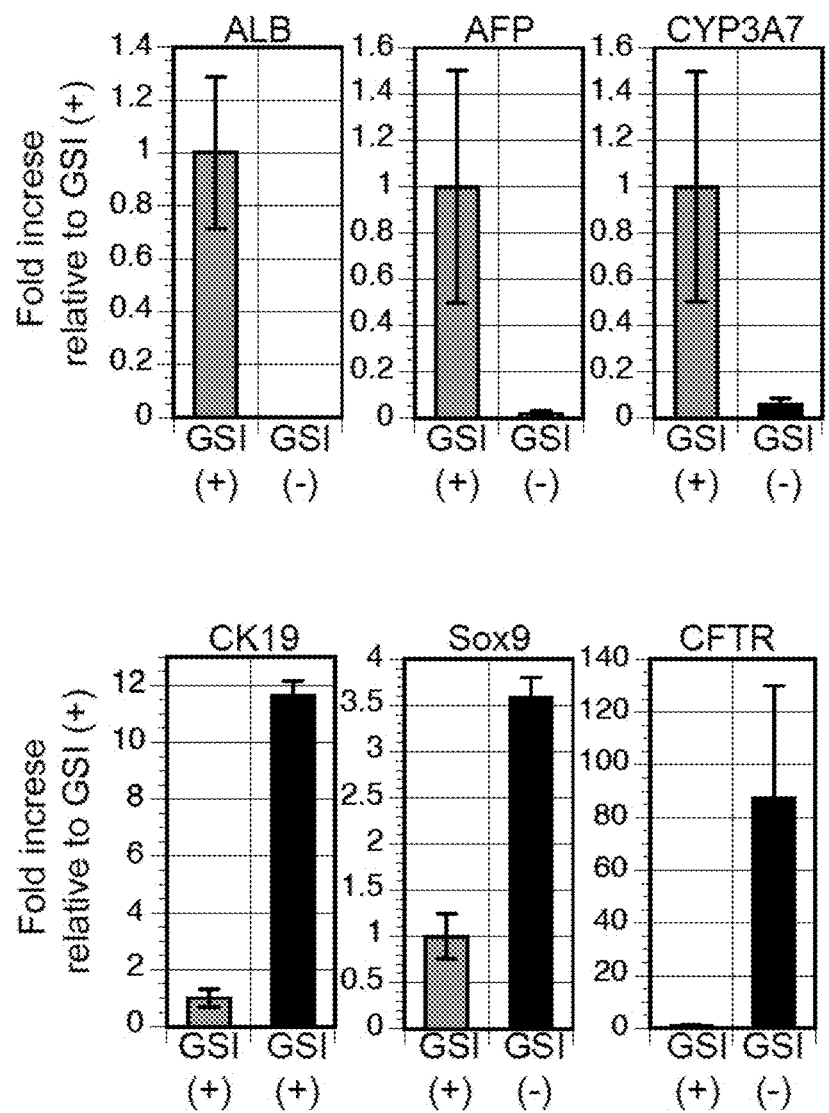
FIG. 16C is an RT-qPCR based expression analyses of pooled structures that developed in the 3D gels. The cultures were harvested at day 44 and the cells analyzed for expression of genes indicative of the hepatocyte (ALB, AFP and CYP3A7) and cholangiocyte (CK19, Sox9 and CFTR) lineages. Values are determined relative to TBP and presented as fold change relative to levels of expression in the population treated with GSI, which is set at one.

To determine if the branching observed in the OP9 co-cultures is indicative of the initial stages of bile duct development, we next established a culture system to promote the growth of 3D cellular structures. With this approach, chimeric aggregates consisting of day 25 hESC-derived cells and OP9 stromal cells (GFP+) were cultured in a media mixture consisting of 1.2 mg/ml collagen, 40% Matrigel and HGF, EGF and TGFβ1 (FIG. 23a). Within 2 weeks of culture in these conditions, the aggregates underwent dramatic morphological changes and formed either tubular structures, hollow cysts or a mixture of both (FIG. 16a,b). The cysts were the most abundant structures in these cultures (FIG. 16b). Expression of the Notch target genes Hes1, Hes5 and Hey1 was upregulated in the populations that developed from the chimeric aggregates compared to the ones derived from aggregates without the OP9 cells, indicating that Notch signaling was active in the cultures (FIG. 23B). Histological analyses revealed that the tubular and cystic structures had a ductal morphology with a lumen and were comprised of epithelial-like cells that express CK19+ and E-CADHERIN+ but not ALB+, ZO-1 (Zonula occuludens 1), the tight junction marker was also expressed and was found to be restricted to the apical side of the structures, suggesting that the cells had acquired apicobasal polarity, a feature of mature epithelial ducts. The cells in the ducts also expressed the Cystic fibrosis transmembrane conductance regulator (CFTR), a transmembrane channel that is first expressed in the adult biliary tract. As with ZO-1, the CFTR protein was detected predominantly on the apical side of the duct-like structure. Western blot analyses confirmed the presence of the protein in the population generated from the chimeric aggregates (FIG. 23D). The levels of CFTR message and protein were considerably lower in cells derived from aggregates cultured without OP9, indicating that its expression was dependent on Notch signaling (FIGS. 23D and 23E). The lack of hepatic markers, including ALB, AFP and CYP3A7 and the upregulation of expression the cholangiocyte markers CK19, SOX9 and CFTR in these structures was confirmed by RT-qPCR analyses (FIG. 16c). Similar CK19$^+$CFTR$^+$ tubular and cystic structures developed from iPSC-derived aggregates following culture under these conditions. Together, these findings show that when cultured in a mixture of matrigel and collagen, the hepatoblast population can generate ductal-like structures that express markers found in mature bile ducts.

Addition of GSI prevented the formation of the duct-like structures and cysts and promoted the development dense aggregates (FIG. 16a,b Spheres) that expressed ALB and low levels of CK19, suggesting that, in the absence of Notch signaling, cells with hepatoblast characteristics persist in the cultures. The addition of GSI also led to an increase in the expression of the hepatocyte markers (ALB, AFP and CYP3A7) and a decrease in the expression of the genes associated with cholangiocyte development (CK19, Sox9 and CFTR) (FIG. 16C).

hPSC-Derived Cholangiocytes Form Duct-Like Structures In Vivo.

Figure 17A:
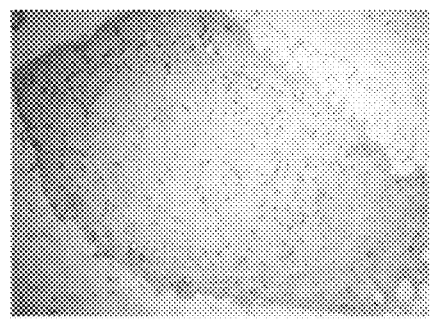
FIGS. 17A-17D demonstrate hPSC-derived cholangiocytes form duct-like structures in vivo.
Figure 17B:
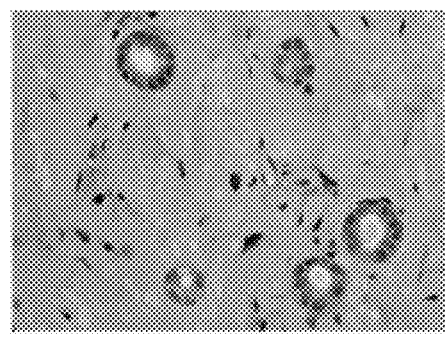
Figure 17C:
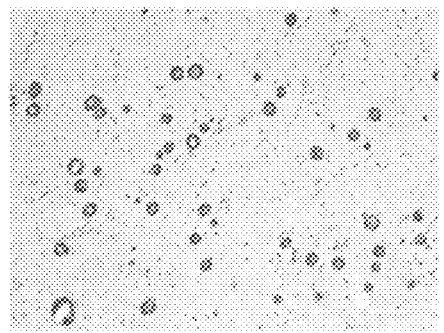
Figure 17D:
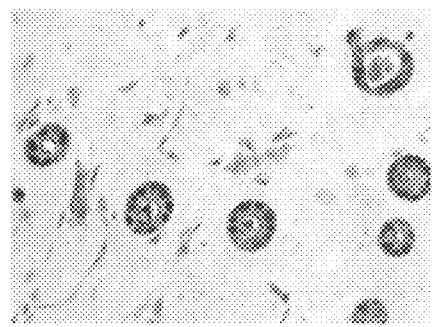

To evaluate the developmental potential of the hPSC-derived cholangiocytes in vivo, we transplanted them ($10^6$ cells) in a Matrigel plug into the mammary fat pad of immunodeficient NOD/SCID/IL2rg −/− (NSG) mice. For these studies, we used dissociated cells from branched structures generated by co-culture of a day 25 hepatoblast population derived from HES2-RFP hESCs with OP9 stroma. These hESCs were engineered to express RFP from the ROSA locus[9]. Six to eight weeks following transplantation, multiple duct-like structures were detected in the Matrigel plug (FIG. 17a,b). The cells within the ducts were RFP$^+$ demonstrating that they were of human origin, derived from the HES2-RFP cells (FIG. 17c,d). Additionally the cells expressed CK19 and CFTR, indicating that they displayed characteristics of cholangiocytes. As observed with the structures generated in vitro, CFTR expression segregated to apical side of the duct. Teratomas were not observed in any of the transplanted animals hPSCs derived cholangiocyte-like are functional As a first step to assess function of the hPSC-derived cholangiocytes, we evaluated their ability to efflux rhodamine123, a tracer dye used to measure the functional activity of the MDR1 transporter that is present in normal bile duct cells. The cystic structures derived from either H9 hESCs or the iPSCs transported dye to the luminal space, indicative of active transporter activity. In the presence of 20 µM verapamil, an inhibitor of the MDR transporter, rhodamine did not accumulate in the lumen of the structures confirming that the movement of the dye reflected active transport likely via the MDR transporter protein.

Figure 18A:
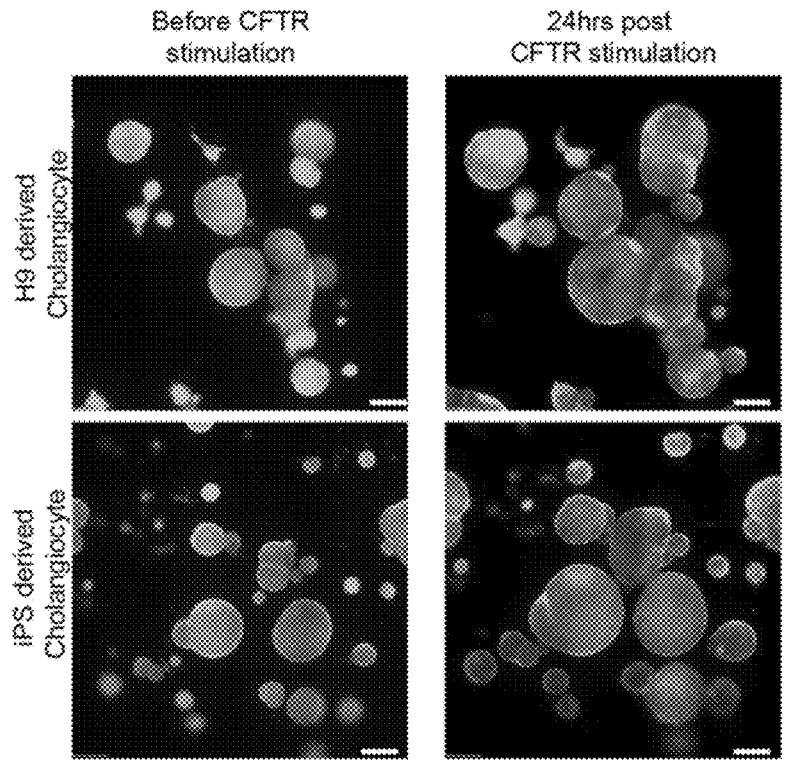
FIGS. 18A and 18B demonstrate that hPSC-derived cyst structures generated in 3D gels contain functional CFTR protein.
Figure 18B:
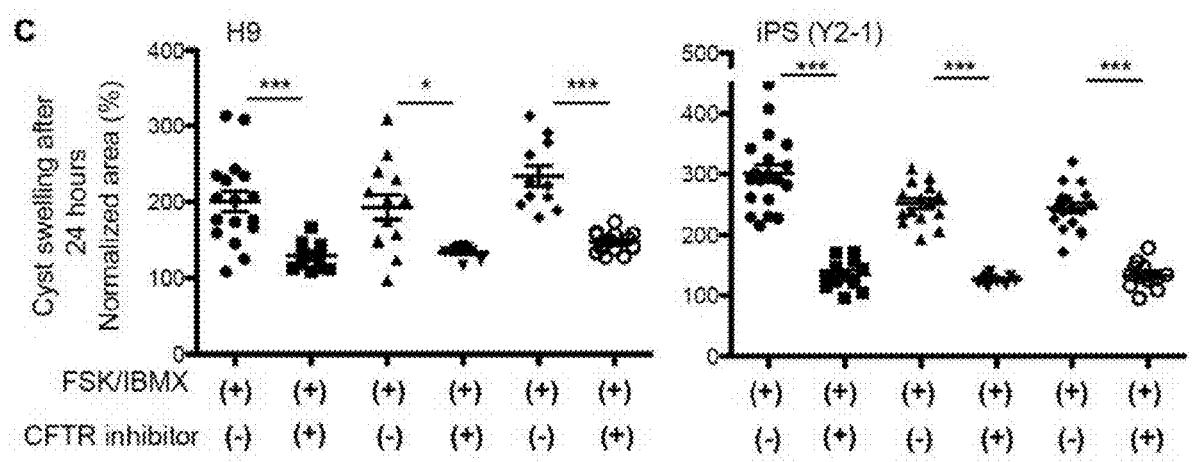

To demonstrate CFTR functional activity, we next carried out a forskolin-induced swelling assay on the cystic structures. With this assay, activation of the cAMP pathway by the addition of Forskolin/IBMX increases CFTR function resulting in fluid transport and swelling of the cyst. Swelling can be visualized following staining with calcein green, a cell-permeable fluorescent dye (FIG. 18a). Addition of Forskolin and IBMX to the cultures induced 2.09+/−0.21 and 2.65+/−3.1 fold increases in the size of the H9- and iPSC-derived cysts respectively when measured 24 hours later (FIG. 18b). Addition of the CFTR inhibitor (CFTR$_{inh}$-172) blocked the Forskolin/IBMX induced swelling indicating that the increase in cyst size was CFTR dependent. The findings from these assays demonstrate that the cells in the hPSC-derived cyst/duct-like structures display properties of functional cholangiocyte cells found in hepatic bile ducts.

The Generation and Functional Analyses of Cholangiocytes from Cystic Fibrosis Patient iPSCs.

To demonstrate the utility of this system to model disease in vitro, we next analyzed cyst formation from iPSCs generated from two different cystic fibrosis patients carrying the common F508 deletion (e.g. deltaF508). Both hiPSC lines generated hepatoblast populations with kinetics similar to those observed for wild type hPSCs (FIG. 24a, b). Although hepatoblast development was not altered, cyst formation from the patient iPSCs was clearly impaired as only branched structures were observed in the gels following two weeks of culture (FIG. 19a). Cyst formation from the patient cells could be induced by the addition of forskolin for the first week of the two-week culture period (change) (FIG. 19a,b). However, many of the cysts that developed from the patient iPSC we not completely hollow, but rather contained branched ductal structures (FIG. 19c). A higher frequency of hollow cysts, typical of those that developed from normal iPSCs were detected following longer periods of culture, suggesting that maturation of the mutant cells was delayed. Addition of the CFTR inhibitors to cultures of normal iPSC-derived cholangiocytes also delayed cyst formation, indicating that the generation of these structures was dependent, to some degree, on a functional CFTR (FIG. 19b).

We next assessed functional restoration of F508 del CFTR in cholangiocyte like cells from cystic fibrosis patient iPSCs using the chemical correctors VX-809 and Corr-4a for 2 days in prior to CFTR functional assay. Both molecules function to correct folding defects of the mutant CFTR protein. The addition of the correctors did not improve cyst formation, but did result in the accumulation of detectable levels of CFTR on the apical site of lumen. Unlike the homogeneous distribution of CFTR in lumen of wild type cysts, however, the protein appeared in distinct patches in the patient-derived cysts treated with the corrector. This pattern may reflect incomplete rescue of the trafficking defect of the mutant protein. Western blot analyses also showed an effect of the addition of the correctors. The majority of CFTR in normal cells is the larger mature form identified by the upper band (C) in lane HBE in FIG. 20A. The patient derived cells contained much less CFTR protein and the majority was the smaller immature form. Addition of the correctors dramatically increased the proportion of mature protein in the patient cells. To determine if the correctors impact CFTR function, we next subjected the treated and not treated cysts to the forskolin/IBMX-induced swelling assay (FIG. 20 b,c). The patient specific cysts showed little swelling in the absence of the correctors. However, with the addition of the correctors, the cysts generated from patient C1 increased by approximately 2.18+/−0.52 fold where as those from patient 997 increased by 1.64+/−0.08 folds 24 hours following induction with forskolin/IBMX and VX770. Taken together, these findings show that it is possible to model aspects of CFTR dysfunction in the patient specific iPSC-derived cholangiocytes and that correctors used to treat these patients can rescue the defect.

Discussion

A system for the directed differentiation of hPSCs into functional cholangiocyte-like cells that self-organize into duct-like structures in vitro and in vivo is described.

Murine studies suggested that Notch pathway is important for inducing cholangiocyte fate decision in vivo, including Jagged 1 interaction with portal mesenchyme cells and Notch 2 on hepatocytes.

Notch signaling provided by OP9 cells successfully manipulated the fate decision in not only monolayer, but also three dimensional gel cultures. Reversed effect was observed when Notch signaling was affected in addition to G secretase inhibitor. Previous reports have shown that cholangiocyte-like duct structures generated, albeit in low efficiency, from human ES cells resulted in showing the function with polarity and rhodamine 123 uptake Notch signaling provided by OP9 promoted the engraftments from human ES derived cholangiocyte-like cells and cells formed the RFP-positive duct-like structures in mouse mammary fat pad. These structures were not observed in the absence of OP9. Taken together, OP9 co-culture system efficiently provides notch signaling to induce cholangiocyte-like cells from human PSCs derived-hepatoblasts both in vitro and in vivo.

Hepatocyte maturation from hPSCs is shown to be enhanced by three dimensional culture environments herein. Similarly, maturation of cholangiocyte lineage cells was also promoted by three dimensional gel culture system. When hepatoblast aggregates stimulated by Notch signaling via OP9 cells, gene expression associated with cholangiocyte lineage and maturation was significantly increased. Furthermore functional activity as a cholangiocyte was detected in vitro.

The human iPS-derived cholangiocyte-like duct structure demonstrated functional CFT activity. These cells can be used for drug screening in a patient-specific manner.

Furthermore, patient-specific cholangiocyte-like duct structures can be obtained efficiently and used to validate existing or new therapeutic drugs and other severe biliary diseases such as the monogenic conditions progressive familial intrahepatic cholestasis (PFIC types 1, 2 and 3), and Alagille syndrome, and the more common and complex biliary diseases, biliary atresia and primary sclerosing cholangitis.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

REFERENCES

1. Gebhardt, R. et al. New hepatocyte in vitro systems for drug metabolism: metabolic capacity and recommendations for application in basic research and drug development, standard operation procedures. *Drug Metab Rev* 35, 145-213 (2003).
2. Guillouzo, A. Liver cell models in in vitro toxicology. *Environ Health Perspect* 106 Suppl 2, 511-532 (1998).
3. Hewitt, N. J. et al. Primary hepatocytes: current understanding of the regulation of metabolic enzymes and transporter proteins, and pharmaceutical practice for the use of hepatocytes in metabolism, enzyme induction, transporter, clearance, and hepatotoxicity studies. *Drug Metab Rev* 39, 159-234 (2007).
4. Byers, J. et al. An estimate of the number of hepatocyte donors required to provide reasonable estimates of human hepatic clearance from in vitro experiments. *Drug Metab Lett* 1, 91-95 (2007).
5. Kawasaki, S. et al. Living related liver transplantation in adults. *Ann Surg* 227, 269-274 (1998).
6. Hashikura, Y. et al. Successful living-related partial liver transplantation to an adult patient. *Lancet* 343, 1233-1234 (1994).
7. Miro, J., Laguno, M., Moreno, A. & Rimola, A. Management of end stage liver disease (ESLD): what is the current role of orthotopic liver transplantation (OLT)? *J Hepatol* 44, 5140-145 (2006).
8. Cai, J. et al. Directed differentiation of human embryonic stem cells into functional hepatic cells. *Hepatology* 45, 1229-1239 (2007).
9. Duan, Y. et al. Differentiation and enrichment of hepatocyte-like cells from human embryonic stem cells in vitro and in vivo. *Stem Cells* 25, 3058-3068 (2007).
10. Hay, D. C. et al. Highly efficient differentiation of hESCs to functional hepatic endoderm requires Activin A and Wnt3a signaling. *Proc Natl Acad Sci USA* 105, 12301-12306 (2008).
11. Basma, H. et al. Differentiation and transplantation of human embryonic stem cell-derived hepatocytes. *Gastroenterology* 136, 990-999 (2009).
12. Duan, Y. et al. Differentiation and characterization of metabolically functioning hepatocytes from human embryonic stem cells. *Stem Cells* 28, 674-686 (2010).
13. Sullivan, G. J. et al. Generation of functional human hepatic endoderm from human induced pluripotent stem cells. *Hepatology* 51, 329-335 (2010).
14. Touboul, T. et al. Generation of functional hepatocytes from human embryonic stem cells under chemically defined conditions that recapitulate liver development. *Hepatology* 51, 1754-1765 (2010).
15. Chen, Y. F. et al. Rapid generation of mature hepatocyte-like cells from human induced pluripotent stem cells by an efficient three-step protocol. *Hepatology* 55, 1193-1203 (2012).
16. Si-Tayeb, K. et al. Highly efficient generation of human hepatocyte-like cells from induced pluripotent stem cells. *Hepatology* 51, 297-305 (2010).
17. Si-Tayeb, K., Lemaigre, F. P. & Duncan, S. A. Organogenesis and development of the liver. *Dev Cell* 18, 175-189 (2010).
18. Nostro, M. C. et al. Stage-specific signaling through TGFbeta family members and WNT regulates patterning and pancreatic specification of human pluripotent stem cells. *Development* 138, 861-871 (2011).
19. Gadue, P., Huber, T. L., Paddison, P. J. & Keller, G. M. Wnt and TGF-beta signaling are required for the induction of an in vitro model of primitive streak formation using embryonic stem cells. *Proc Natl Acad Sci USA* 103, 16806-16811 (2006).

20. Gouon-Evans, V. et al. BMP-4 is required for hepatic specification of mouse embryonic stem cell-derived definitive endoderm. *Nat Biotechnol,* 24 1402-1411 (2006).
21. Borel Rinkes, I. H., Toner, M., Sheeha, S. J., Tompkins, R. G. & Yarmush, M. L. Long-term functional recovery of hepatocytes after cryopreservation in a three-dimensional culture configuration. *Cell Transplant* 1, 281-292 (1992).
22. Roberts, R. A. & Soames, A. R. Hepatocyte spheroids: prolonged hepatocyte viability for in vitro modeling of nongenotoxic carcinogenesis. *Fundam Appl Toxicol* 21, 149-158 (1993).
23. Sargiacomo, M. et al. Long-term cultures of human fetal liver cells: a three-dimensional experimental model for monitoring liver tissue development. *J Hepatol* 28, 480-490 (1998).
24. Miki, T., Ring, A. & Gerlach, J. Hepatic differentiation of human embryonic stem cells is promoted by three-dimensional dynamic perfusion culture conditions. *Tissue Eng Part C Methods* 17, 557-568 (2011).
25. Dankel, S. N., Hoang, T., Flageng, M. H., Sagen, J. V. & Mellgren, G. cAMP-mediated regulation of HNF-4alpha depends on the level of coactivator PGC-1 alpha. *Biochim Biophys Acta* 1803, 1013-1019 (2010).
26. Benet, M., Lahoz, A., Guzman, C, Castell, J. V. & Jover, R. CCAAT/enhancer-binding protein alpha (C/EBPalpha) and hepatocyte nuclear factor 4alpha (HNF4alpha) synergistically cooperate with constitutive androstane receptor to transactivate the human cytochrome P450 2B6 (CYP2B6) gene: application to the development of a metabolically competent human hepatic cell model. *J Biol Chem* 285, 28457-28471 (2010).
27. Bell, A. W. & Michalopoulos, G. K. Phenobarbital regulates nuclear expression of HNF-4alpha in mouse and rat hepatocytes independent of CAR and PXR. *Hepatology* 44, 186-194 (2006).
28. Arpiainen, S. et al. Coactivator PGC-1 alpha regulates the fasting inducible xenobiotic-metabolizing enzyme CYP2A5 in mouse primary hepatocytes. *Toxicol Appl Pharmacol* 232, 135-141 (2008).
29. Stieger, B., Heger, M., de Graaf, W., Paumgartner, G. & van Gulik, T. The emerging role of transport systems in liver function tests. *Eur J Pharmacol* 675, 1-5 (2012).
30. Huet, P. M. & Villeneuve, J. P. Determinants of drug disposition in patients with cirrhosis. *Hepatology* 3, 913-918 (1983).
31. Hines, R. N. & McCarver, D. G. The ontogeny of human drug-metabolizing enzymes: phase I oxidative enzymes. *J Pharmacol Exp Ther* 300, 355-360 (2002).
32. Nagamoto, Y. et al. The promotion of hepatic maturation of human pluripotent stem cells in 3D co-culture using type collagen and Swiss 3T3 cell sheets. *Biomaterials* 33, 4526-4534 (2012).
33. Takayama, K. et al. Efficient generation of functional hepatocytes from human embryonic stem cells and induced pluripotent stem cells by HNF4alpha transduction. *Mol Ther* 20, 127-137 (2012).
34. Takayama, K. et al. Efficient and directive generation of two distinct endoderm lineages from human ESCs and iPSCs by differentiation stage-specific SOX17 transduction. *PLoS One* 6, e21780 (2011).
35. Green, M. D. et al. Generation of anterior foregut endoderm from human embryonic and induced pluripotent stem cells. *Nat Biotechnol* 29, 267-272 (2011).
36. Spence, J. R. et al. Directed differentiation of human pluripotent stem cells into intestinal tissue in vitro. *Nature* 470, 105-109 (2011).
37. Koyama, T., Ehashi, T., Ohshima, N. & Miyoshi, H. Efficient proliferation and maturation of fetal liver cells in three-dimensional culture by stimulation of oncostatin M, epidermal growth factor, and dimethyl sulfoxide. *Tissue Eng Part A* 15, 1099-1107 (2009).
38. Ring, A. et al. Hepatic maturation of human fetal hepatocytes in four-compartment three-dimensional perfusion culture. *Tissue Eng Part C Methods* 16, 835-845 (20 0).
39. Montoliu, L, Blendy, J. A., Cole, T. J. & Schutz, G. Analysis of the cAMP response on liver-specific gene expression in transgenic mice. *Fundam Clin Pharmacol* 8, 38-146 (1994).
40. Leopold, J. A. et al. Aldosterone impairs vascular reactivity by decreasing glucose-6-phosphate dehydrogenase activity. *Nat Med* 13, 189-197 (2007).
41. Liu, Y. et al. A fasting inducible switch modulates gluconeogenesis via activator/coactivator exchange. *Nature* 456, 269-273 (2008).
42. Herzig, S. et al. CREB regulates hepatic gluconeogenesis through the coactivator PGC-1. *Nature* 179-183 (2001).
43. Lin, J. et al. PGC-1 beta in the regulation of hepatic glucose and energy metabolism. *J Biol Chem* 278, 30843-30848 (2003).
44. Kennedy, M., D'Souza, S. L., Lynch-Kattman, M., Schwantz, S. & Keller, G. Development of the hemangioblast defines the onset of hematopoiesis in human E S cell differentiation cultures. *Blood* 109, 2679-2687 (2007).
45. Nostra, M. C., Cheng, X., Keller, G. M. & Gadue, P. Wnt, activin, and BMP signaling regulate distinct stages in the developmental pathway from embryonic stem cells to blood. *Cell Stem Cell* 2, 60-71 (2008).
46. Loboz, K. K., Gross, A. S., Ray, J. & McLachlan, A. J. HPLC assay for bupropion and its major metabolites in human plasma. *J Chromatogr B Analyt Technol Biomed Life Sci* 823, 115-121 (2005).
47. Gagne, J. F. et al. Common human UGT1A polymorphisms and the altered metabolism of irinotecan active metabolite 7-ethyl-10-hydroxycamptothecin (SN-38). *Mol Pharmacol* 62, 608-617 (2002).
48. Klipper-Aurbach, Y. et al. Mathematical formulae for the prediction of the residual beta cell function during the first two years of disease in children and adolescents with insulin-dependent diabetes mellitus. *Med Hypotheses* 45, 486-490 (1995).
49. Benjamini, Y., Drai, D., Elmer, G., Kafkafi, N. & Golani, I. Controlling the false discovery rate in behavior genetics research. *Behav Brain Res* 125, 279-284 (2001).
50. Zhang, F. & Chen, J. Y. HOMER: a human organ-specific molecular electronic repository. *BMC Bioinformatics* 12 Suppl 10, S4 (2011).
51. Allen, J. W. Hassanein, T & Bhatia S. N. Advances in Bioartificial Liver Devices. *Hepatology* 34:447-455 (2001).
52. Stange, J. Extracorporeal liver support. *Organogeneis* 7:1, 64-73 (2011).
53. Sato, N et al. Maintenance of pluripotency in human and mouse embryonic stem cells through activation of Wnt signaling by a pharmacological GSK-3 specific inhibitor. *Nature Medicine* 10:55-63 (2004).
54. Takebe, T et al. Vascularized and functional human liver from an iPSC-derived organ bud transplant. *Nature* 499: 481-4 (2013).

55. Yusa et al Targeted gene correction of alpha 1-antityrpsin deficiency in induced pluripotent stem cells *Nature* 478: 391-6 (2011).
56. Joung, J K and Jeffry D Sander TALENs: a widely applicable technology for targeted genome editing *Nature Reviews* 14: 49-55 (2013).
57. Ran F A et al Genome engineering using the CRISPR-Cas9 system *Nature Protocols* 8:2281-2308 (2013).
58. Gaj et al. ZFN, TALEN and CRISPR/CAs based methods for genome engineering. *Trends in Biotechnology* 31: 397-405 (2013).

The invention claimed is:

1. A method of producing hepatocyte and/or cholangiocyte lineage cells from pluripotent embryonic stem cells (PSCs) or induced pluripotent stem cells (iPSCs), the method comprising the following series of steps:
   (a) generating an induced endodermal cell population by either:
      i. culturing the PSCs or iPSCs in a monolayer in a medium comprising a nodal agonist and a Wnt/beta-catenin agonist for 3 days followed by 2 days in a medium comprising a Fibroblast Growth Factor (FGF) agonist and a nodal agonist; or
      ii. culturing the PSCs or iPSCs in medium comprising Bone Morphogenetic Protein 4 (BMP4) agonist for 12 to 36 hours to promote formation embryoid bodies (EBs) followed by 5 days in a medium comprising a FGF agonist, a nodal agonist, a Wnt/beta-catenin agonist, and a BMP4 agonist;
   (b) culturing the induced endodermal cell population in a medium comprising a nodal agonist for 1 to 4 days to provide an extended nodal agonist-treated induced endodermal cell population;
   (c) specifying the extended nodal agonist treated induced endodermal cell population to obtain a cell population comprising hepatoblasts by contacting the extended nodal agonist treated induced endodermal cell population with specification media comprising:
      i. a FGF agonist; and
      ii. a BMP4 agonist; and
   (d) inducing maturation, promoting further lineage specification, and/or inducing expansion of the hepatoblast population, comprising:
      i. dissociating the cell population comprising hepatoblasts;
      ii. generating aggregates of the dissociated cell population comprising hepatoblasts; and
      iii. culturing the aggregates in a maturation medium for 1 to 40 days to produce hepatocyte and/or cholangiocyte lineage cells, wherein the maturation medium comprises a CAMP signaling pathway activator and at least one of: hepatocyte growth factor (HGF); dexamethasone (DEX); and Oncostatin M (OSM),
wherein the nodal agonist is ActA, the Wnt/Beta-catenin agonist is Wnt3a, XAV939, CHIR 99021 or 6-bromo-Indirubin-3'-Oxime, the Fibroblast Growth Factor agonist is FGF-2, FGF-4 or FGF-10, the BMP4 agonist is BMP4, BMP2 or BMP7, and the CAMP signaling pathway activator is 8-bromoadenosine-3'5'-cyclic monophosphate.

2. The method of claim 1, wherein at least 90% of the induced endodermal cell population is $CXCR4^+$ and $cKIT^+$ or $CXCR4^+$ and $EPCAM^+$, and at least 90% of the induced endodermal cell population expresses SOX17 and at least 80% of the induced endodermal cell population expresses FOXA2.

3. The method of claim 1, wherein the Wnt/Beta-catenin agonist is Wnt3a and/or a GSK-3 selective inhibitor selected from CHIR-99021 or 6-bromo-Indirubin-3'-Oxime.

4. The method of claim 1, wherein the maturation medium further comprises a Wnt antagonist or a Mek/Erk antagonist, or both, wherein the Wnt antagonist is XAV939 IWP2, DKK1, IWR-1 endo or Wnt Inhibitory Factor-1 and wherein the Mek/Erk antagonist is PD0325901, U0126, PD098059.

5. The method of claim 1, wherein the maturation medium further comprises a Notch antagonist to promote hepatocyte lineage specification, wherein the Notch antagonist is gamma-secretase inhibitor (GSI) L695.458, DAPT, LY411575 or L-685458.

6. The method of claim 5, wherein the maturation medium further comprises a Wnt agonist or a TGFβ antagonist, or both, for 6 to 12 days, 8 to 10 days, or 9 days after cell aggregation, wherein the Wnt agonist is GSK3 selective inhibitor CHIR-99021, and wherein the TGFβ antagonist is SB431542, A83-01 or SB525334.

7. The method of claim 1, wherein the aggregates are cultured in maturation medium comprising EGF, TGFβ1 and HGF for 1 to 10 days after generating cell aggregates, and then Dex for about 1 to 10 days, and wherein the maturation medium further comprises a Notch agonist for 5 days to 90 days, wherein the Notch agonist is added within 1 to 10 days of the generating aggregates step, wherein the Notch agonist is a Notch signaling donor cell selected from OP-9 cell, OP9delta cell, and/or OP9 Jagged-1 cell.

8. The method of claim 5, wherein the hepatocytes produced are functional hepatocytes.

9. The method of claim 8, wherein the functional hepatocytes comprise increased expression and/or activity of:
   (a) at least one gene or protein selected from the group consisting of ALB, CPS1, G6P, TDO, CYP7A1, CYP3A7, CYP1A2, CYP3A4, CYP2B6, CYP2C9, CYP2D6, NAT2 and UGT1A1;
   (b) at least one protein selected from the group consisting of ALB, CPS1, G6P, TDO, CYP7A1, CYP3A7, CYP1A2, CYP3A4, CYP2B6, CYP2C9, CYP2D6, NAT2 and UGT1A1; or
   (c) both (a) and (b),
compared to a hepatoblast population.

10. The method of claim 8, wherein at least 40, 50, 60, 70, 80 or 90% of the functional hepatocytes are $ASGPR-1^+$.

11. The method of claim 2, wherein the cholangiocyte fate is specified by including a Notch agonist in the maturation medium, wherein the Notch agonist is a Notch signaling donor cell selected from OP-9 cell, OP9delta cell, and/or OP9 Jagged-1 cell.

12. The method of claim 11, wherein the hepatoblasts are cultured with the Notch agonist for at least 5, 8, 9, 10, 11, 12, 13, or to about 14 days, to induce further lineage specification, and/or maturation, or both, of the hepatocytes into cholangiocytes or functional cholangiocytes.

13. The method of claim 12, wherein the functional cholangiocytes comprise increased expression of:
   (a) at least 1 gene selected from SOX9, CK19, and CFTR (Cystic fibrosis transmembrane conductance regulator);
   (b) at least 1 protein selected from SOX9, CK19, and CFTR; or
   (c) both (a) and (b),
compared to a hepatoblast population not treated with a Notch agonist.

14. A method for generating a functional hepatocyte and/or cholangiocyte comprising:

(a) producing a cell population comprising hepatoblasts, according to the method of claim 1; and
(b) co-culturing the cell population comprising hepatoblasts for at least 4, 6, 8, 10, 12, 15, 20, 30, 40, 50, 60, or 90 days with:
  (i) a culture of aggregates of CD34+ endothelial cells to form a co-culture of chimeric aggregates comprising functional hepatocytes; or
  (ii) a culture of Notch signaling donor cells to form a co-culture of chimeric aggregates, wherein the aggregates are cultured with (EGF, TGFβ1, EGF and HGF), or (EGF, TGFβ1 and HGF) to produce a population of cells comprising functional cholangiocytes.

15. The method of claim 1 wherein the aggregates are embedded in a gel/matrix and 3D cultured.

16. The method of claim 8, further comprising administering the functional hepatocytes to a subject with a chronic liver disease.

17. The method of claim 16, wherein the chronic liver disease is cystic fibrosis liver syndrome, Alagille Syndrome, primary sclerosing cholangitis, or biliary atresia.

18. The method of claim 13, further comprising administering the functional hepatocytes to a subject with a chronic liver disease.

19. The method of claim 18, wherein the chronic liver disease is cystic fibrosis liver syndrome, Alagille Syndrome, primary sclerosing cholangitis, or biliary atresia.

20. The method of claim 6, wherein the TGFβ antagonist is SB431542.

21. The method of claim 4, wherein the Wnt antagonist is XAV939, and the Mek/Erk antagonist is PD0325901.

22. The method of claim 7, wherein the Notch agonist is a Notch signaling donor cell, comprising a Notch ligand bound to a cell surface, a plastic surface, an extracellular matrix (ECM) or the surface of a bead, wherein the Notch ligand is delta, Jagged-1, Jagged1 peptide, or Pref-1/DLK-1/FA1.

* * * * *